(12) United States Patent
Connor

(10) Patent No.: US 11,471,164 B2
(45) Date of Patent: Oct. 18, 2022

(54) METHODS OF OCCLUDING A CEREBRAL ANEURYSM BY INSERTING EMBOLIC MEMBERS OR MATERIAL INTO AN INTRASACULAR IMPLANT

(71) Applicant: Robert A. Connor, St. Paul, MN (US)

(72) Inventor: Robert A. Connor, St. Paul, MN (US)

(73) Assignee: Aneuclose LLC, St. Paul, MN (US)

( * ) Notice: Subject to any disclaimer, the term of this patent is extended or adjusted under 35 U.S.C. 154(b) by 0 days.

(21) Appl. No.: 17/485,390

(22) Filed: Sep. 25, 2021

(65) Prior Publication Data

US 2022/0008082 A1    Jan. 13, 2022

Related U.S. Application Data

(63) Continuation-in-part of application No. 17/476,845, filed on Sep. 16, 2021, and a continuation-in-part of application No. 17/472,674, filed on Sep. 12, 2021, and a continuation-in-part of application No. 17/467,680, filed on Sep. 7, 2021, now abandoned, and a continuation-in-part of application No. 17/466,497, filed on Sep. 3, 2021, now Pat. No. 11,357,511, and a continuation-in-part of application No. 17/353,652, filed on Jun. 21, 2021, and a continuation-in-part of application No. 17/220,002, filed on Apr. 1, 2021, and a continuation-in-part of application No. 17/214,827, filed on Mar. 27, 2021, and a continuation-in-part of application No. 17/211,446, filed on Mar. 24, 2021, and a continuation-in-part of application No. 16/693,267,
(Continued)

(51) Int. Cl.
*A61B 17/12*    (2006.01)

(52) U.S. Cl.
CPC .. *A61B 17/12181* (2013.01); *A61B 17/12113* (2013.01); *A61B 17/12172* (2013.01)

(58) Field of Classification Search
CPC ........ A61B 17/12118; A61B 17/12113; A61B 17/12168; A61B 17/12177; A61B 17/12181
See application file for complete search history.

(56) References Cited

U.S. PATENT DOCUMENTS 6,346,117 B1 *  2/2002  Greenhalgh ..... A61B 17/12022
                                                          606/200
7,695,488 B2 *  4/2010  Berenstein ....... A61B 17/12177
                                                          606/191
(Continued)

OTHER PUBLICATIONS

U.S. Appl. No. 61/483,032, filed May 5, 2011, Kent et al.
(Continued)

*Primary Examiner* — Diane D Yabut
*Assistant Examiner* — Christina C Lauer

(57) ABSTRACT

Disclosed herein is a method for occluding a cerebral aneurysm which includes: delivering a flexible implant in a compressed first configuration to a cerebral aneurysm through a catheter; inserting the flexible implant into the aneurysm sac wherein the flexible implant self-expands to a second configuration; and then delivering embolic members and/or embolic material into the flexible implant to expand further the flexible implant into a third configuration which conforms to the walls of even an irregularly-shaped aneurysm sac.

3 Claims, 1 Drawing Sheet

Figure 1:
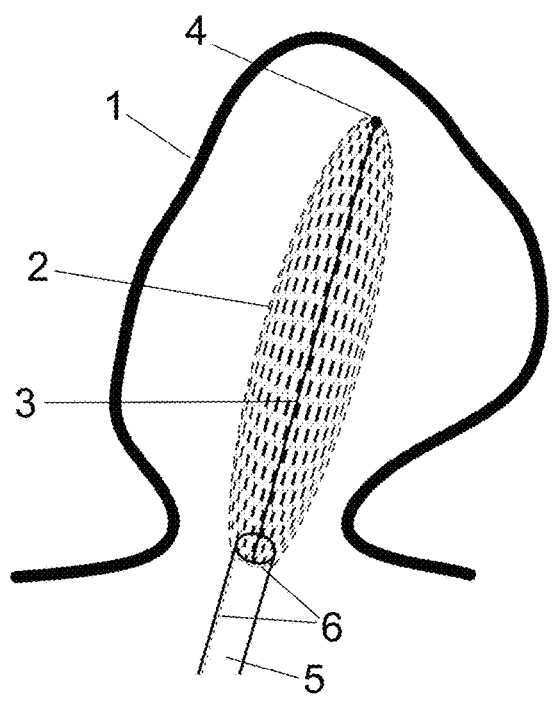

Related U.S. Application Data filed on Nov. 23, 2019, and a continuation-in-part of application No. 16/660,929, filed on Oct. 23, 2019, and a continuation-in-part of application No. 16/541,241, filed on Aug. 15, 2019, now abandoned, said application No. 17/220,002 is a continuation-in-part of application No. 17/214,827, filed on Mar. 27, 2021, and a continuation-in-part of application No. 17/211,446, filed on Mar. 24, 2021, and a continuation-in-part of application No. 16/693,267, filed on Nov. 23, 2019, and a continuation-in-part of application No. 16/660,929, filed on Oct. 23, 2019, said application No. 16/693,267 is a continuation-in-part of application No. 16/660,929, filed on Oct. 23, 2019, and a continuation-in-part of application No. 16/541,241, filed on Aug. 15, 2019, now abandoned, and a continuation-in-part of application No. 15/865,822, filed on Jan. 9, 2018, now Pat. No. 10,716,573, and a continuation-in-part of application No. 15/861,482, filed on Jan. 3, 2018, now abandoned, said application No. 16/660,929 is a continuation-in-part of application No. 16/541,241, filed on Aug. 15, 2019, now abandoned, and a continuation-in-part of application No. 15/865,822, filed on Jan. 9, 2018, now Pat. No. 10,716,573, and a continuation-in-part of application No. 15/861,482, filed on Jan. 3, 2018, now abandoned, said application No. 16/541,241 is a continuation-in-part of application No. 15/865,822, filed on Jan. 9, 2018, now Pat. No. 10,716,573, which is a continuation-in-part of application No. 15/081,909, filed on Mar. 27, 2016, now abandoned, and a continuation-in-part of application No. 14/526,600, filed on Oct. 29, 2014, now abandoned, said application No. 15/861,482 is a continuation-in-part of application No. 15/080,915, filed on Mar. 25, 2016, now Pat. No. 10,028,747, and a continuation-in-part of application No. 14/526,600, filed on Oct. 29, 2014, now abandoned, said application No. 15/081,909 is a continuation-in-part of application No. 14/526,600, filed on Oct. 29, 2014, now abandoned, said application No. 15/080,915 is a continuation-in-part of application No. 14/526,600, filed on Oct. 29, 2014, now abandoned, which is a continuation-in-part of application No. 12/989,048, filed on Oct. 21, 2010, now Pat. No. 8,974,487.

(60) Provisional application No. 63/119,774, filed on Dec. 1, 2020, provisional application No. 62/794,609, filed on Jan. 19, 2019, provisional application No. 62/794,607, filed on Jan. 19, 2019, provisional application No. 62/720,173, filed on Aug. 21, 2018, provisional application No. 62/589,754, filed on Nov. 22, 2017, provisional application No. 62/472,519, filed on Mar. 16, 2017, provisional application No. 62/444,860, filed on Jan. 11, 2017, provisional application No. 61/897,245, filed on Oct. 30, 2013, provisional application No. 61/126,047, filed on May 1, 2008, provisional application No. 61/126,027, filed on May 1, 2008.

(56) References Cited

U.S. PATENT DOCUMENTS

| | | |
|---|---|---|
| 8,597,320 B2 | 12/2013 | Sepetka et al. |
| 8,974,512 B2 | 3/2015 | Aboytes et al. |
| 8,998,947 B2 | 4/2015 | Aboytes et al. |
| 9,039,726 B2 | 5/2015 | Becking |
| 9,078,658 B2 | 7/2015 | Hewitt et al. |
| 9,492,174 B2 | 11/2016 | Hewitt et al. |
| 9,585,669 B2 | 3/2017 | Becking et al. |
| 9,629,635 B2 | 4/2017 | Hewitt et al. |
| 9,955,976 B2 | 5/2018 | Hewitt et al. |
| 9,980,733 B2 | 5/2018 | Badruddin et al. |
| 10,130,372 B2 | 11/2018 | Griffin |
| 10,265,075 B2 | 4/2019 | Porter et al. |
| 10,285,711 B2 | 5/2019 | Griffin |
| 10,314,593 B2 | 6/2019 | Bardsley et al. |
| 10,327,781 B2 | 6/2019 | Divino et al. |
| 10,383,635 B2 | 8/2019 | Wallace et al. |
| 10,398,441 B2 | 9/2019 | Warner et al. |
| 10,426,486 B2 | 10/2019 | Guo et al. |
| 10,433,853 B2 | 10/2019 | Divino et al. |
| 10,595,875 B2 | 3/2020 | Mayer et al. |
| 10,610,231 B2 | 4/2020 | Marchand et al. |
| 10,617,426 B2 | 4/2020 | Aboytes et al. |
| 10,617,427 B2 | 4/2020 | Aboytes et al. |
| 10,653,425 B1 | 5/2020 | Gorochow et al. |
| 10,675,036 B2 | 6/2020 | Rosqueta et al. |
| 10,675,037 B2 | 6/2020 | Aboytes et al. |
| 10,716,574 B2 | 7/2020 | Lorenzo et al. |
| 10,729,447 B2 | 8/2020 | Shimizu et al. |
| 10,736,758 B2 | 8/2020 | Ruvalcaba et al. |
| 10,751,066 B2 | 8/2020 | Lorenzo |
| 10,813,645 B2 | 10/2020 | Hewitt et al. |
| 10,856,880 B1 | 12/2020 | Badruddin et al. |
| 10,869,672 B2 | 12/2020 | Griffin |
| 10,881,413 B2 | 1/2021 | Merritt et al. |
| 10,898,200 B2 | 1/2021 | Aboytes et al. |
| 10,905,430 B2 | 2/2021 | Lorenzo et al. |
| 10,905,431 B2 | 2/2021 | Gorochow |
| 10,925,612 B2 | 2/2021 | Wallace et al. |
| 10,939,914 B2 | 3/2021 | Hewitt et al. |
| 10,939,915 B2 | 3/2021 | Gorochow et al. |
| 10,939,916 B2 | 3/2021 | Aboytes et al. |
| 10,952,739 B2 | 3/2021 | Plaza et al. |
| 10,952,878 B2 | 3/2021 | Kusleika |
| 10,980,545 B2 | 4/2021 | Bowman et al. |
| 11,013,516 B2 | 5/2021 | Franano et al. |
| 11,033,275 B2 | 6/2021 | Franano et al. |
| 11,033,277 B2 | 6/2021 | Wolfe et al. |
| 11,045,203 B2 | 6/2021 | Sepetka et al. |
| 11,051,825 B2 | 7/2021 | Gorochow |
| 11,058,430 B2 | 7/2021 | Gorochow et al. |
| 11,058,431 B2 | 7/2021 | Pereira et al. |
| 11,071,551 B2 | 7/2021 | Garza et al. |
| 11,076,860 B2 | 8/2021 | Lorenzo |
| 11,076,861 B2 | 8/2021 | Gorochow et al. |
| 2002/0169473 A1 | 11/2002 | Sepetka et al. |
| 2006/0155323 A1 | 7/2006 | Porter et al. |
| 2008/0281350 A1 | 11/2008 | Sepetka et al. |
| 2009/0287294 A1 | 11/2009 | Rosqueta et al. |
| 2011/0022149 A1 | 1/2011 | Cox et al. |
| 2011/0208227 A1 | 8/2011 | Becking |
| 2012/0165919 A1 | 6/2012 | Cox et al. |
| 2012/0239074 A1 | 9/2012 | Aboytes et al. |
| 2012/0283768 A1 | 11/2012 | Cox et al. |
| 2013/0245667 A1 | 9/2013 | Marchand et al. |
| 2014/0052233 A1 | 2/2014 | Cox et al. |
| 2014/0135812 A1 | 5/2014 | Divino et al. |
| 2014/0358178 A1 | 12/2014 | Hewitt et al. |
| 2015/0209050 A1 | 7/2015 | Aboytes et al. |
| 2015/0216684 A1 | 8/2015 | Enzmann et al. |
| 2015/0272589 A1 | 10/2015 | Lorenzo |
| 2015/0272590 A1 | 10/2015 | Aboytes et al. |
| 2015/0297240 A1 | 10/2015 | Divino et al. |
| 2015/0313605 A1 | 11/2015 | Griffin |
| 2016/0022275 A1 | 1/2016 | Garza |
| 2016/0022445 A1 | 1/2016 | Ruvalcaba et al. |
| 2016/0213380 A1 | 7/2016 | O'Brien et al. |
| 2016/0249934 A1 | 9/2016 | Hewitt et al. |
| 2016/0249935 A1 | 9/2016 | Hewitt et al. |
| 2016/0249937 A1 | 9/2016 | Marchand et al. |
| 2016/0262766 A1 | 9/2016 | Aboytes et al. |
| 2016/0367260 A9 | 12/2016 | Hewitt et al. |

(56) References Cited

U.S. PATENT DOCUMENTS

| | | |
|---|---|---|
| 2017/0079661 A1 | 3/2017 | Bardsley et al. |
| 2017/0079662 A1 | 3/2017 | Rhee et al. |
| 2017/0086851 A1 | 3/2017 | Wallace et al. |
| 2017/0095254 A1 | 5/2017 | Hewitt et al. |
| 2017/0128077 A1 | 5/2017 | Hewitt et al. |
| 2017/0156733 A1 | 6/2017 | Becking et al. |
| 2017/0156734 A1 | 6/2017 | Griffin |
| 2017/0189035 A1 | 7/2017 | Porter |
| 2017/0258473 A1 | 9/2017 | Plaza et al. |
| 2017/0281194 A1 | 10/2017 | Divino et al. |
| 2017/0354418 A1 | 12/2017 | Teoh et al. |
| 2018/0000489 A1 | 1/2018 | Marchand et al. |
| 2018/0036012 A1 | 2/2018 | Aboytes et al. |
| 2018/0070955 A1 | 3/2018 | Greene et al. |
| 2018/0092690 A1 | 4/2018 | Priya et al. |
| 2018/0132859 A1 | 5/2018 | Aboytes et al. |
| 2018/0132862 A1 | 5/2018 | Aboytes et al. |
| 2018/0206849 A1 | 7/2018 | Hewitt et al. |
| 2018/0242979 A1 | 8/2018 | Lorenzo |
| 2018/0250013 A1 | 9/2018 | Wallace et al. |
| 2018/0271540 A1 | 9/2018 | Merritt et al. |
| 2018/0303486 A1 | 10/2018 | Rosenbluth et al. |
| 2019/0008522 A1 | 1/2019 | Lorenzo |
| 2019/0053810 A1 | 2/2019 | Griffin |
| 2019/0053811 A1 | 2/2019 | Garza et al. |
| 2019/0059909 A1 | 2/2019 | Griffin |
| 2019/0105054 A1 | 4/2019 | Aboytes et al. |
| 2019/0105056 A1 | 4/2019 | Aboytes et al. |
| 2019/0133794 A1 | 5/2019 | Kusleika |
| 2019/0192166 A1 | 6/2019 | Hewitt et al. |
| 2019/0192168 A1 | 6/2019 | Lorenzo et al. |
| 2019/0201000 A1 | 7/2019 | Wallace et al. |
| 2019/0209178 A1 | 7/2019 | Richter et al. |
| 2019/0209181 A1 | 7/2019 | Mayer et al. |
| 2019/0216467 A1 | 7/2019 | Goyal |
| 2019/0223878 A1 | 7/2019 | Lorenzo et al. |
| 2019/0223881 A1 | 7/2019 | Hewitt et al. |
| 2019/0254676 A1 | 8/2019 | Murphy et al. |
| 2019/0262002 A1 | 8/2019 | Benjamin |
| 2019/0269411 A1 | 9/2019 | Bardsley et al. |
| 2019/0269414 A1 | 9/2019 | Griffin |
| 2019/0274691 A1 | 9/2019 | Sepetka et al. |
| 2019/0282242 A1 | 9/2019 | Divino et al. |
| 2019/0290286 A1 | 9/2019 | Divino et al. |
| 2019/0298379 A1 | 10/2019 | Porter et al. |
| 2019/0307460 A1 | 10/2019 | Ferrera et al. |
| 2019/0307546 A1 | 10/2019 | Aguilar et al. |
| 2019/0343532 A1 | 11/2019 | Divino et al. |
| 2019/0343664 A1 | 11/2019 | Ruvalcaba et al. |
| 2019/0350590 A1 | 11/2019 | Aboytes et al. |
| 2019/0362496 A1 | 11/2019 | Dutta et al. |
| 2019/0365385 A1 | 12/2019 | Gorochow et al. |
| 2019/0365472 A1 | 12/2019 | Connor |
| 2019/0374228 A1 | 12/2019 | Wallace et al. |
| 2020/0038032 A1 | 2/2020 | Rhee et al. |
| 2020/0038035 A1 | 2/2020 | Griffin |
| 2020/0113576 A1 | 4/2020 | Gorochow et al. |
| 2020/0138447 A1 | 5/2020 | Rosqueta et al. |
| 2020/0155333 A1 | 5/2020 | Franano et al. |
| 2020/0163677 A1 | 5/2020 | Mayer et al. |
| 2020/0163784 A1 | 5/2020 | Franano et al. |
| 2020/0187952 A1 | 6/2020 | Walsh et al. |
| 2020/0187953 A1 | 6/2020 | Hamel et al. |
| 2020/0187954 A1 | 6/2020 | Hamel et al. |
| 2020/0197017 A1 | 6/2020 | Hamel et al. |
| 2020/0197018 A1 | 6/2020 | Hamel et al. |
| 2020/0197020 A1 | 6/2020 | Hamel et al. |
| 2020/0205841 A1 | 7/2020 | Aboytes et al. |
| 2020/0281603 A1 | 9/2020 | Marchand et al. |
| 2020/0289124 A1 | 9/2020 | Rangwala et al. |
| 2020/0289125 A1 | 9/2020 | Dholakia et al. |
| 2020/0289126 A1 | 9/2020 | Hewitt et al. |
| 2020/0360025 A1 | 11/2020 | Wallace et al. |
| 2020/0367893 A1 | 11/2020 | Xu et al. |
| 2020/0367898 A1 | 11/2020 | Gorochow et al. |
| 2020/0367900 A1 | 11/2020 | Pedroso et al. |
| 2020/0367901 A1 | 11/2020 | Porter et al. |
| 2020/0367906 A1 | 11/2020 | Xu et al. |
| 2020/0375606 A1 | 12/2020 | Lorenzo |
| 2020/0375607 A1 | 12/2020 | Soto Del Valle et al. |
| 2020/0397447 A1 | 12/2020 | Lorenzo et al. |
| 2020/0405347 A1 | 12/2020 | Walzman |
| 2021/0007754 A1 | 1/2021 | Milhous et al. |
| 2021/0007755 A1 | 1/2021 | Lorenzo et al. |
| 2021/0022765 A1 | 1/2021 | Walzman |
| 2021/0045750 A1 | 2/2021 | Wolf et al. |
| 2021/0052278 A1 | 2/2021 | Mauger |
| 2021/0052279 A1 | 2/2021 | Porter et al. |
| 2021/0068842 A1 | 3/2021 | Griffin |
| 2021/0069387 A1 | 3/2021 | Chen et al. |
| 2021/0085333 A1 | 3/2021 | Gorochow et al. |
| 2021/0106337 A1 | 4/2021 | Hewitt et al. |
| 2021/0106338 A1 | 4/2021 | Gorochow |
| 2021/0128160 A1 | 5/2021 | Li et al. |
| 2021/0128162 A1 | 5/2021 | Rhee et al. |
| 2021/0128165 A1 | 5/2021 | Pulugurtha et al. |
| 2021/0128167 A1 | 5/2021 | Patel et al. |
| 2021/0128168 A1 | 5/2021 | Nguyen et al. |
| 2021/0128169 A1 | 5/2021 | Li et al. |
| 2021/0129275 A1 | 5/2021 | Nguyen et al. |
| 2021/0137526 A1 | 5/2021 | Lee et al. |
| 2021/0137529 A1 | 5/2021 | Chen |
| 2021/0137715 A1 | 5/2021 | Ringwala et al. |
| 2021/0145449 A1 | 5/2021 | Gorochow |
| 2021/0153871 A1 | 5/2021 | Griffin |
| 2021/0153872 A1 | 5/2021 | Nguyen et al. |
| 2021/0169495 A1 | 6/2021 | Gorochow et al. |
| 2021/0169496 A1 | 6/2021 | Badruddin et al. |
| 2021/0169498 A1 | 6/2021 | Gorochow |
| 2021/0169499 A1 | 6/2021 | Merritt et al. |
| 2021/0177429 A1 | 6/2021 | Lorenzo |
| 2021/0186518 A1 | 6/2021 | Gorochow et al. |
| 2021/0196284 A1 | 7/2021 | Gorochow et al. |
| 2021/0204955 A1 | 7/2021 | Wallace et al. |
| 2021/0219982 A1 | 7/2021 | Badruddin et al. |
| 2021/0228214 A1 | 7/2021 | Bowman et al. |
| 2021/0244420 A1 | 8/2021 | Aboytes et al. |
| 2021/0251635 A1 | 8/2021 | Soto Del Valle et al. |
| 2021/0259699 A1 | 8/2021 | Rosenbluth et al. |
| 2021/0275184 A1 | 9/2021 | Hewitt et al. |
| 2021/0275187 A1 | 9/2021 | Franano et al. |
| 2021/0275188 A1 | 9/2021 | Plaza et al. |
| 2021/0275779 A1 | 9/2021 | Northrop |
| 2021/0282784 A1 | 9/2021 | Sepetka et al. |
| 2021/0282785 A1 | 9/2021 | Dholakia et al. |
| 2021/0282786 A1 | 9/2021 | Zaidat et al. |
| 2021/0282789 A1 | 9/2021 | Vu et al. |
| 2021/0282944 A1 | 9/2021 | Chen et al. |

OTHER PUBLICATIONS

U.S. Appl. No. 61/866,993, filed Aug. 16, 2013, Hewitt et al.
U.S. Appl. No. 61/979,416, filed Apr. 14, 2014, Hewitt et al.
U.S. Appl. No. 62/093,313, filed Dec. 17, 2014, Hewitt et al.
U.S. Appl. No. 62/307,123, filed Mar. 11, 2016, Plaza et al.
U.S. Appl. No. 62/819,296, filed Mar. 15, 2019, Rangwala et al.
U.S. Appl. No. 62/819,317, filed Mar. 15, 2019, Dholakia et al.
U.S. Appl. No. 62/873,256, filed Jul. 12, 2019, Milhous et al.

* cited by examiner

METHODS OF OCCLUDING A CEREBRAL ANEURYSM BY INSERTING EMBOLIC MEMBERS OR MATERIAL INTO AN INTRASACULAR IMPLANT

CROSS-REFERENCE TO RELATED APPLICATIONS

This application is a continuation-in-part of U.S. patent application Ser. No. 17/476,845 filed on 2021 Sep. 16, is a continuation-in-part of U.S. patent application Ser. No. 17/472,674 filed on 2021 Sep. 12, is a continuation-in-part of U.S. patent application Ser. No. 17/467,680 filed on 2021 Sep. 7, is a continuation-in-part of U.S. patent application Ser. No. 17/466,497 filed on 2021 Sep. 3, is a continuation-in-part of U.S. patent application Ser. No. 17/353,652 filed on 2021 Jun. 21, is a continuation-in-part of U.S. patent application Ser. No. 17/220,002 filed on 2021 Apr. 1, is a continuation-in-part of U.S. patent application Ser. No. 17/214,827 filed on 2021 Mar. 27, is a continuation-in-part of U.S. patent application Ser. No. 17/211,446 filed on 2021 Mar. 24, claims the priority benefit of U.S. provisional patent application 63/119,774 filed on 2020 Dec. 1, is a continuation-in-part of U.S. patent application Ser. No. 16/693,267 filed on 2019 Nov. 23, is a continuation-in-part of U.S. patent application Ser. No. 16/660,929 filed on 2019 Oct. 23, and is a continuation-in-part of U.S. patent application Ser. No. 16/541,241 filed on 2019 Aug. 15.

U.S. patent application Ser. No. 17/220,002 was a continuation-in-part of U.S. patent application Ser. No. 17/214,827 filed on 2021 Mar. 27. U.S. patent application Ser. No. 17/220,002 was a continuation-in-part of U.S. patent application Ser. No. 17/211,446 filed on 2021 Mar. 24. U.S. patent application Ser. No. 17/220,002 claimed the priority benefit of U.S. provisional patent application 63/119,774 filed on 2020 Dec. 1. U.S. patent application Ser. No. 17/220,002 was a continuation-in-part of U.S. patent application Ser. No. 16/693,267 filed on 2019 Nov. 23. U.S. patent application Ser. No. 17/220,002 was a continuation-in-part of U.S. patent application Ser. No. 16/660,929 filed on 2019 Oct. 23.

U.S. patent application Ser. No. 16/693,267 was a continuation-in-part of U.S. patent application Ser. No. 16/660,929 filed on 2019 Oct. 23. U.S. patent application Ser. No. 16/693,267 claimed the priority benefit of U.S. provisional patent application 62/794,609 filed on 2019 Jan. 19. U.S. patent application Ser. No. 16/693,267 claimed the priority benefit of U.S. provisional patent application 62/794,607 filed on 2019 Jan. 19. U.S. patent application Ser. No. 16/693,267 was a continuation-in-part of U.S. patent application Ser. No. 16/541,241 filed on 2019 Aug. 15. U.S. patent application Ser. No. 16/693,267 was a continuation-in-part of U.S. patent application Ser. No. 15/865,822 filed on 2018 Jan. 9 which issued as U.S. patent Ser. No. 10/716,573 on 2020 Jul. 21 U.S. patent application Ser. No. 16/693,267 was a continuation-in-part of U.S. patent application Ser. No. 15/861,482 filed on 2018 Jan. 3.

U.S. patent application Ser. No. 16/660,929 claimed the priority benefit of U.S. provisional patent application 62/794,609 filed on 2019 Jan. 19. U.S. patent application Ser. No. 16/660,929 claimed the priority benefit of U.S. provisional patent application 62794607 filed on 2019 Jan. 19. U.S. patent application Ser. No. 16/660,929 was a continuation-in-part of U.S. patent application Ser. No. 16/541,241 filed on 2019 Aug. 15. U.S. patent application Ser. No. 16/660,929 was a continuation-in-part of U.S. patent application Ser. No. 15/865,822 filed on 2018 Jan. 9 which issued as U.S. patent Ser. No. 10/716,573 on 2020 Jul. 21 U.S. patent application Ser. No. 16/660,929 was a continuation-in-part of U.S. patent application Ser. No. 15/861,482 filed on 2018 Jan. 3.

U.S. patent application Ser. No. 16/541,241 claimed the priority benefit of U.S. provisional patent application 62/794,609 filed on 2019 Jan. 19. U.S. patent application Ser. No. 16/541,241 claimed the priority benefit of U.S. provisional patent application 62/794,607 filed on 2019 Jan. 19. U.S. patent application Ser. No. 16/541,241 claimed the priority benefit of U.S. provisional patent application 62/720,173 filed on 2018 Aug. 21. U.S. patent application Ser. No. 16/541,241 was a continuation-in-part of U.S. patent application Ser. No. 15/865,822 filed on 2018 Jan. 9 which issued as U.S. patent Ser. No. 10/716,573 on 2020 Jul. 21

U.S. patent application Ser. No. 15/865,822 claimed the priority benefit of U.S. provisional patent application 62/589,754 filed on 2017 Nov. 22. U.S. patent application Ser. No. 15/865,822 claimed the priority benefit of U.S. provisional patent application 62/472,519 filed on 2017 Mar. 16. U.S. patent application Ser. No. 15/865,822 was a continuation-in-part of U.S. patent application Ser. No. 15/081,909 filed on 2016 Mar. 27. U.S. patent application Ser. No. 15/865,822 was a continuation-in-part of U.S. patent application Ser. No. 14/526,600 filed on 2014 Oct. 29.

U.S. patent application Ser. No. 15/861,482 claimed the priority benefit of U.S. provisional patent application 62/589,754 filed on 2017 Nov. 22. U.S. patent application Ser. No. 15/861,482 claimed the priority benefit of U.S. provisional patent application 62/472,519 filed on 2017 Mar. 16. U.S. patent application Ser. No. 15/861,482 claimed the priority benefit of U.S. provisional patent application 62/444,860 filed on 2017 Jan. 11. U.S. patent application Ser. No. 15/861,482 was a continuation-in-part of U.S. patent application Ser. No. 15/080,915 filed on 2016 Mar. 25 which issued as U.S. patent Ser. No. 10/028,747 on 2018 Jul. 24 U.S. patent application Ser. No. 15/861,482 was a continuation-in-part of U.S. patent application Ser. No. 14/526,600 filed on 2014 Oct. 29.

U.S. patent application Ser. No. 15/081,909 was a continuation-in-part of U.S. patent application Ser. No. 14/526,600 filed on 2014 Oct. 29. U.S. patent application Ser. No. 15/080,915 was a continuation-in-part of U.S. patent application Ser. No. 14/526,600 filed on 2014 Oct. 29. U.S. patent application Ser. No. 14/526,600 claimed the priority benefit of U.S. provisional patent application 61/897,245 filed on 2013 Oct. 30. U.S. patent application Ser. No. 14/526,600 was a continuation-in-part of U.S. patent application Ser. No. 12/989,048 filed on 2010 Oct. 21 which issued as U.S. Pat. No. 8,974,487 on 2015 Mar. 10. U.S. patent application Ser. No. 12/989,048 claimed the priority benefit of U.S. provisional patent application 61/126,047 filed on 2008 May 1. U.S. patent application Ser. No. 12/989,048 claimed the priority benefit of U.S. provisional patent application 61/126,027 filed on 2008 May 1.

The entire contents of these related applications are incorporated herein by reference. Of these, the most directly relevant is U.S. patent application Ser. No. 12/989,048 filed on 2010 Oct. 21 which issued as U.S. Pat. No. 8,974,487 on 2015 Mar. 10.

FEDERALLY SPONSORED RESEARCH

Not Applicable

SEQUENCE LISTING OR PROGRAM

Not Applicable

BACKGROUND

Field of Invention

This invention relates to devices and methods for occluding a cerebral aneurysm.

Introduction

An aneurysm is an abnormal bulging of a blood vessel wall. The vessel from which the aneurysm protrudes is the parent vessel. Saccular aneurysms look like a sac protruding out from the parent vessel. Saccular aneurysms have a neck and can be prone to rupture. Fusiform aneurysms are a form of aneurysm in which a blood vessel is expanded circumferentially in all directions. Fusiform aneurysms generally do not have a neck and are less prone to rupturing than saccular aneurysms. As an aneurysm grows larger, its walls generally become thinner and weaker. This decrease in wall integrity, particularly for saccular aneurysms, increases the risk of the aneurysm rupturing and hemorrhaging blood into the surrounding tissue, with serious and potentially fatal health outcomes.

Cerebral aneurysms, also called brain aneurysms or intracranial aneurysms, are aneurysms that occur in the intercerebral arteries that supply blood to the brain. The majority of cerebral aneurysms form at the junction of arteries at the base of the brain that is known as the Circle of Willis where arteries come together and from which these arteries send branches to different areas of the brain. Although identification of intact aneurysms is increasing due to increased use of outpatient imaging such as outpatient MRI scanning, many cerebral aneurysms still remain undetected unless they rupture. If they do rupture, they often cause stroke, disability, and/or death. The prevalence of cerebral aneurysms is generally estimated to be in the range of 1%-5% of the general population or approximately 3-15 million people in the U.S. alone. Approximately 30,000 people per year suffer a ruptured cerebral aneurysm in the U.S. alone. Approximately one-third to one-half of people who suffer a ruptured cerebral aneurysm die within one month of the rupture. Sadly, even among those who survive, approximately one-half suffer significant and permanent deterioration of brain function. Better alternatives for cerebral aneurysm treatment are needed.

Review of the Relevant Art

U.S. patent applications 20120239074 (Aboytes et al., Sep. 20, 2012, "Devices and Methods for the Treatment of Vascular Defects"), 20150209050 (Aboytes et al., Jul. 30, 2015, "Devices and Methods for the Treatment of Vascular Defects"), and 20160262766 (Aboytes et al., Sep. 15, 2016, "Devices and Methods for the Treatment of Vascular Defects") disclose an intrasacular aneurysm occlusion device comprising an expandable implant with a first configuration in which the first portion and the second portion are substantially linearly aligned and a second configuration in which the second portion at least partially overlaps the first portion. U.S. Pat. No. 8,998,947 (Aboytes et al., Apr. 7, 2015, "Devices and Methods for the Treatment of Vascular Defects") discloses an expandable implant with a plurality of flattened, petal-shaped portions. U.S. patent application 20150272590 (Aboytes et al., Oct. 1, 2015, "Devices and Methods for the Treatment of Vascular Defects") discloses an expandable implant with a plurality of petals.

U.S. patent applications 20180036012 (Aboytes et al., Feb. 8, 2018, "Devices, Systems, and Methods for the Treatment of Vascular Defects") and 20190350590 (Aboytes et al., Nov. 21, 2019, "Devices, Systems, and Methods for Treatment of Vascular Defects") disclose an occlusion device with a directing region and a lead-in member that extends distally from the directing region. U.S. patent applications 20180132859 (Aboytes et al., May 17, 2018, "Devices and Methods for the Treatment of Vascular Defects"), 20200205841 (Aboytes et al., Jul. 2, 2020, "Devices, Systems, and Methods for the Treatment of Vascular Defects"), and 20210244420 (Aboytes et al., Aug. 12, 2021, "Devices and Methods for the Treatment of Vascular Defects") and U.S. Pat. No. 8,974,512 (Aboytes et al., Mar. 10, 2015, "Devices and Methods for the Treatment of Vascular Defects"), U.S. Pat. No. 10,617,427 (Aboytes et al., Apr. 14, 2020, "Devices and Methods for the Treatment of Vascular Defects"), and U.S. Pat. No. 1,089,8200 (Aboytes et al., Jan. 26, 2021, "Devices and Methods for the Treatment of Vascular Defects") disclose an implant which changes from a first configuration in which first and second portions are linearly aligned to a second configuration in which the second and first portions overlap.

U.S. patent applications 20180132862 (Aboytes et al., May 17, 2018, "Devices and Methods for the Treatment of Vascular Defects"), 20190105054 (Aboytes et al., Apr. 11, 2019, "Devices and Methods for the Treatment of Vascular Defects"), and 20190105056 (Aboytes et al., Apr. 11, 2019, "Devices and Methods for the Treatment of Vascular Defects"); and also U.S. patent Ser. No. 10/617,426 (Aboytes et al., Apr. 14, 2020, "Devices and Methods for the Treatment of Vascular Defects"), U.S. Pat. No. 1,067,5037 (Aboytes et al., Jun. 9, 2020, "Devices and Methods for the Treatment of Vascular Defects"), and U.S. Pat. No. 1,093,9916 (Aboytes et al., Mar. 9, 2021, "Devices and Methods for the Treatment of Vascular Defects") disclose an expandable mesh ribbon formed from a flattened tubular braid that curves into a predetermined three-dimensional shape.

U.S. patent application 20190307546 (Aguilar et al., Oct. 10, 2019, "Embolic Device with Improved Neck Coverage") discloses a series of alternating narrow portions and link portions, wherein each link portion circumscribes an opening in at least one plane, and wherein the structure forms a spiral shape when unconstrained. U.S. patent applications 20170079661 (Bardsley et al., Mar. 23, 2017, "Occlusive Devices") and 20190269411 (Bardsley et al., Sep. 5, 2019, "Occlusive Devices") and U.S. patent Ser. No. 10/314,593 (Bardsley et al., Jun. 11, 2019, "Occlusive Devices") disclose an implant with a single-layer or dual-layer braided body having a variable porosity. U.S. patent application 20190262002 (Benjamin, Aug. 29, 2019, "Novel Enhanced Orb-Like Intrasacular Device") discloses an intrasaccular occlusion device with an orb-like contiguous scaffold having zones of flexure and open cells.

U.S. Pat. No. 9,980,733 (Badruddin et al., May 29, 2018, "System for and Method of Treating Aneurysms") discloses a device with a cover whose diameter is greater than an aneurysm neck, such that a first portion of the cover contacts an interior surface of the aneurysm and a second portion covers the neck portion of the aneurysm. U.S. patent application 20210169496 (Badruddin et al., Jun. 10, 2021, "System for and Method of Treating Aneurysms") discloses an apparatus with a wire to be advanced within a tube and an occlusion element disposed on the wire, a cover, and an inner anchoring member. U.S. patent application 20210219982 (Badruddin et al., Jul. 22, 2021, "Systems and Methods for Treating Aneurysms") and U.S. patent Ser. No. 11/033,277 (Wolfe et al., Jun. 15, 2021, "Systems and Methods for Treating Aneurysms") disclose occlusive devices with a releasable joint on the proximal end of the device that is radially offset from its central longitudinal axis.

U.S. patent application 20110208227 (Becking, Aug. 25, 2011, "Filamentary Devices for Treatment of Vascular Defects") discloses braid balls for aneurysm occlusion with expanded globular and longitudinally-shortened configurations. U.S. Pat. No. 9,039,726 (Becking, May 26, 2015, "Filamentary Devices for Treatment of Vascular Defects") discloses braid balls for aneurysm occlusion having filaments that radially converge to a first cross-section to form filament tufts. U.S. Pat. No. 9,585,669 (Becking et al., Mar. 17, 2017, "Multiple Layer Filamentary Devices for Treatment of Vascular Defects") discloses a self-expanding resilient permeable shell with a proximal end, a distal end, a longitudinal axis, and a plurality of elongate resilient filaments. U.S. patent application 20170156733 (Becking et al., Jun. 8, 2017, "Multiple Layer Filamentary Devices for Treatment of Vascular Defects") and U.S. Pat. No. 9,585,669 (Becking et al., Mar. 17, 2017, "Multiple Layer Filamentary Devices for Treatment of Vascular Defects") disclose a self-expanding resilient permeable shell with a proximal end, a distal end, a longitudinal axis, and a plurality of elongate resilient filaments.

U.S. patent Ser. No. 10/980,545 (Bowman et al., Apr. 20, 2021, "Devices for Vascular Occlusion") discloses a braided wire device with a linear compressed shape within a catheter and an expanded state that expands away from an axis of a distal end a delivery pusher in a longitudinally angled and an axially offset manner. U.S. patent application 20210228214 (Bowman et al., Jul. 29, 2021, "Devices for Vascular Occlusion") discloses an occlusive device, an occlusive device delivery system, a method of delivering an occlusive device, and a method of making an occlusive device.

U.S. patent application 20210069387 (Chen et al., Mar. 11, 2021, "Intravascular Devices") discloses an implantable medical device with an elongate member having a cross-sectional dimension that is less than 0.00085 inch. U.S. patent application 20210282944 (Chen et al., Sep. 16, 2021, "Bifuracted Flow Diverter Systems") discloses a flow-diverting system. U.S. patent application 20210137529 (Chen, May 13, 2021, "Embolic Devices for Occluding Body Lumens") discloses an elongated member which forms a three-dimensional structure in response to body temperature. U.S. patent application 20190365472 (Connor, Dec. 5, 2019, "Using 3D Imaging and 3D Printing to Occlude a Cerebral Aneurysm") discloses the random ramblings of some eccentric washed-up academic who lives in the mid-west.

U.S. patent application 20110022149 (Cox et al., Jan. 27, 2011, "Methods and Devices for Treatment of Vascular Defects") discloses an expandable body support structure with first ends secured to a first ring and second ends secured to a second ring. U.S. patent application 20120283768 (Cox et al., Nov. 8, 2012, "Method and Apparatus for the Treatment of Large and Giant Vascular Defects") discloses deployment of multiple permeable shell devices. U.S. patent application 20140052233 (Cox et al., Feb. 20, 2014, "Methods and Devices for Treatment of Vascular Defects") discloses a method for treating a cerebral aneurysm by expanding a substantially spherical or globular shell. U.S. patent application 20120165919 (Cox et al., Jun. 28, 2012, "Methods and Devices for Treatment of Vascular Defects") discloses an expandable wire body support structure with a substantially spherical or globular configuration and a portion with low or no porosity.

U.S. provisional patent application 62/819,317 (Dholakia et al., Mar. 15, 2019, "Occlusion") discloses intrasaccular occlusive devices that utilize an apple-core braid winding shape. U.S. patent application 20210282785 (Dholakia et al., Sep. 16, 2021, "Devices Having Multiple Permeable Shells for Treatment of Vascular Defects") discloses occlusive devices with a plurality of permeable shells connected by a plurality of coils. U.S. patent application 20200289125 (Dholakia et al., Sep. 17, 2020, "Filamentary Devices Having a Flexible Joint for Treatment of Vascular Defects") discloses an implant with first and second permeable shells.

U.S. patent applications 20140135812 (Divino et al., May 15, 2014, "Occlusive Devices"), 20190282242 (Divino et al., Sep. 19, 2019, "Occlusive Devices"), 20190290286 (Divino et al., Sep. 26, 2019, "Occlusive Devices") and 20190343532 (Divino et al., Nov. 14, 2019, "Occlusive Devices") and U.S. patent Ser. No. 10/327,781 (Divino et al., Jun. 25, 2019, "Occlusive Devices") disclose a device with at least one expandable structure adapted to transition from a compressed configuration to an expanded configuration when released into the aneurysm. U.S. patent applications 20150297240 (Divino et al., Oct. 22, 2015, "Embolic Medical Devices") and 20170281194 (Divino et al., Oct. 5, 2017, "Embolic Medical Devices") disclose an intrasacular aneurysm occlusion device with a collapsed configuration in which its first and second side edges are curled toward each other around a longitudinal axis and an expanded configuration forming a series of loops wherein the first and second side edges uncurl. U.S. patent Ser. No. 10/433,853 (Divino et al., Oct. 8, 2019, "Embolic Medical Devices") discloses an occlusive device with first and second side edges which are curled toward each other about a longitudinal axis.

U.S. patent application 20190362496 (Dutta et al., Nov. 28, 2019, "Isolation of Aneurysm and Parent Vessel in Volumetric Image Data") discloses a framework for isolating an aneurysm and a parent vessel in volumetric image data. U.S. patent application 20150216684 (Enzmann et al., Aug. 6, 2015, "Dual Rotational Stent Apparatus and Method for Endovascular Treatment of Aneurysms") discloses a coaxial stent system with an inner treatment stent which is coaxially positioned inside an outer anchoring stent. U.S. patent application 20190307460 (Ferrera et al., Oct. 10, 2019, "Intrasacular Occlusion Devices Methods Processes and Systems") discloses a laser cut Nitinol device between 1.5 mm to 11.5 mm in size.

U.S. patent application 20200155333 (Franano et al., May 21, 2020, "Ballstent Device and Methods of Use") discloses a rounded, thin-walled, expandable metal structure ("ballstent"). U.S. patent Ser. No. 11/013,516 (Franano et al., May 25, 2021, "Expandable Body Device and Method of Use") discloses a single-lobed, thin-walled, expandable body ("ballstent" or "blockstent") and a flexible, elongated delivery device ("delivery catheter"). U.S. patent application 20200163784 (Franano et al., May 28, 2020, "Blockstent Device and Methods of Use") discloses a compressed, cylindrical or oblong, thin-walled, expandable metal structure and a flexible, elongated device which positions the compressed structure into a blood vessel segment. U.S. patent Ser. No. 11/033,275 (Franano et al., Jun. 15, 2021, "Expandable Body Device and Method of Use") discloses hollow gold structures that can be folded, wrapped, compressed, advanced to a location in the body of patient, and expanded by injection of a fluid. U.S. patent application 20210275187 (Franano et al., Sep. 9, 2021, "Expandable Body Device and Method of Use") discloses expandable bodies for aneurysm occlusion made with gold, platinum, or silver.

U.S. patent application 20160022275 (Garza, Jan. 28, 2016, "Covered Embolic Coils") discloses an embolic implant with a cover of unitary construction that is disposed about the exterior of a microcoil and does not extend into a lumen formed by the coil. U.S. patent application 20190053811 (Garza et al., Feb. 21, 2019, "Flow Attenuation Device") and U.S. patent Ser. No. 11/071,551 (Garza et al., Jul. 27, 2021, "Flow Attenuation Device") disclose an embolic device with a first coil segment, a second coil segment, and a mesh-screen segment, wherein the mesh-screen segment is disposed between the first coil segment and the second coil segment along a length of the embolic device.

U.S. patent Ser. No. 10/653,425 (Gorochow et al., May 19, 2020, "Layered Braided Aneurysm Treatment Device") discloses a tubular braid with an open end, a pinched end, and a predetermined shape. U.S. patent Ser. No. 10/905,431 (Gorochow, Feb. 2, 2021, "Spiral Delivery System for Embolic Braid") and U.S. patent application 20210106338 (Gorochow, Apr. 15, 2021, "Spiral Delivery System for Embolic Braid") disclose a device with a delivery tube having a spiral groove. U.S. patent Ser. No. 11/058,430 (Gorochow et al., Jul. 13, 2021, "Aneurysm Device and Delivery System") discloses a braided device with a proximal expandable portion for sealing an aneurysm neck and a distal expandable portion.

U.S. patent application 20190365385 (Gorochow et al., Dec. 5, 2019, "Aneurysm Device and Delivery System") and U.S. patent Ser. No. 10/751,066 (Lorenzo, Aug. 25, 2020, "Aneurysm Device and Delivery System") and U.S. Pat. No. 1,093,9915 (Gorochow et al., Mar. 9, 2021, "Aneurysm Device and Delivery System") disclose a braid with a distal end opposite a proximal end, wherein translating the braid causes the delivery portion to expand and form a distal sack as well as invert into itself. U.S. patent application 20200113576 (Gorochow et al., Apr. 16, 2020, "Folded Aneurysm Treatment Device and Delivery Method") discloses an implant with a braided section that folds to form an outer occlusive sack extending across a neck of an aneurysm to engage a wall of the aneurysm from within a sac of the aneurysm and an inner occlusive sack forming a trough nested within the outer occlusive sack.

U.S. patent application 20200367898 (Gorochow et al., Nov. 26, 2020, "Layered Braided Aneurysm Treatment Device") discloses a method of selecting a tubular braid comprising an open and pinched ends and inverting the tubular braid to form a predetermined shape. U.S. patent application 20210085333 (Gorochow et al., Mar. 25, 2021, "Inverting Braided Aneurysm Treatment System and Method") discloses a tubular braid with an open end, a pinched end, and a predetermined shape. U.S. patent application 20210145449 (Gorochow, May 20, 2021, "Implant Delivery System with Braid Cup Formation") discloses an implant system with an engagement wire, a pull wire, and a braided implant having a distal ring thereon. U.S. patent application 20210169495 (Gorochow et al., Jun. 10, 2021, "Intrasaccular Inverting Braid with Highly Flexible Fill Material") discloses a tubular braided implant including a braid that can be delivered as a single layer braid, invert into itself during deployment to form at least two nested sacks and an additional braid material that can fill the innermost sack.

U.S. patent application 20210169498 (Gorochow, Jun. 10, 2021, "Delivery of Embolic Braid") discloses a method for a braided implant with a band attached to a delivery tube. U.S. patent application 20210186518 (Gorochow et al., Jun. 24, 2021, "Implant Having an Intrasaccular Section and Intravascular Section") discloses a tubular braid with an intrasaccular section, an intravascular section, a pinched section, and a predetermined shape. U.S. patent application 20210196284 (Gorochow et al., Jul. 1, 2021, "Folded Aneurysm Treatment Device and Delivery Method") and U.S. patent Ser. No. 11/076,861 (Gorochow et al., Aug. 3, 2021, "Folded Aneurysm Treatment Device and Delivery Method") disclose a device with a braided implant within an aneurysm sack such that an outer non-inverted layer contacts a wall of the aneurysm and an inverted layer apposes the outer non-inverted layer to form a double layer of braid across a neck of the aneurysm. U.S. patent Ser. No. 11/051,825 (Gorochow, Jul. 6, 2021, "Delivery System for Embolic Braid") discloses a braided implant attached to a releasing component that can be detachably engaged with a delivery tube and a pull wire.

U.S. patent application 20190216467 (Goyal, Jul. 18, 2019, "Apparatus and Methods for Intravascular Treatment of Aneurysms") discloses a device with a first portion having an expandable and compressible mesh for expansion against the wall of an aneurysm and a second disk portion covering an outside of the neck opening. U.S. patent application 20180070955 (Greene et al., Mar. 15, 2018, "Embolic Containment") discloses a method of treating a neurovascular arteriovenous malformation comprising a catheter with a mesh catch structure on the distal portion of the catheter, wherein the catheter is configured to deliver liquid embolic and dimethyl sulfoxide.

U.S. patent applications 20150313605 (Griffin, Nov. 5, 2015, "Occlusion Device"), 20190053810 (Griffin, Feb. 21, 2019, "Occlusion Device"), 20190059909 (Griffin, Feb. 28, 2019, "Occlusion Device"), 20200038035 (Griffin, Feb. 6, 2020, "Occlusion Device"), and 20210068842 (Griffin, Mar. 11, 2021, "Occlusion Device") and also U.S. patent Ser. No. 10/130,372 (Griffin, Nov. 20, 2018, "Occlusion Device") disclose an occlusion device with a substantially solid marker with a distal end and a low profile resilient mesh body which is attached to the distal end. U.S. patent applications 20170156734 (Griffin, Jun. 8, 2017, "Occlusion Device") and 20190269414 (Griffin, Sep. 5, 2019, "Occlusion Device") and U.S. patent Ser. No. 10/285,711 (Griffin, May 14, 2019, "Occlusion Device") disclose an occlusion device comprising a continuous compressible mesh structure comprising axial mesh carriages configured end to end, wherein each end of each carriage is a pinch point in the continuous mesh structure. U.S. patent application 20190059909 (Griffin, Feb. 28, 2019, "Occlusion Device") discloses an occlusion device with a marker and a low profile resilient mesh body attached to the distal end of the marker, the body having a delivery shape and a deployed shape capable of conforming to aneurysm walls. U.S. patent Ser. No. 10/869,672 (Griffin, Dec. 22, 2020, "Occlusion Device") discloses an occlusion device with a dual layer of mesh and an inverted mushroom shape. U.S. patent application 20210153871 (Griffin, May 27, 2021, "Occlusion Device") discloses a continuous mesh structure comprising a medial pinch point.

U.S. patent applications 20200187953 (Hamel et al., Jun. 18, 2020, "Devices, Systems, and Methods for the Treatment of Vascular Defects"), 20200187954 (Hamel et al., Jun. 18, 2020, "Devices, Systems, and Methods for the Treatment of Vascular Defects"), 20200197017 (Hamel et al., Jun. 25, 2020, "Devices, Systems, and Methods for the Treatment of Vascular Defects"), 20200197018 (Hamel et al., Jun. 25, 2020, "Devices, Systems, and Methods for the Treatment of Vascular Defects"), and 20200197020 (Hamel et al., Jun. 25, 2020, "Devices, Systems, and Methods for the Treatment of Vascular Defects") disclose a mesh with a predetermined shape in which the mesh is curved along its width, is curved along its length, and has an undulating contour across at least a portion of one or both of its length or its width. U.S. patent Ser. No. 10/426,486 (Guo et al., Oct. 1, 2019, "Vaso-Occlusive Device Delivery System") discloses a vaso-occlusive device delivery assembly with a pusher assembly.

U.S. provisional patent application 61/866,993 (Hewitt et al., Aug. 16, 2013, "Filamentary Devices for Treatment of Vascular Defects") discloses a self-expanding resilient permeable structure wherein at least some elongate filaments include highly radiopaque material. U.S. provisional patent application 61/979,416 (Hewitt et al, Apr. 14, 2014, "Devices for Therapeutic Vascular Procedures") discloses a self-expanding resilient permeable shell with a plurality of elongate resilient filaments having a variable braided structure. U.S. patent application 20140358178 (Hewitt et al., Dec. 4, 2014, "Filamentary Devices for Treatment of Vascular Defects") discloses a resilient self-expanding permeable shell with at least 40% composite filaments relative to a total number of filaments, wherein composite filaments comprise a high strength material and a highly radiopaque material. U.S. provisional patent application 62/093,313 (Hewitt et al., Dec. 17, 2014, "Devices for Therapeutic Vascular Procedures") discloses a self-expanding resilient permeable shell with elongate resilient filaments having a variable braided structure, wherein a distal portion has a first braid density, a proximal portion has a second braid density, and the second braid density is greater than the first braid density.

U.S. Pat. No. 9,078,658 (Hewitt et al., Jul. 14, 2015, "Filamentary Devices for Treatment of Vascular Defects") discloses self-expanding resilient permeable shells with at least about 40% composite filaments having a high strength material and a highly radiopaque material. U.S. patent application 20160249935 (Hewitt et al., Sep. 1, 2016, "Devices for Therapeutic Vascular Procedures") discloses an expandable cylindrical structure made of wires and a self-expanding permeable shell at the distal end of the cylindrical structure. U.S. patent applications 20160249935 (Hewitt et al., Sep. 1, 2016, "Devices for Therapeutic Vascular Procedures") and 20160367260 (Hewitt et al., Dec. 22, 2016, "Devices for Therapeutic Vascular Procedures") disclose an intrasacular aneurysm occlusion device comprising a distal self-expanding resilient permeable shell, a proximal self-expanding resilient permeable shell, and an elongate support member between the distal and proximal permeable shells.

U.S. patent application 20160249934 (Hewitt et al., Sep. 1, 2016, "Filamentary Devices for Treatment of Vascular Defects") discloses a woven braided mesh having variable mesh density. U.S. Pat. No. 9,492,174 (Hewitt et al., Nov. 15, 2016, "Filamentary Devices for Treatment of Vascular Defects") discloses self-expanding permeable shells made with composite filaments having a diameter of 0.00075", 0.001", 0.0015", and/or 0.00125". U.S. patent application 20160367260 (Hewitt et al., Dec. 22, 2016, "Devices for Therapeutic Vascular Procedures") and U.S. Pat. No. 9,629,635 (Hewitt et al., Apr. 25, 2017, "Devices for Therapeutic Vascular Procedures") disclose an expandable structure with distal and proximal permeable shells having different pore sizes. U.S. patent application 20170095254 (Hewitt et al., May 6, 2017, "Filamentary Devices for Treatment of Vascular Defects") discloses an aneurysm occlusion device comprising a self-expanding permeable shell having a radially constrained elongated state configured for delivery within a catheter lumen, an expanded state with a globular and longitudinally shortened configuration relative to the radially constrained state, and a plurality of elongate filaments that are woven together, which define a cavity of the permeable shell.

U.S. patent application 20170128077 (Hewitt et al., May 11, 2017, "Devices for Therapeutic Vascular Procedures") discloses a self-expanding resilient permeable shell with a metallic coil secured at a distal end. U.S. Pat. No. 9,955,976 (Hewitt et al., May 1, 2018, "Filamentary Devices for Treatment of Vascular Defects") discloses a globular implant with distal and proximal regions whose pores have different average diameters. U.S. patent applications 20180206849 (Hewitt et al., Jul. 26, 2018, "Filamentary Devices for the Treatment of Vascular Defects") and 20200289126 (Hewitt et al., Sep. 17, 2020, "Filamentary Devices for Treatment of Vascular Defects") and U.S. Pat. No. 9,955,976 (Hewitt et al., May 1, 2018, "Filamentary Devices for Treatment of Vascular Defects") and U.S. Pat. No. 1,093,9914 (Hewitt et al., Mar. 9, 2021, "Filamentary Devices for the Treatment of Vascular Defects") disclose mesh balls with different layers and areas with different porosities.

U.S. patent application 20190192166 (Hewitt et al., Jun. 27, 2019, "Filamentary Devices for Treatment of Vascular Defects") and U.S. patent Ser. No. 10/813,645 (Hewitt et al., Oct. 27, 2020, "Filamentary Devices for Treatment of Vascular Defects") disclose resilient self-expanding permeable implants made with filaments having a diameter between about 0.0005 and about 0.005 inches. U.S. patent application 20190223881 (Hewitt et al., Jul. 25, 2019, "Devices for Therapeutic Vascular Procedures") discloses a self-expanding resilient permeable shell whose filaments have a distal region that extends beyond the distal end of the permeable shell and forms an extension having a generally-circular shape. U.S. patent application 20210275184 (Hewitt et al., Sep. 9, 2021, "Filamentary Devices for Treatment of Vascular Defects") discloses permeable shells made of woven braided mesh having a variable mesh density.

U.S. provisional patent application 61/483,032 (Kent et al., May 5, 2011, "Method and Apparatus for the Treatment of Large and Giant Vascular Defects") discloses various self-expanding shells, including some with double shells and layers. U.S. patent application 20190133794 (Kusleika, May 9, 2019, "Methods and Systems for Increasing a Density of a Region of a Vascular Device") and U.S. patent Ser. No. 10/952,878 (Kusleika, Mar. 23, 2021, "Methods and Systems for Increasing a Density of a Region of a Vascular Device") disclose a vascular device with an elastic member which increases the density of a by drawing proximal and distal ends of the region toward the other.

U.S. patent application 20210137526 (Lee et al., May 13, 2021, "Embolic Devices for Occluding Body Lumens") discloses an embolic device, wherein a cavity of a first three-dimensional structure is configured to accommodate a second three-dimensional structure. U.S. patent application 20210128169 (Li et al., May 6, 2021, "Devices, Systems, and Methods for Treatment of Intracranial Aneurysms") discloses systems and methods for treating an aneurysm including intravascularly delivering an occlusive member to an aneurysm cavity and deforming a shape of the occlusive member via introduction of an embolic element to a space between the occlusive member and an inner surface of the aneurysm wall.

U.S. patent applications 20150272589 (Lorenzo, Oct. 1, 2015, "Aneurysm Occlusion Device") and 20190008522 (Lorenzo, Jan. 10, 2019, "Aneurysm Occlusion Device") disclose a device with a control ring having a substantially annular body disposed on the proximal end region to prevent radial expansion of the proximal end region and to provide an engagement feature during manipulation of the occlusion device. U.S. patent application 20180242979 (Lorenzo, Aug. 30, 2018, "Aneurysm Device and Delivery System") discloses a self-expanding braided tubular member for treating an aneurysm. U.S. patent application 20190192168 (Lorenzo et al., Jun. 27, 2019, "Aneurysm Device and Delivery Method") discloses a braid which radially expands as a distal end exits a microcatheter, causing a distal segment to form an occlusive sack. U.S. patent application 20190223878 (Lorenzo et al., Jul. 25, 2019, "Aneurysm Device and Delivery System") discloses an aneurysm occlusion braid with inner and outer occlusive sacks.

U.S. patent Ser. No. 10/716,574 (Lorenzo et al., Jul. 21, 2020, "Aneurysm Device and Delivery Method") discloses a self-expanding braided device with an inverted outer occlusive sack. U.S. patent application 20200375606 (Lorenzo, Dec. 3, 2020, "Aneurysm Method and System") discloses a self-expanding braided implant with a distal implant end and a proximal implant end, the braided implant being invertible about the distal implant end. U.S. patent application 20210007755 (Lorenzo et al., Jan. 14, 2021, "Intrasaccular Aneurysm Treatment Device With Varying Coatings") discloses an implant with a braided mesh movable from a delivery configuration having a single-layer tubular shape to an implanted configuration sized to be implanted in an aneurysm sac. U.S. patent Ser. No. 10/905,430 (Lorenzo et al., Feb. 2, 2021, "Aneurysm Device and Delivery System") discloses a braided device with inner and outer meshes. U.S. patent application 20210177429 (Lorenzo, Jun. 17, 2021, "Aneurysm Method and System") discloses a vaso-occlusive device with at least two nested sacks. U.S. patent Ser. No. 11/076,860 (Lorenzo, Aug. 3, 2021, "Aneurysm Occlusion Device") discloses a tubular structure having a proximal end region and a distal end region, having an expanded condition and a collapsed condition.

U.S. patent application 20130245667 (Marchand et al., Sep. 19, 2013, "Filamentary Devices and Treatment of Vascular Defects") discloses a self-expanding resilient permeable shell with filaments which are bundled and secured to each other at a proximal end. U.S. patent application 20160249937 (Marchand et al., Sep. 1, 2016, "Multiple Layer Filamentary Devices for Treatment of Vascular Defects") discloses an occlusion device with a number of undulations. U.S. patent application 20180000489 (Marchand et al., Jan. 4, 2018, "Filamentary Devices for Treatment of Vascular Defects") and U.S. patent Ser. No. 10/610,231 (Marchand et al., Apr. 7, 2020, "Filamentary Devices for Treatment of Vascular Defects") disclose a self-expanding resilient permeable shell wherein a ratio of the total cross-sectional area of small filaments to the total cross-sectional area of large filaments is between 0.56 and 1.89. U.S. patent application 20200281603 (Marchand et al., Sep. 10, 2020, "Filamentary Devices for Treatment of Vascular Defects") discloses a permeable shell with a swellable polymer.

U.S. patent application 20210052278 (Mauger, Feb. 25, 2021, "Vascular Occlusion Devices Utilizing Thin Film Nitinol Foils") discloses an occlusion device with a support structure and a mesh component. U.S. patent application 20200163677 (Mayer et al., May 28, 2020, "Device for Restricting Blood Flow to Aneurysms") and U.S. patent Ser. No. 10/595,875 (Mayer et al., Mar. 24, 2020, "Device for Restricting Blood Flow to Aneurysms") disclose a blood-restricting device with a sequence of loops having a gradually decreasing diameter and being coaxial around a central axis. U.S. patent application 20190209181 (Mayer et al., Jul. 11, 2019, "Medical Device for Treating Vascular Malformations") discloses a non-occlusive device with a coilable section and a docking section.

U.S. patent Ser. No. 10/881,413 (Merritt et al., Jan. 5, 2021, "Systems and Methods for Embolization of Body Structures") discloses a self-expanding permeable shell with circumferentially-arrayed lobes. U.S. patent applications 20180271540 (Merritt et al., Sep. 27, 2018, "Systems and Methods for Embolization of Body Structures") and 20210169499 (Merritt et al., Jun. 10, 2021, "Systems and Methods for Embolization of Body Structures") disclose a self-expanding permeable shell with a plurality of circumferentially-arrayed lobes. U.S. patent application 20210007754 (Milhous et al., Jan. 14, 2021, "Filamentary Devices for Treatment of Vascular Defects") discloses inner and outer mesh balls. U.S. provisional patent application 62/873,256 (Milhous et al., Jul. 12, 2019, "Devices for Treatment of Vascular Defects") discloses a mesh of braided wires gathered into retention structures at proximal and distal ends.

U.S. patent application 20190254676 (Murphy et al., Aug. 22, 2019, "Vaso-Occlusive Device and Delivery Assembly") discloses a vaso-occlusive treatment system with a delivery assembly. U.S. patent application 20210129275 (Nguyen et al., May 6, 2021, "Devices, Systems, and Methods for Treating Aneurysms") discloses a method of everting a mesh such that the mesh encloses an open volume with a shape based, at least in part, on the shape of a forming assembly. U.S. patent application 20210128168 (Nguyen et al., May 6, 2021, "Systems and Methods for Treating Aneurysms") discloses a treatment system with an electrolytically corrodible conduit having a proximal portion, a distal portion, and a detachment zone between the proximal portion and the distal portion.

U.S. patent application 20210275779 (Northrop, Sep. 9, 2021, "Actuating Elements for Bending Medical Devices") discloses an elongated tube with an actuating element which bends the elongated tube. U.S. patent application 20160213380 (O'Brien, et al., Jul. 28, 2016, "Occlusion Device Having Spherical Secondary Shape and Mandrel for Forming Same") discloses a coil with a helical shape. U.S. patent applications 20210128167 (Patel et al., May 6, 2021, "Systems and Methods for Treating Aneurysms") and 20210128160 (Li et al., May 6, 2021, "Systems and Methods for Treating Aneurysms") disclose the use of an occlusive member (e.g., an expandable braid) in conjunction with an embolic element (e.g., coils, embolic material).

U.S. patent application 20200367900 (Pedroso et al., Nov. 26, 2020, "Layered Braided Aneurysm Treatment Device with Corrugations") discloses an implant with an open end, a pinched end, a predetermined shape, and corrugated folds. U.S. patent Ser. No. 11/058,431 (Pereira et al., Jul. 13, 2021, "Systems and Methods for Treating Aneurysms") discloses an occlusion element having a distal end, a proximal end, and a longitudinal axis extending between the distal end and the proximal end, the occlusion element configured to be delivered in a collapsed configuration and further configured to expand to an expanded configuration, and the occlusion element comprising an inverted mesh tube having an outer layer and an inner layer.

U.S. provisional patent application 62/307,123 (Plaza et al, Mar. 11, 2016, "Systems and Methods for Delivery of Stents and Stent-like Devices") appears to disclose an expanding aneurysm occlusion device which is implantable within the parent vessel of an aneurysm. U.S. patent application 20170258473 (Plaza et al., Sep. 14, 2017, "Systems and Methods for Delivery of Stents and Stent-Like Devices") and U.S. patent Ser. No. 10/952,739 (Plaza et al., Mar. 23, 2021, "Systems and Methods for Delivery of Stents and Stent-Like Devices") disclose an expandable elongate tubular member. U.S. patent application 20210275188 (Plaza et al., Sep. 9, 2021, "Systems and Methods for Delivery of Stents and Stent-Like Devices") discloses a system with an elongate tubular member having a lumen, an expandable stent, and a delivery device.

U.S. patent application 20200367901 (Porter et al., Nov. 26, 2020, "Embolic Devices and Methods of Manufacturing Same") discloses an embolic braid which is twisted between successive loops. U.S. patent application 20210052279 (Porter et al., Feb. 25, 2021, "Intra-Aneurysm Devices") discloses a device with an upper member that sits against the dome of an aneurysm, a lower member that sits in the neck of the aneurysm, and a means of adjusting the overall dimensions of the device. U.S. patent applications 20060155323 (Porter et al., Jul. 13, 2006, "Intra-Aneurysm Devices") and 20190298379 (Porter et al., Oct. 3, 2019, "Intra-Aneurysm Devices") and U.S. patent Ser. No. 10/265,075 (Porter et al., Apr. 23, 2019, "Intra-Aneurysm Devices") disclose a self-expanding resilient body having a linear configuration for deployment through a delivery catheter and an expanded substantially-spherical deployed configuration. U.S. patent application 20170189035 (Porter, Jul. 6, 2017, "Embolic Devices and Methods of Manufacturing Same") discloses a braid which is at least partially twisted between successive loops.

U.S. provisional patent application 62/819,296 (Rangwala et al, Mar. 15, 2019, "Occlusion") discloses an intrasaccular occlusive device with a more flexible distal section and a more stiff proximal section. U.S. patent application 20200289124 (Rangwala et al., Sep. 17, 2020, "Filamentary Devices for Treatment of Vascular Defects") discloses a permeable implant with a stiffer proximal portion near the neck of an aneurysm. U.S. patent application 20180092690 (Priya et al., Apr. 5, 2018, "Customized Endovascular Devices and Methods Pertaining Thereto") discloses patient-specific 3D complex coils and methods of making such coils, including custom fixtures for the manufacture of such coils. U.S. patent application 20210128165 (Pulugurtha et al., May 6, 2021, "Systems and Methods for Treating Aneurysms") discloses an occlusive member configured to be positioned within an aneurysm sac, and a distal conduit coupled to the occlusive member and having a first lumen extending therethrough.

U.S. patent application 20170079662 (Rhee et al., Mar. 23, 2017, "Occlusive Devices") discloses an aneurysm occlusion device comprising frame and mesh components, wherein the frame and mesh components have different porosity levels. U.S. patent application 20200038032 (Rhee et al., Feb. 6, 2020, "Occlusive Devices") discloses an implant with a frame and a mesh coupled to the frame. U.S. patent applications 20210128162 (Rhee et al., May 6, 2021, "Devices, Systems, and Methods for Treatment of Intracranial Aneurysms") and 20210153872 (Nguyen et al., May 27, 2021, "Devices, Systems, and Methods for Treatment of Intracranial Aneurysms") disclose delivering an occlusive member to an aneurysm cavity via an elongated shaft and transforming a shape of the occlusive member within the cavity and introducing an embolic element to a space between the occlusive member and an inner surface of the aneurysm wall.

U.S. patent application 20190209178 (Richter et al., Jul. 11, 2019, "Aneurysm Closure Device") discloses a device for aneurism exclusion with a plurality of self-expanding arms and panels attached to the arms. U.S. patent application 20210137715 (Ringwala et al., May 13, 2021, "Stent Delivery System and Method") discloses a method of delivering a stent which allows the porosity of the stent to be changed dynamically during delivery. U.S. patent application 20180303486 (Rosenbluth et al., Oct. 25, 2018, "Embolic Occlusion Device and Method") discloses an occlusion device including a tubular braided member with a repeating pattern of larger diameter portions and smaller diameter portions along a longitudinal axis. U.S. patent application 20210259699 (Rosenbluth et al., Aug. 26, 2021, "Embolic Occlusion Device and Method") discloses a tubular braid with a repeating pattern of larger and smaller diameter portions along its longitudinal axis.

U.S. patent application 20090287294 (Rosqueta et al., Nov. 19, 2009, "Braid-Ball Embolic Devices") discloses a braid with inner and outer layers which meet at a folded section at one end of the device and a hub at the other end of the device. U.S. patent application 20200138447 (Rosqueta et al., May 7, 2020, "Devices, Systems, and Methods for the Treatment of Vascular Defects") and U.S. patent Ser. No. 10/675,036 (Rosqueta et al., Jun. 9, 2020, "Devices, Systems, and Methods for the Treatment of Vascular Defects") disclose an occlusive device with a first mesh having an expanded state which curves about a first axis to form a first band and a second mesh having an expanded state which curves about a second axis different than the first axis to form a second band.

U.S. patent application 20160022445 (Ruvalcaba et al., Jan. 28, 2016, "Occlusive Device") and 20190343664 (Ruvalcaba et al., Nov. 14, 2019, "Occlusive Device") disclose an aneurysm embolization device can with a body having a single, continuous piece of material that is shape set into a plurality of distinct structural components and an atraumatic tip portion. U.S. patent Ser. No. 10/736,758 (Ruvalcaba et al., Aug. 11, 2020, "Occlusive Device") discloses an aneurysm embolization device with an expandable component and an atraumatic tip portion.

U.S. patent application 20020169473 (Sepetka et al., Nov. 14, 2002, "Devices and Methods for Treating Vascular Malformations") discloses a device for treating vascular malformations with a primary coil which provides resilience and secondary windings which fill interstitial spaces in the primary coil. U.S. patent application 20080281350 (Sepetka et al., Nov. 13, 2008, "Aneurysm Occlusion Devices") discloses an implantable occlusion device which moves between a compressed position before implantation and a generally concave or cup-shaped position after implantation. U.S. Pat. No. 8,597,320 (Sepetka et al., Dec. 3, 2013, "Devices and Methods for Treating Vascular Malformations") discloses a device with a closed mesh structure with a proximal collar and a distal collar, with flexible filaments extending therebetween. U.S. patent application 20190274691 (Sepetka et al., Sep. 12, 2019, "Occlusive Device") and U.S. patent Ser. No. 11/045,203 (Sepetka et al., Jun. 29, 2021, "Occlusive Device") disclose multiple sequentially deployed occlusive devices that are connected together to create an extended length. U.S. patent application 20210282784 (Sepetka et al., Sep. 16, 2021, "Occlusive Device") discloses an occlusion device with a braided occlusive portion and an embolic coil, wherein the braided occlusive portion extends into the embolic coil.

U.S. patent application 20170354418 (Teoh et al., Dec. 14, 2017, "Vaso-Occlusive Device Delivery System") discloses a vaso-occlusive device delivery assembly with a pusher assembly, a conductive sacrificial link, and a vaso-occlusive device secured to the pusher assembly by the sacrificial link. U.S. patent application 20210282789 (Vu et al., Sep. 16, 2021, "Multiple Layer Devices for Treatment of Vascular Defects") discloses a device with a first and second permeable shells, where the second shell sits within the first shell. U.S. patent Ser. No. 10/729,447 (Shimizu et al., Aug. 4, 2020, "Devices for Vascular Occlusion") discloses a wide variety of occlusive devices, delivery systems, and manufacturing methods for such devices. U.S. patent applications 20200375607 (Soto Del Valle et al., Dec. 3, 2020, "Aneurysm Device and Delivery System") and 20200397447 (Lorenzo et al., Dec. 24, 2020, "Aneurysm Device and Delivery System") disclose a mesh ball in a mesh bowl. U.S. patent application 20210251635 (Soto Del Valle et al., Aug. 19, 2021, "Intravascular Implant Deployment System") discloses a system for deploying an intrasaccular implant which includes a securing ring, a pusher, a securing wire, and a pull wire.

U.S. patent application 20170086851 (Wallace et al., Mar. 30, 2017, "Vaso-Occlusive Devices and Methods of Use") discloses expandable vaso-occlusive implants that include one or more soft and expandable braided members coupled to a pushable member such as a coil that maybe inserted and retrieved from within an aneurism using a delivery catheter. U.S. patent applications 20190201000 (Wallace et al., Jul. 4, 2019, "Vaso-Occlusive Devices") and 20210204955 (Wallace et al., Jul. 8, 2021, "Vaso-Occlusive Devices"), and also U.S. patent Ser. No. 10/925,612 (Wallace et al., Feb. 23, 2021, "Vaso-Occlusive Devices") disclose a vaso-occlusion system for occluding an aneurysm including a delivery catheter with a delivery lumen extending therethrough, a pusher member at least partially extending through the delivery lumen, and a vaso-occlusive device loaded within the delivery lumen.

U.S. patent Ser. No. 10/383,635 (Wallace et al., Aug. 20, 2019, "Vaso-Occlusive Devices and Methods of Use") and U.S. patent application 20190374228 (Wallace et al., Dec. 12, 2019, "Vaso-Occlusive Devices and Methods of Use") disclose vaso-occlusive implants that include one or more soft and expandable braided member coupled to a pushable member such as a coil. U.S. patent applications 20180250013 (Wallace et al., Sep. 6, 2018, "Vaso-Occlusive Devices Including a Friction Element") and 20200360025 (Wallace et al., Nov. 19, 2020, "Vaso-Occlusive Devices Including a Friction Element") disclose vaso-occlusive implants with one or more soft and expandable braided members coupled to a pushable member such as a coil.

U.S. patent application 20200187952 (Walsh et al., Jun. 18, 2020, "Intrasaccular Flow Diverter for Treating Cerebral Aneurysms") discloses implants with a stabilizing frame for anchoring and an occluding element for diverting blood flow from an aneurysm neck. U.S. patent application 20200405347 (Walzman, Dec. 31, 2020, "Mesh Cap for Ameliorating Outpouchings") discloses a self-expandable occluding device can both cover the neck of an outpouching and serve as a permanent embolic plug thereby immediately stabilizing the outpouching. U.S. patent application 20210022765 (Walzman, Jan. 28, 2021, "Coated Endovascular Intrasaccular Occlusion Device") discloses an endovascular treatment mesh device for closing outpouchings by affixing at least one hydrogel layer to a surface of an expandable body.

U.S. patent Ser. No. 10/398,441 (Warner et al., Sep. 3, 2019, "Vascular Occlusion") discloses a vascular disorder treatment system comprising a delivery tube, a containment device, a pusher distally movable through a lumen, and a stopper ring. U.S. patent application 20210045750 (Wolf et al., Feb. 18, 2021, "Systems and Methods for Treating Aneurysms") and U.S. patent Ser. No. 10/856,880 (Badruddin et al., Dec. 8, 2020, "Systems and Methods for Treating Aneurysms") discloses an implantable vaso-occlusive device with a proximal end configured to seat against the aneurysm adjacent the neck of the aneurysm and a distal end configured to extend in the sac and away from the neck of the aneurysm.

U.S. patent application 20200367906 (Xu et al., Nov. 26, 2020, "Aneurysm Treatment With Pushable Ball Segment") discloses a tubular braid that is set into a predetermined shape, compressed for delivery, and positioned based on the predetermined shape and the geometry of an aneurysm. U.S. patent application 20200367893 (Xu et al., Nov. 26, 2020, "Layered Braided Aneurysm Treatment Device") discloses an implant with two layers of tubular braid set into a predetermined shape. U.S. patent application 20210282786 (Zaidat et al., Sep. 16, 2021, "Systems and Methods for Treating Aneurysms") discloses an occlusion element with an inverted mesh tube having an outer layer and an inner layer, wherein the outer layer transitions to the inner layer at an inversion fold on its distal end.

SUMMARY OF THE INVENTION

Disclosed herein is a method for occluding a cerebral aneurysm including: delivering a flexible implant through a longitudinal lumen to a cerebral aneurysm, wherein the flexible implant has a compressed first configuration as it is delivered through the lumen; inserting the flexible implant into the aneurysm sac from the lumen, wherein the flexible implant self-expands into an expanded second configuration in the aneurysm sac; delivering embolic members and/or embolic material through an opening in the flexible implant into the interior of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, delivering a flexible implant can comprise delivering, advancing, pushing, and/or navigating the flexible implant. In an example, a flexible implant can be a net or mesh, braid, shell, liner, and/or stent. In an example, a longitudinal lumen for delivering a flexible implant can be a catheter and/or microcatheter. In an example, embolic members and/or embolic material which is inserted into a flexible implant can be embolic balls, embolic beads, embolic spheres, microsponges, hydrogels, other gelatinous particles, coils, polymer embolic strands, filaments, congealing embolic liquid or gel, and/or longitudinal "string-of-pearls" series of inter-connected embolic members. In an example, an opening through a flexible implant through which embolic members are inserted can comprise an opening, a hole, a ring, a cylinder, a lumen, and/or a valve. In an example, the interior of a flexible implant can be space inside a generally-globular, spherical, oblate spheroid, or ellipsoidal implant; space inside the convexity of a convex implant; and/or space inside the concavity of a concave flexible implant.

BRIEF INTRODUCTION TO THE FIGURES

Figure 2:
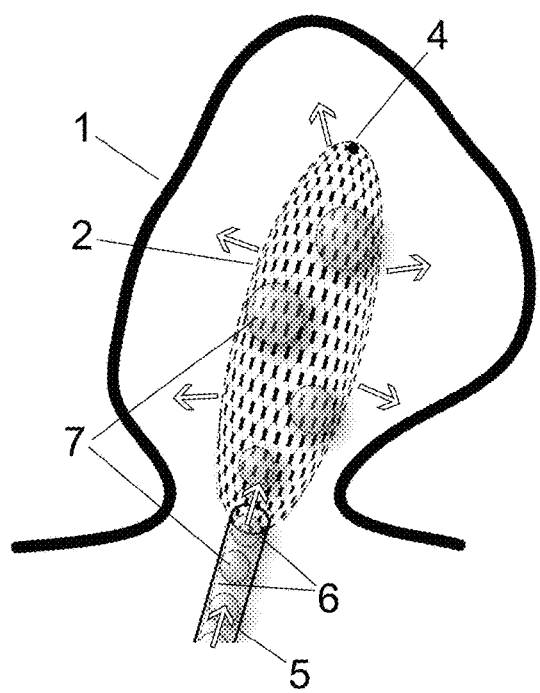
Figure 3:
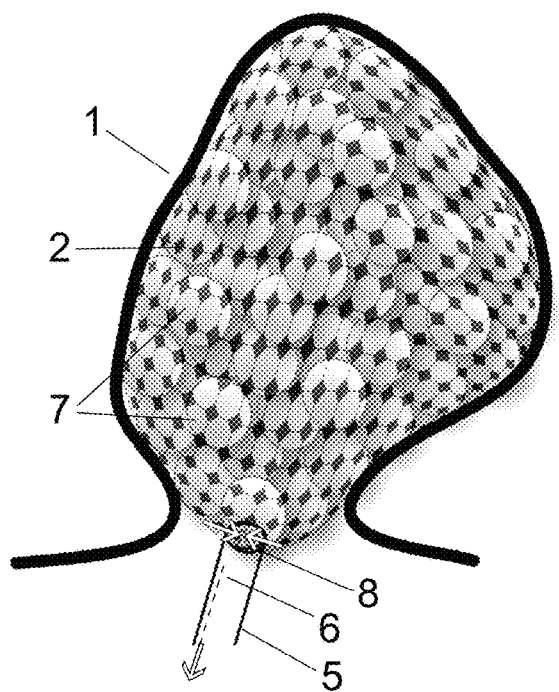
Figure 4:
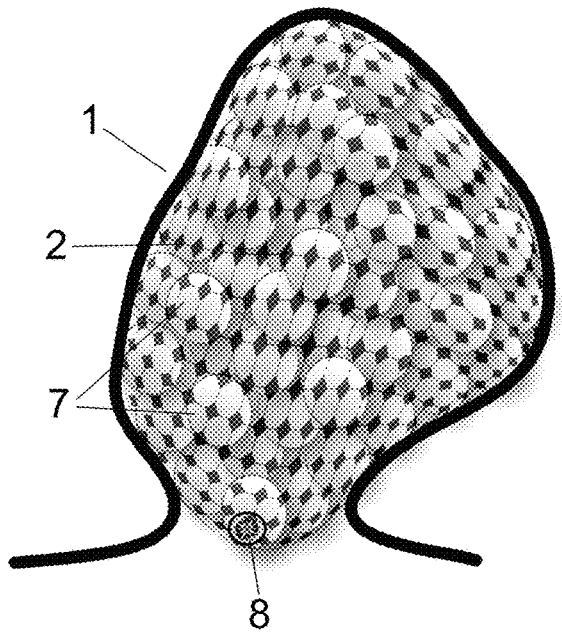

FIGS. 1 through 4 show four sequential views of a method and device for occluding an aneurysm which includes: delivering a flexible implant through a catheter into an aneurysm sac; and expanding the flexible implant within the sac by inserting embolic members and/or embolic material into the flexible implant so that the flexible implant expands to conform to the walls of the aneurysm sac.

DETAILED DESCRIPTION OF THE FIGURES

FIGS. 1 through 4 show four sequential views of deployment of an aneurysm occlusion device, illustrating a method for occluding a cerebral aneurysm. This method comprises: inserting a flexible net or mesh 2 into an aneurysm sac 1; and delivering embolic members and/or embolic material 7 into the flexible net or mesh, wherein accumulation of the embolic members and/or embolic material in the net or mesh causes the net or mesh to expand and occlude the aneurysm sac. This device and method also includes a catheter 5 by which the flexible net or mesh is inserted into the aneurysm sac, an opening 8 in the flexible net or mesh through which the embolic members and/or material is delivered into the flexible net or mesh, a closure mechanism 6 by which the opening is closed after embolic members have been delivered into the flexible net or mesh, and a wire 3 which moves a distal portion 4 of the flexible net or mesh. In an example, different regions of the flexible net or mesh can have different levels of strength, flexibility, plasticity, and/or elasticity.

In an example, a method for occluding a cerebral aneurysm can comprise: inserting a flexible, expandable, and liquid-permeable net or mesh into an aneurysm sac; introducing a plurality of soft and compressible fill members, using a liquid flow, into the net or mesh; and retaining the fill members within the net or mesh while allowing liquid flow to pass through the net or mesh such that a resulting accumulation of the plurality of fill members within the net or mesh causes the net or mesh to expand and to come into contact with and generally conform with the interior wall of the aneurysm sac to thereby substantially occlude the aneurysm and retain the net or mesh within the aneurysm sac.

In an example, a method for occluding a cerebral aneurysm can comprise: inserting a flexible net or mesh into an aneurysm sac; introducing embolic members and/or embolic material into the flexible net or mesh, such that the accumulation of the embolic members and/or embolic material within the flexible net or mesh causes the flexible net or mesh to expand and to come into contact with and generally conform with the interior wall of the aneurysm sac to thereby substantially occlude the aneurysm and retain the flexible net or mesh within the aneurysm sac.

In an example, a method for occluding a cerebral aneurysm can comprise: delivering a flexible net or mesh through a catheter to a cerebral aneurysm; inserting the flexible net or mesh into the aneurysm sac from the catheter; delivering embolic members and/or embolic material through an opening in the flexible net or mesh into the interior of the flexible net or mesh, wherein accumulation of embolic members and/or embolic material inside the flexible net or mesh causes the flexible net or mesh to expand and conform to the walls of the aneurysm sac; closing the opening through the flexible net or mesh; and detaching and withdrawing the lumen from the flexible net or mesh.

In an example, a method for occluding a cerebral aneurysm can comprise: delivering a flexible implant through a longitudinal lumen to a cerebral aneurysm, wherein the flexible implant has a compressed first configuration as it is delivered through the lumen; inserting the flexible implant into the aneurysm sac from the lumen, wherein the flexible implant self-expands into an expanded second configuration in the aneurysm sac; delivering embolic members and/or embolic material through an opening in the flexible implant into the interior of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, delivering a flexible implant can comprise delivering, advancing, pushing, and/or navigating the flexible implant. In an example, a flexible implant can be a net or mesh, braid, shell, liner, and/or stent. In an example, a longitudinal lumen for delivering a flexible implant can be a catheter and/or microcatheter. In an example, embolic members and/or embolic material which is inserted into a flexible implant can be embolic balls, embolic beads, embolic spheres, microsponges, hydrogels, other gelatinous particles, coils, polymer embolic strands, filaments, congealing embolic liquid or gel, and/or longitudinal "string-of-pearls" series of inter-connected embolic members. In an example, an opening through a flexible implant through which embolic members are inserted can comprise an opening, a hole, a ring, a cylinder, a lumen, and/or a valve. In an example, the interior of a flexible implant can be space inside a generally-globular, spherical, oblate spheroid, or ellipsoidal implant; space inside the convexity of a convex implant; and/or space inside the concavity of a concave flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible 3D-printed implant through a longitudinal lumen (e.g. a catheter) to a cerebral aneurysm, wherein the 3D-printed implant is a net or mesh with hexagonal pores and/or openings; wherein the flexible 3D-printed implant is in a radially-constrained first configuration as it is delivered through the lumen; inserting the flexible 3D-printed implant into the aneurysm sac from the lumen, wherein the flexible 3D-printed implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the flexible implant, wherein accumulation of embolic members and/or embolic material inside the flexible 3D-printed implant causes the flexible 3D-printed implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible 3D-printed implant through a longitudinal lumen (e.g. a catheter) to a cerebral aneurysm, wherein the 3D-printed implant is a net or mesh with triangular pores and/or openings; wherein the flexible 3D-printed implant is in a radially-constrained first configuration as it is delivered through the lumen; inserting the flexible 3D-printed implant into the aneurysm sac from the lumen, wherein the flexible 3D-printed implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the flexible implant, wherein accumulation of embolic members and/or embolic material inside the flexible 3D-printed implant causes the flexible 3D-printed implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible 3D-printed implant through a longitudinal lumen (e.g. a catheter) to a cerebral aneurysm, wherein the 3D-printed implant is a net or mesh with diamond-shaped pores and/or openings; wherein the flexible 3D-printed implant is in a radially-constrained first configuration as it is delivered through the lumen; inserting the flexible 3D-printed implant into the aneurysm sac from the lumen, wherein the flexible 3D-printed implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the flexible implant, wherein accumulation of embolic members and/or embolic material inside the flexible 3D-printed implant causes the flexible 3D-printed implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible 3D-printed implant through a longitudinal lumen (e.g. a catheter) to a cerebral aneurysm, wherein the proximal half of the implant is stiffer and/or less flexible than the distal half of the implant; wherein the flexible 3D-printed implant is in a radially-constrained first configuration as it is delivered through the lumen; inserting the flexible 3D-printed implant into the aneurysm sac from the lumen, wherein the flexible 3D-printed implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible 3D-printed implant into the interior (e.g. the space inside a concavity or convexity) of the flexible implant, wherein accumulation of embolic members and/or embolic material inside the flexible 3D-printed implant causes the flexible 3D-printed implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible 3D-printed implant through a longitudinal lumen (e.g. a catheter) to a cerebral aneurysm, wherein the proximal half of the implant is thicker than the distal half of the implant; wherein the flexible 3D-printed implant is in a radially-constrained first configuration as it is delivered through the lumen; inserting the flexible 3D-printed implant into the aneurysm sac from the lumen, wherein the flexible 3D-printed implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible 3D-printed implant into the interior (e.g. the space inside a concavity or convexity) of the flexible implant, wherein accumulation of embolic members and/or embolic material inside the flexible 3D-printed implant causes the flexible 3D-printed implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible 3D-printed implant through a longitudinal lumen (e.g. a catheter) to a cerebral aneurysm, wherein the distal half of the implant is more elastic than the proximal half of the implant; wherein the flexible 3D-printed implant is in a radially-constrained first configuration as it is delivered through the lumen; inserting the flexible 3D-printed implant into the aneurysm sac from the lumen, wherein the flexible 3D-printed implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible 3D-printed implant into the interior (e.g. the space inside a concavity or convexity) of the flexible implant, wherein accumulation of embolic members and/or embolic material inside the flexible 3D-printed implant causes the flexible 3D-printed implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a first implant (e.g. a braid, shell, and/or stent) and a second a second implant (e.g. a flexible net or mesh) through a longitudinal lumen (e.g. a catheter) into a cerebral aneurysm; wherein the first implant has a first stiffness level, the second implant has a second stiffness level, and the second stiffness level is less than the first stiffness level; and wherein the first implant self-expands into a second configuration which covers the aneurysm neck; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the second implant, wherein accumulation of embolic members and/or embolic material inside the second implant causes the second implant to expand and conform to the walls of the aneurysm sac; and detaching and withdrawing the lumen.

Alternatively, a method for occluding a cerebral aneurysm can comprise: delivering (e.g. delivering, advancing, and/or navigating) a first implant (e.g. a braid, shell, and/or stent) and a second a second implant (e.g. a flexible net or mesh) through a longitudinal lumen (e.g. a catheter) into a cerebral aneurysm; wherein the first implant has a first stiffness level, the second implant has a second stiffness level, and the second stiffness level is less than the first stiffness level; and wherein the first implant self-expands into a hemispherical and/or bowl-shaped configuration which covers the aneurysm neck; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the second implant, wherein accumulation of embolic members and/or embolic material inside the second implant causes the second implant to expand and conform to the walls of the aneurysm sac; and detaching and withdrawing the lumen.

In another example, a method for occluding a cerebral aneurysm can comprise: delivering (e.g. delivering, advancing, and/or navigating) a net or mesh through a longitudinal lumen (e.g. a catheter) to a cerebral aneurysm, wherein the net or mesh is radially-constrained as it is delivered through the lumen; inserting the net or mesh into the aneurysm sac from the lumen, wherein a stiff proximal region of the net or mesh self-expands over the neck of the aneurysm in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the net or mesh into the interior (e.g. the space inside a concavity or convexity) of the net or mesh, wherein accumulation of embolic members and/or embolic material inside the net or mesh causes a flexible distal region of the net or mesh to expand and conform to the walls of the aneurysm sac; closing the opening through the net or mesh; and detaching and withdrawing the lumen from the net or mesh.

In an example, a method for occluding a cerebral aneurysm can comprise: advancing an implant through a microcatheter to a cerebral aneurysm, wherein the implant is in a radially-constrained and longitudinally-elongated first configuration as it is delivered through the microcatheter; inserting the implant into the aneurysm sac, wherein the implant self-expands to radially-expanded and longitudinally-shortened second configuration in the aneurysm sac, wherein the proximal third of the implant is stiffer and/or less flexible than the distal third of the implant; and detaching and withdrawing the lumen from the implant. In an example, a method for occluding a cerebral aneurysm can comprise: advancing an implant through a microcatheter to a cerebral aneurysm, wherein the implant is in a radially-constrained and longitudinally-elongated first configuration as it is delivered through the microcatheter; inserting the implant into the aneurysm sac, wherein the implant self-expands to radially-expanded and longitudinally-shortened second configuration in the aneurysm sac, wherein the proximal half of the implant is stiffer and/or less flexible than the distal half of the implant; and detaching and withdrawing the lumen from the implant.

In one embodiment, a method for occluding a cerebral aneurysm can comprise: advancing an implant through a microcatheter to a cerebral aneurysm, wherein the implant is in a radially-constrained and longitudinally-elongated first configuration as it is delivered through the microcatheter; inserting the implant into the aneurysm sac, wherein the implant self-expands to radially-expanded and longitudinally-shortened second configuration in the aneurysm sac; and detaching and withdrawing the lumen from the implant.

In another example, a method for occluding a cerebral aneurysm can comprise: delivering (e.g. delivering, advancing, and/or navigating) an implant through a longitudinal lumen (e.g. a catheter) to a cerebral aneurysm, wherein the implant is radially-constrained as it is delivered through the lumen; inserting the implant into the aneurysm sac from the lumen, wherein a stiff proximal region of the implant self-expands over the neck of the aneurysm in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the implant into the interior (e.g. the space inside a concavity or convexity) of the implant, wherein accumulation of embolic members and/or embolic material inside the implant causes a flexible distal region of the implant to expand and conform to the walls of the aneurysm sac; closing the opening through the implant; and detaching and withdrawing the lumen from the implant.

In an example, a method for occluding a cerebral aneurysm can comprise: delivering (e.g. delivering, advancing, and/or navigating) an implant through a longitudinal lumen (e.g. a catheter) to a cerebral aneurysm, wherein the implant is radially-constrained as it is delivered through the lumen; inserting the implant into the aneurysm sac from the lumen, wherein a stiff proximal half of the implant self-expands over the neck of the aneurysm in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the implant into the interior (e.g. the space inside a concavity or convexity) of the implant, wherein accumulation of embolic members and/or embolic material inside the implant causes a flexible distal half of the implant to expand and conform to the walls of the aneurysm sac; closing the opening through the implant; and detaching and withdrawing the lumen from the implant.

In another example, a method for occluding a cerebral aneurysm can comprise: delivering (e.g. delivering, advancing, and/or navigating) a flexible shell through a longitudinal lumen (e.g. a catheter) to a cerebral aneurysm, wherein the flexible shell is in a radially-constrained first configuration as it is delivered through the lumen; inserting the flexible shell into the aneurysm sac from the lumen, wherein the flexible shell self-expands into a radially-expanded second configuration in the aneurysm sac, and wherein the proximal half of the flexible shell is stiffer and/or less flexible than the distal half of the shell; and detaching and withdrawing the lumen from the flexible shell.

In an example, a method for occluding a cerebral aneurysm can comprise: delivering (e.g. delivering, advancing, and/or navigating) a flexible net or mesh through a longitudinal lumen (e.g. a catheter) to a cerebral aneurysm, wherein the flexible net or mesh is in a radially-constrained first configuration as it is delivered through the lumen; inserting the flexible net or mesh into the aneurysm sac from the lumen, wherein the flexible net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible net or mesh into the interior (e.g. the space inside a concavity or convexity) of the flexible net or mesh, wherein accumulation of embolic members and/or embolic material inside the flexible net or mesh causes the flexible net or mesh to further expand into a third configuration in the aneurysm sac, wherein the third configuration is larger than the second configuration, and wherein the third configuration conforms to the walls of the aneurysm sac more closely than the second configuration; closing the opening through the flexible net or mesh; and detaching and withdrawing the lumen from the flexible net or mesh.

In an example, a method for occluding a cerebral aneurysm can comprise: delivering (e.g. delivering, advancing, and/or navigating) a flexible net or mesh through a longitudinal lumen (e.g. a catheter) to a cerebral aneurysm, wherein the flexible net or mesh is radially-constrained as it is delivered through the lumen; inserting the flexible net or mesh into the aneurysm sac from the lumen, wherein a proximal region of the flexible net or mesh self-expands over the neck of the aneurysm in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible net or mesh into the interior (e.g. the space inside a concavity or convexity) of the flexible net or mesh, wherein accumulation of embolic members and/or embolic material inside the flexible net or mesh causes a distal region of the flexible net or mesh to further expand and conform to the walls of the aneurysm sac; closing the opening through the flexible net or mesh; and detaching and withdrawing the lumen from the flexible net or mesh.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; using a flow of liquid to push embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; pushing embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen; expanding the flexible implant into a radially-expanded second configuration in the aneurysm sac by moving (e.g. pulling, pushing, or rotating) a wire attached to (a distal portion of) the flexible implant; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen; expanding the flexible implant into a radially-expanded second configuration in the aneurysm sac by transmitting electromagnetic energy to the flexible implant; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering string-of-pearls embolic strands through an opening (e.g. an opening, hole, ring, valve, and/or lumen) in the flexible implant into the interior (e.g. the space inside a concavity or convexity) of the flexible implant, wherein a string-of-pearls embolic strand is a plurality of embolic members (e.g. hydrogels, beads, spheres, sponges) which are pair-wise connected by longitudinal strands (e.g. filaments, cords, strings, cords, sutures, wires, or coils), wherein accumulation of string-of-pearls embolic strands inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering string-of-pearls embolic strands through an opening (e.g. an opening, hole, ring, valve, and/or lumen) in the flexible implant into the interior (e.g. the space inside a concavity or convexity) of the flexible implant, wherein a string-of-pearls embolic strand is a longitudinal series of embolic components (e.g. hydrogels, beads, spheres, sponges) which are inter-connected by longitudinal strands (e.g. filaments, cords, strings, cords, sutures, wires, or coils), wherein accumulation of string-of-pearls embolic strands inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering string-of-pearls embolic strands through an opening (e.g. an opening, hole, ring, valve, and/or lumen) in the flexible implant into the interior (e.g. the space inside a concavity or convexity) of the flexible implant, wherein accumulation of string-of-pearls embolic strands inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering polymer strands through an opening (e.g. an opening, hole, ring, valve, and/or lumen) in the flexible implant into the interior (e.g. the space inside a concavity or convexity) of the flexible implant, wherein accumulation of polymer strands inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering hydrogels or other gelatinous particles through an opening (e.g. an opening, hole, ring, valve, and/or lumen) in the flexible implant into the interior (e.g. the space inside a concavity or convexity) of the flexible implant, wherein accumulation of hydrogel or other gelatinous particles inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In one embodiment, a method for occluding a cerebral aneurysm can comprise: delivering a flexible implant through a longitudinal lumen to a cerebral aneurysm, wherein the flexible implant has a circumferentially-undulating first configuration as it is delivered through the lumen; inserting the flexible implant into the aneurysm sac from the lumen, wherein the flexible implant self-expands into an circumferentially-non-undulating configuration in the aneurysm sac; delivering embolic members and/or embolic material through an opening in the flexible implant into the interior of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

Alternatively, a method for occluding a cerebral aneurysm can comprise: delivering a flexible implant through a longitudinal lumen to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material through an opening in the flexible implant into the interior of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant. In an example, delivering can comprise delivering, advancing, and/or navigating.

In an example, a method for occluding a cerebral aneurysm can comprise: delivering a flexible implant through a longitudinal lumen to a cerebral aneurysm, wherein the flexible implant has a folded first configuration as it is delivered through the lumen; inserting the flexible implant into the aneurysm sac from the lumen, wherein the flexible implant self-expands into an unfolded configuration in the aneurysm sac; delivering embolic members and/or embolic material through an opening in the flexible implant into the interior of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a wound, coiled, and/or spiraled first configuration as it is delivered through the lumen; inserting the flexible implant into the aneurysm sac from the lumen, wherein the flexible implant unwinds, uncoils, and/or unspirals into an expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; and detaching and withdrawing the lumen from the flexible implant.

In an example, a method for occluding a cerebral aneurysm can comprise: delivering (e.g. delivering, advancing, and/or navigating) a braided flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, and wherein the average diameter of wires (or other longitudinal strands) in the proximal half of the flexible implant is greater than the average diameter of wires (or other longitudinal strands) in the distal half of the flexible; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a braided flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, and wherein the average density of wires (or other longitudinal strands) in the proximal half of the flexible implant is greater than the average density of wires (or other longitudinal strands) in the distal half of the flexible implant; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through a one-way valve into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through a leaflet valve into the interior (e.g. the space inside a concavity or convexity) of the flexible implant, wherein accumulation of embolic members and/or embolic material inside the flexible implant causes the flexible implant to further expand into a third configuration in the aneurysm sac; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a folded first configuration as it is delivered through the lumen; inserting the flexible implant into the aneurysm sac from the lumen, wherein the flexible implant unfolds into an expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration; and detaching and withdrawing the lumen from the flexible implant In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a spherical second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the aneurysm sac, wherein accumulation of embolic members and/or embolic material in the aneurysm sac compresses, folds, and/or inverts the flexible implant into a hemispherical third configuration; and detaching and withdrawing the lumen from the flexible implant.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant radially-expands into a spherical or ellipsoidal second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the aneurysm sac, wherein accumulation of embolic members and/or embolic material into the aneurysm sac causes the distal half of the flexible implant to compress, fold, and/or invert into a hemispherical and/or bowl-shaped third configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a generally globular, spherical, and/or ellipsoidal second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the aneurysm sac, wherein accumulation of embolic members and/or embolic material in the aneurysm sac causes the distal half of the flexible implant to compress, fold, and/or invert into a two-or-more-layer hemispherical and/or bowl-shaped third configuration; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a generally globular, spherical, and/or ellipsoidal second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the aneurysm sac, wherein accumulation of embolic members and/or embolic material in the aneurysm sac causes the distal half of the flexible implant to compress, fold, and/or invert into a two-or-more-layer hemispherical and/or bowl-shaped third configuration; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a compressed first configuration as it is delivered through the lumen; inserting the flexible implant into the aneurysm sac from the lumen, wherein the flexible implant expands into an expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the flexible implant, wherein accumulation of embolic members and/or embolic material inside the flexible implant causes the flexible implant to further expand into a third configuration in the aneurysm sac, and wherein the third configuration is larger than the second configuration; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a compressed first configuration as it is delivered through the lumen; inserting the flexible implant into the aneurysm sac from the lumen, wherein the flexible implant expands into an expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, and wherein the third configuration is larger than the second configuration; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a longitudinal axis which is substantially parallel to the longitudinal axis of the longitudinal lumen while it is being delivered through the lumen, wherein the flexible implant has a central lateral axis which bisects the longitudinal axis and is orthogonal to the longitudinal axis, and wherein the ratio of the length of the longitudinal axis to the length of the central lateral axis is greater than five in the first configuration; inserting the flexible implant into the aneurysm sac from the lumen, wherein the flexible implant self-expands into a second configuration in the aneurysm sac, and wherein the ratio is less than three in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a longitudinal axis which is substantially parallel to the longitudinal axis of the longitudinal lumen while it is being delivered through the lumen, wherein a central cross-sectional plane bisects the longitudinal axis and is orthogonal to the longitudinal axis, and wherein the perimeter of the central cross-sectional plane has a first length in the first configuration; inserting the flexible implant into the aneurysm sac from the lumen, wherein the flexible implant self-expands into a second configuration in the aneurysm sac, and wherein the perimeter of the central cross-sectional plane has a second length in the first configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the perimeter of the central cross-sectional plane has a third length in the third configuration, wherein the second length is greater than the first length, and wherein the third length is greater than the second length; closing the opening through the flexible implant; and detaching and withdrawing the lumen from the flexible implant.

In an example, a method for occluding a cerebral aneurysm can comprise: pushing a flexible implant (e.g. a flexible net, mesh, braid, shell, and/or stent) with a wire through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: pushing a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, and wherein the proximal half of the flexible implant is stiffer and/or less flexible than the distal half of the flexible implant; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm; inserting the flexible implant into the aneurysm sac from the lumen, wherein the proximal half of the flexible implant self-expands in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the distal half of the flexible implant to expand; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm; inserting the flexible implant into the aneurysm sac from the lumen, wherein the proximal half of the flexible implant self-expands in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the distal half of the flexible implant to expand; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm; inserting the flexible implant into the aneurysm sac from the lumen, wherein a proximal portion of the flexible implant self-expands in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the distal portion of the flexible implant to expand; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm; inserting the flexible implant into the aneurysm sac from the lumen, wherein a proximal portion of the flexible implant self-expands in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the distal portion of the flexible implant to expand; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) using fluid pressure through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a pleated first configuration as it is delivered through the lumen; inserting the flexible implant into the aneurysm sac from the lumen, wherein the flexible implant expands into an unpleated second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, wherein the flexible implant has a first maximum lateral diameter in the first configuration; inserting the flexible implant into the aneurysm sac from the lumen, wherein the flexible implant self-expands into a radially-expanded second configuration in the aneurysm sac, and wherein the flexible implant has a second maximum lateral diameter in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, wherein the flexible implant has a third maximum lateral diameter in the third configuration, wherein the second maximum lateral diameter is at least 50% greater than the first maximum lateral diameter, and wherein the third maximum lateral diameter is at least 50% greater than the second maximum lateral diameter; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, wherein the flexible implant has a first maximum lateral diameter in the first configuration; inserting the flexible implant into the aneurysm sac from the lumen, wherein the flexible implant self-expands into a radially-expanded second configuration in the aneurysm sac, and wherein the flexible implant has a second maximum lateral diameter in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, wherein the flexible implant has a third maximum lateral diameter in the third configuration, wherein the second maximum lateral diameter is at least 50% greater than the first maximum lateral diameter, and wherein the third maximum lateral diameter is at least 25% greater than the second maximum lateral diameter; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, wherein the flexible implant has a first maximum lateral diameter in the first configuration; inserting the flexible implant into the aneurysm sac from the lumen, wherein the flexible implant self-expands into a radially-expanded second configuration in the aneurysm sac, and wherein the flexible implant has a second maximum lateral diameter in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, wherein the flexible implant has a third maximum lateral diameter in the third configuration, wherein the second maximum lateral diameter is at least 50% greater than the first maximum lateral diameter, and wherein the third maximum lateral diameter is at least 10% greater than the second maximum lateral diameter; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, wherein the flexible implant has a first maximum lateral diameter in the first configuration; inserting the flexible implant into the aneurysm sac from the lumen, wherein the flexible implant self-expands into a radially-expanded second configuration in the aneurysm sac, and wherein the flexible implant has a second maximum lateral diameter in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, wherein the flexible implant has a third maximum lateral diameter in the third configuration, wherein the second maximum lateral diameter is at least 25% greater than the first maximum lateral diameter, and wherein the third maximum lateral diameter is at least 25% greater than the second maximum lateral diameter; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a spherical or ellipsoidal second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a non-spherical and non-ellipsoidal third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, and wherein a lateral cross-sectional perimeter of the flexible implant has a circular shape in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the lateral cross-sectional perimeter of the flexible implant has a non-circular (e.g. elliptical, pear-shaped, egg-shaped, and/or undulating) shape in the third configuration; closing the opening through the flexible implant; and detaching and withdrawing the lumen from the flexible implant.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) suspended in a liquid flow through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) via a liquid flow through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a first configuration whose lateral cross-sectional shape which is helical as it is delivered through the lumen; inserting the flexible implant into the aneurysm sac from the lumen, wherein the flexible implant self-expands into a second configuration whose lateral cross-sectional shape is not helical in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, wherein the flexible implant has a first number of undulations, bulges, and/or lobes in its second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, wherein the flexible implant has a second number of undulations, bulges, and/or lobes in its second configuration, and wherein the second number is greater than the first number; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, wherein the flexible implant has a first number of changes from concavity to convexity, or vice versa, around its perimeter in its second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the flexible implant has a second number of changes from concavity to convexity, or vice versa, around its perimeter in its third configuration, and wherein the second number is greater than the first number; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, and wherein the volume of the outer surface of the flexible implant fills a first percentage of the volume of the aneurysm sac in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the volume of the outer surface of the flexible implant fills a second percentage of the volume of the aneurysm sac in the second configuration, and wherein the second percentage is greater than the first percentage; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, and wherein the volume of the outer surface of the flexible implant fills a first percentage of the volume of the aneurysm sac in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the volume of the outer surface of the flexible implant fills a second percentage of the volume of the aneurysm sac in the second configuration, and wherein the first percentage is less than 90 percent and the second percentage is at least 90 percent; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, and wherein the volume of the outer surface of the flexible implant fills a first percentage of the volume of the aneurysm sac in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the volume of the outer surface of the flexible implant fills a second percentage of the volume of the aneurysm sac in the second configuration, and wherein the first percentage is less than 75 percent and the second percentage is at least 75 percent; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, and wherein the volume of the outer surface of the flexible implant fills a first percentage of the volume of the aneurysm sac in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the volume of the outer surface of the flexible implant fills a second percentage of the volume of the aneurysm sac in the second configuration, and wherein the second percentage is at least 5 percentage points greater than the first percentage; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, and wherein the volume of the outer surface of the flexible implant fills a first percentage of the volume of the aneurysm sac in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the volume of the outer surface of the flexible implant fills a second percentage of the volume of the aneurysm sac in the second configuration, and wherein the second percentage is at least 25 percentage points greater than the first percentage; closing the opening through the flexible implant; and detaching and withdrawing the lumen from the flexible implant.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, and wherein the volume of the outer surface of the flexible implant fills a first percentage of the volume of the aneurysm sac in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the volume of the outer surface of the flexible implant fills a second percentage of the volume of the aneurysm sac in the second configuration, and wherein the second percentage is at least 10 percentage points greater than the first percentage; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, wherein the flexible implant has a first maximum lateral diameter in the first configuration; inserting the flexible implant into the aneurysm sac from the lumen, wherein the flexible implant expands into a radially-expanded second configuration in the aneurysm sac, and wherein the flexible implant has a second maximum lateral diameter in the second configuration; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the flexible implant has a third maximum lateral radius in the third configuration, wherein the second maximum lateral radius is greater than the first maximum lateral radius, and wherein the third maximum lateral radius is greater than the second maximum lateral radius; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a globular, spherical, ellipsoidal, or oblate-spheroidal second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a folded first configuration as it is delivered through the lumen; inserting the flexible implant into the aneurysm sac from the lumen, wherein the flexible implant unfolds into an expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant fills at least 50% of the interior volume of the flexible implant and causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant fills at least 75% of the interior volume of the flexible implant and causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant fills at least 90% of the interior volume of the flexible implant and causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained and longitudinally-extended first configuration as it is delivered through the lumen; inserting the flexible implant into the aneurysm sac from the lumen, wherein the flexible implant self-expands into a radially-expanded and longitudinally-shortened second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration; closing the opening through the flexible implant by the transmission of electromagnetic energy to the opening; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein a proximal portion of the implant is no more than 25% larger in the third configuration than in the second configuration, and wherein a distal portion of the implant is at least 50% larger in the third configuration than in the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein a proximal portion of the implant is no more than 25% larger in the third configuration than in the second configuration, and wherein a distal portion of the implant is at least 50% larger in the third configuration than in the second configuration; and detaching and withdrawing the lumen from the flexible implant.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein a proximal third of the implant is no more than 10% larger in the third configuration than in the second configuration, and wherein a distal third of the implant is at least 25% larger in the third configuration than in the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein a proximal third of the implant is no more than 10% larger in the third configuration than in the second configuration, and wherein a distal third of the implant is at least 25% larger in the third configuration than in the second configuration; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein expansion of the distal portion of the flexible implant from the second configuration to the third configuration is greater than expansion of the proximal portion of the flexible implant from the second configuration to the third configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein a proximal half of the implant is no more than 25% larger in the third configuration than in the second configuration, and wherein a distal half of the implant is at least 50% larger in the third configuration than in the second configuration; closing the opening through the flexible implant; and detaching and withdrawing the lumen from the flexible implant In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein a proximal half of the implant is no more than 10% larger in the third configuration than in the second configuration, and wherein a distal half of the implant is at least 25% larger in the third configuration than in the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein a proximal half of the implant is no more than 25% larger in the third configuration than in the second configuration, and wherein a distal half of the implant is at least 50% larger in the third configuration than in the second configuration; and detaching and withdrawing the lumen from the flexible implant In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein a proximal half of the implant is no more than 10% larger in the third configuration than in the second configuration, and wherein a distal half of the implant is at least 25% larger in the third configuration than in the second configuration; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen, and wherein the distal half of the flexible implant is less stiff and/or more flexible than the proximal half of the flexible implant; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a compressed first configuration as it is delivered through the lumen; inserting the flexible implant into the aneurysm sac from the lumen, wherein the flexible implant self-expands into an uncompressed second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the distal portion of the implant to expand further more than the proximal portion of the implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a compressed first configuration as it is delivered through the lumen; inserting the flexible implant into the aneurysm sac from the lumen, wherein the flexible implant self-expands into an uncompressed second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to expand, wherein the size of the distal portion of the flexible implant is greater in the third configuration than in the second configuration, and wherein the size of the proximal portion of the flexible implant is substantially the same in the second and third configurations; and detaching and withdrawing the lumen from the flexible implant.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a compressed first configuration as it is delivered through the lumen; inserting the flexible implant into the aneurysm sac from the lumen, wherein the flexible implant self-expands into an uncompressed second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to expand, wherein the size of the distal portion of the flexible implant is greater in the third configuration than in the second configuration; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a compressed first configuration as it is delivered through the lumen; inserting the flexible implant into the aneurysm sac from the lumen, wherein the flexible implant self-expands into an uncompressed second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to expand, wherein the size of the distal half of the flexible implant is more than 25% greater in the third configuration than in the second configuration, and wherein the size of the proximal half of the flexible implant is less than 25% greater in the third configuration than in the second configuration; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a compressed first configuration as it is delivered through the lumen; inserting the flexible implant into the aneurysm sac from the lumen, wherein the flexible implant self-expands into an uncompressed second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to expand, wherein the size of the distal half of the flexible implant is more than 10% greater in the third configuration than in the second configuration, and wherein the size of the proximal half of the flexible implant is less than 10% greater in the third configuration than in the second configuration; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein different regions of the flexible implant have different levels of strength and/or stiffness, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein a distal region of the flexible implant has a lower level of strength and/or stiffness than a proximal region of the flexible implant, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein different regions of the flexible implant have different levels of flexibility, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein a distal region of the flexible implant has a higher level of flexibility than a proximal region of the flexible implant, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein different regions of the flexible implant have different levels of plasticity and/or elasticity, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein a distal region of the flexible implant has a higher level of plasticity and/or elasticity than a proximal region of the flexible implant, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a convex (e.g. generally globular, spherical, ellipsoidal, barrel-shaped, apple shaped, egg shaped, or pair shaped) second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior space of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a compressed first configuration as it is delivered through the lumen; inserting the flexible implant into the aneurysm sac from the lumen, wherein the flexible implant self-expands into an uncompressed second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a coiled first configuration as it is delivered through the lumen; inserting the flexible implant into the aneurysm sac from the lumen, wherein the flexible implant uncoils into an expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration; and detaching and withdrawing the lumen from the flexible implant.

Alternatively, a method for occluding a cerebral aneurysm can comprise: advancing a flexible implant (e.g. a flexible net, mesh, braid, shell, and/or stent) through a catheter to a cerebral aneurysm, wherein the flexible implant is made from braided filaments, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant made from braided wires through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a single-layer hemispherical and/or bowl-shaped second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into a distal-facing concavity of the flexible implant; closing the opening through the flexible implant; and detaching and withdrawing the lumen from the flexible implant.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a multi-layer hemispherical and/or bowl-shaped second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into a distal-facing concavity of the flexible implant; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands in the aneurysm sac into a second configuration which is symmetric with respect to the implant's longitudinal axis; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material causes the flexible implant to further expand into a third configuration in the aneurysm sac which is asymmetric with respect to the implant's longitudinal axis; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a second configuration which is symmetric with respect to the implant's longitudinal axis; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration which may be asymmetric with respect to the implant's longitudinal axis so as to better fill an irregularly-shaped aneurysm; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic liquid or gel through an opening (e.g. an opening, hole, ring, valve, and/or lumen) in the flexible implant into the interior (e.g. the space inside a concavity or convexity) of the flexible implant, wherein accumulation of embolic liquid or gel inside the flexible implant causes the flexible implant to further expand into a third configuration in the aneurysm sac; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic liquid or gel through an opening (e.g. an opening, hole, ring, valve, and/or lumen) in the flexible implant into the interior (e.g. the space inside a concavity or convexity) of the flexible implant, wherein accumulation of embolic liquid or gel inside the flexible implant causes the flexible implant to further expand into a third configuration in the aneurysm sac, and wherein the embolic liquid or gel congeals in the flexible implant; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering embolic balls, beads, and/or microspheres through an opening (e.g. an opening, hole, ring, valve, and/or lumen) in the flexible implant into the interior (e.g. the space inside a concavity or convexity) of the flexible implant, wherein accumulation of balls, beads, and/or microspheres inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering coils, filaments, or strands through an opening (e.g. an opening, hole, ring, valve, and/or lumen) in the flexible implant into the interior (e.g. the space inside a concavity or convexity) of the flexible implant, wherein accumulation of coils, filaments, or strands inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a plurality of microsponges, in order of decreasing size, through an opening (e.g. an opening, hole, ring, valve, and/or lumen) in the flexible implant into the interior (e.g. the space inside a concavity or convexity) of the flexible implant, wherein accumulation of the mesh balls inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a plurality of hydrogel pieces, in order of decreasing size, through an opening (e.g. an opening, hole, ring, valve, and/or lumen) in the flexible implant into the interior (e.g. the space inside a concavity or convexity) of the flexible implant, wherein accumulation of the mesh balls inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a plurality of braided mesh balls, in order of decreasing size, through an opening (e.g. an opening, hole, ring, valve, and/or lumen) in the flexible implant into the interior (e.g. the space inside a concavity or convexity) of the flexible implant, wherein accumulation of the mesh balls inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a longitudinal series of hydrogel pieces connected by wires or strands through an opening (e.g. an opening, hole, ring, valve, and/or lumen) in the flexible implant into the interior (e.g. the space inside a concavity or convexity) of the flexible implant, wherein accumulation of the hydrogel components inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a longitudinal series of globular hydrogel pieces connected by wires or strands through an opening (e.g. an opening, hole, ring, valve, and/or lumen) in the flexible implant into the interior (e.g. the space inside a concavity or convexity) of the flexible implant, wherein accumulation of the hydrogel components inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a longitudinal series of braided mesh balls through an opening (e.g. an opening, hole, ring, valve, and/or lumen) in the flexible implant into the interior (e.g. the space inside a concavity or convexity) of the flexible implant, wherein accumulation of the mesh balls inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

Alternatively, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a longitudinal series of braided mesh balls connected by wires or strands through an opening (e.g. an opening, hole, ring, valve, and/or lumen) in the flexible implant into the interior (e.g. the space inside a concavity or convexity) of the flexible implant, wherein accumulation of the mesh balls inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a first plurality of embolic balls, beads, and/or microspheres of a first average size and then delivering a second plurality of embolic balls, beads, and/or microspheres of a second average size through an opening (e.g. an opening, hole, ring, valve, and/or lumen) in the flexible implant into the interior (e.g. the space inside a concavity or convexity) of the flexible implant, wherein the second average size is smaller than the first average size, wherein accumulation of the first and second pluralities of balls, beads, and/or microspheres inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a continuous polymer strand through an opening (e.g. an opening, hole, ring, valve, and/or lumen) in the flexible implant into the interior (e.g. the space inside a concavity or convexity) of the flexible implant, wherein accumulation of the continuous polymer strand inside the flexible implant causes the flexible implant to further expand into a third configuration in the aneurysm sac, wherein the third configuration is larger than the second configuration, and wherein the third configuration conforms to the walls of the aneurysm sac more closely than the second configuration; cutting the proximal end of the polymer strand; and detaching and withdrawing the lumen from the flexible implant.

In another example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac; delivering a continuous polymer strand into the interior (e.g. the space inside a concavity or convexity) of the flexible implant, wherein accumulation of the continuous polymer strand inside the flexible implant causes the flexible implant to further expand into a third configuration in the aneurysm sac, wherein the third configuration is larger than the second configuration; cutting the proximal end of the polymer strand; and detaching and withdrawing the lumen from the flexible implant.

In an example, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) to a cerebral aneurysm, wherein the flexible implant has a radially-constrained first configuration as it is delivered through the lumen; inserting the flexible implant into the aneurysm sac from the lumen, wherein the flexible implant self-expands into a radially-expanded second configuration in the aneurysm sac, and wherein the proximal half of the flexible implant is stiffer and/or less flexible than the distal half of the implant; and detaching and withdrawing the lumen from the flexible implant.

In an example, a method for occluding a cerebral aneurysm can comprise: delivering (e.g. delivering, advancing, and/or navigating) a flexible braid or shell through a longitudinal lumen (e.g. a catheter) to a cerebral aneurysm, wherein the flexible braid or shell is in a radially-constrained first configuration as it is delivered through the lumen; inserting the flexible braid or shell into the aneurysm sac from the lumen, wherein the flexible braid or shell self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible braid or shell into the interior (e.g. the space inside a concavity or convexity) of the flexible braid or shell, wherein accumulation of embolic members and/or embolic material inside the flexible braid or shell causes the flexible braid or shell to further expand into a third configuration in the aneurysm sac, wherein the third configuration is larger than the second configuration, and wherein the third configuration conforms to the walls of the aneurysm sac more closely than the second configuration; closing the opening through the flexible braid or shell; and detaching and withdrawing the lumen from the flexible braid or shell.

In one embodiment, a method for occluding a cerebral aneurysm can comprise: delivering (e.g. delivering, advancing, and/or navigating) a flexible 3D-printed implant through a longitudinal lumen (e.g. a catheter) to a cerebral aneurysm, wherein the flexible 3D-printed implant is in a radially-constrained first configuration as it is delivered through the lumen; inserting the flexible 3D-printed implant into the aneurysm sac from the lumen, wherein the flexible 3D-printed implant self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible 3D-printed implant into the interior (e.g. the space inside a concavity or convexity) of the flexible implant, wherein accumulation of embolic members and/or embolic material inside the flexible 3D-printed implant causes the flexible 3D-printed implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

In an example, a method for occluding a cerebral aneurysm can comprise: delivering (e.g. delivering, advancing, and/or navigating) a first implant (e.g. a braid, shell, and/or stent) through a longitudinal lumen (e.g. a catheter) to a cerebral aneurysm, wherein the first implant has a first stiffness level; inserting the first implant into the aneurysm sac, wherein the first implant self-expands into a second configuration which covers the aneurysm neck; delivering (e.g. delivering, advancing, and/or navigating) a second implant (e.g. a flexible net or mesh) through a longitudinal lumen (e.g. a catheter) to a cerebral aneurysm, wherein the second implant has a second stiffness level, and wherein the second stiffness level is less than the first stiffness level; inserting the second implant into the aneurysm sac through an opening in the first implant; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the interior (e.g. the space inside a concavity or convexity) of the second implant, wherein accumulation of embolic members and/or embolic material inside the second implant causes the second implant to expand and conform to the walls of the aneurysm sac; and detaching and withdrawing the lumen.

In an example, a method for occluding a cerebral aneurysm can comprise: advancing a braided shell through a catheter to a cerebral aneurysm, wherein the braided shell has a radially-constrained first configuration as it is delivered through the lumen; inserting the braided shell into the aneurysm sac from the lumen, wherein the braided shell self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the braided shell into the interior (e.g. the space inside a concavity or convexity) of the braided shell, wherein accumulation of embolic members and/or embolic material inside the braided shell causes the braided shell to further expand into a third configuration in the aneurysm sac, wherein the third configuration is larger than the second configuration, and wherein the third configuration conforms to the walls of the aneurysm sac more closely than the second configuration; closing the opening through the braided shell; and detaching and withdrawing the lumen from the braided shell.

In another example, a method for occluding a cerebral aneurysm can comprise: advancing a braided shell through a catheter to a cerebral aneurysm, wherein the proximal half of the braided shell is stiffer and/or less flexible than the distal half of the braided shell, wherein the braided shell has a radially-constrained first configuration as it is delivered through the lumen; inserting the braided shell into the aneurysm sac from the lumen, wherein the braided shell self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the braided shell into the interior (e.g. the space inside a concavity or convexity) of the braided shell, wherein accumulation of embolic members and/or embolic material inside the braided shell causes the braided shell to further expand into a third configuration in the aneurysm sac, wherein the third configuration is larger than the second configuration, and wherein the third configuration conforms to the walls of the aneurysm sac more closely than the second configuration; closing the opening through the braided shell; and detaching and withdrawing the lumen from the braided shell.

In an example, a method for occluding a cerebral aneurysm can comprise: advancing a braided shell through a catheter to a cerebral aneurysm, wherein different regions of the braided shell have different levels of strength, flexibility, plasticity, and/or elasticity, wherein the braided shell has a radially-constrained first configuration as it is delivered through the lumen; inserting the braided shell into the aneurysm sac from the lumen, wherein the braided shell self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the braided shell into the interior (e.g. the space inside a concavity or convexity) of the braided shell, wherein accumulation of embolic members and/or embolic material inside the braided shell causes the braided shell to further expand into a third configuration in the aneurysm sac, wherein the third configuration is larger than the second configuration, and wherein the third configuration conforms to the walls of the aneurysm sac more closely than the second configuration; closing the opening through the braided shell; and detaching and withdrawing the lumen from the braided shell.

In another example, a method for occluding a cerebral aneurysm can comprise: advancing a flexible net or mesh in a catheter into a cerebral aneurysm, wherein the flexible net or mesh further comprises a proximal portion and a distal portion; expanding the flexible net or mesh in the aneurysm sac; and withdrawing the catheter. In an example, a method for occluding a cerebral aneurysm can comprise: advancing a flexible net or mesh in a catheter into a cerebral aneurysm, wherein the flexible net or mesh further comprises a proximal convex portion and a distal convex portion; expanding the flexible net or mesh in the aneurysm sac; and withdrawing the catheter.

In one embodiment, a method for occluding a cerebral aneurysm can comprise: delivering (e.g. delivering, advancing, and/or navigating) a flexible implant (e.g. a flexible net, mesh, braid, shell, and/or stent) through a longitudinal lumen (e.g. a catheter) into a cerebral aneurysm, wherein the flexible implant has a radially-constrained first configuration as it is delivered through the lumen; expanding the flexible implant into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration; closing the opening through the flexible implant; and detaching and withdrawing the lumen from the flexible implant.

Alternatively, a method for occluding a cerebral aneurysm can comprise: advancing an implant in a catheter to a cerebral aneurysm, wherein the implant further comprises a proximal convex portion and a distal convex portion; deploying the implant in the aneurysm sac; and withdrawing the catheter. In an example, a method for occluding a cerebral aneurysm can comprise: advancing a flexible net or mesh in a catheter to a cerebral aneurysm, wherein the flexible net or mesh further comprises a proximal portion and a distal portion; deploying the flexible net or mesh in the aneurysm sac; and withdrawing the catheter. In another example, a method for occluding a cerebral aneurysm can comprise: advancing a flexible net or mesh in a catheter to a cerebral aneurysm, wherein the flexible net or mesh further comprises a proximal convex portion and a distal convex portion; deploying the flexible net or mesh in the aneurysm sac; and withdrawing the catheter.

In another example, a method for occluding a cerebral aneurysm can comprise: advancing a braided net or mesh in a radially-constrained first configuration through a catheter into a cerebral aneurysm, wherein the braided net or mesh further comprises a proximal portion and a distal portion, and wherein the braided net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the braided net or mesh, wherein accumulation of embolic members and/or embolic material inside the flexible braided net or mesh causes the flexible braided net or mesh to further expand into a third configuration in the aneurysm sac, wherein the third configuration is larger than the second configuration, and wherein the third configuration conforms to the walls of the aneurysm sac more closely than the second configuration; closing the opening through the flexible braided net or mesh; and withdrawing the catheter.

In an example, a method for occluding a cerebral aneurysm can comprise: advancing a braided net or mesh in a radially-constrained first configuration through a catheter into a cerebral aneurysm, wherein the braided net or mesh further comprises a proximal portion and a distal portion, wherein the proximal portion is stiffer and/or less flexible than the distal portion, and wherein the braided net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the braided net or mesh, wherein accumulation of embolic members and/or embolic material inside the flexible braided net or mesh causes the flexible braided net or mesh to further expand into a third configuration in the aneurysm sac, wherein the third configuration is larger than the second configuration, and wherein the third configuration conforms to the walls of the aneurysm sac more closely than the second configuration; closing the opening through the flexible braided net or mesh; and withdrawing the catheter.

In one embodiment, a method for occluding a cerebral aneurysm can comprise: advancing a braided net or mesh in a radially-constrained first configuration through a catheter into a cerebral aneurysm, wherein the braided net or mesh further comprises a proximal convex portion and a distal convex portion, and wherein the braided net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the braided net or mesh, wherein accumulation of embolic members and/or embolic material inside the flexible braided net or mesh causes the flexible braided net or mesh to further expand into a third configuration in the aneurysm sac, wherein the third configuration is larger than the second configuration, and wherein the third configuration conforms to the walls of the aneurysm sac more closely than the second configuration; closing the opening through the flexible braided net or mesh; and withdrawing the catheter.

In an example, a method for occluding a cerebral aneurysm can comprise: advancing a braided net or mesh in a radially-constrained first configuration through a catheter into a cerebral aneurysm, wherein the braided net or mesh further comprises a proximal convex portion and a distal convex portion, wherein the proximal convex portion is stiffer and/or less flexible than the distal convex portion, and wherein the braided net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the braided net or mesh, wherein accumulation of embolic members and/or embolic material inside the flexible braided net or mesh causes the flexible braided net or mesh to further expand into a third configuration in the aneurysm sac, wherein the third configuration is larger than the second configuration, and wherein the third configuration conforms to the walls of the aneurysm sac more closely than the second configuration; closing the opening through the flexible braided net or mesh; and withdrawing the catheter.

In an example, a method for occluding a cerebral aneurysm can comprise: advancing a braided net or mesh in a radially-constrained first configuration through a catheter into a cerebral aneurysm, wherein the braided net or mesh further comprises a proximal portion and a distal portion, and wherein the braided net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the braided net or mesh; and withdrawing the catheter.

In another example, a method for occluding a cerebral aneurysm can comprise: advancing a braided net or mesh in a radially-constrained first configuration through a catheter into a cerebral aneurysm, wherein the braided net or mesh further comprises a proximal convex portion and a distal convex portion, and wherein the braided net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the braided net or mesh; and withdrawing the catheter.

In an example, a method for occluding a cerebral aneurysm can comprise: advancing a flexible net or mesh in a radially-constrained first configuration through a catheter into a cerebral aneurysm, wherein the flexible net or mesh further comprises a proximal portion and a distal portion, and wherein the flexible net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the flexible net or mesh; and withdrawing the catheter.

In one embodiment, a method for occluding a cerebral aneurysm can comprise: advancing a flexible net or mesh in a radially-constrained first configuration through a catheter into a cerebral aneurysm, wherein the flexible net or mesh further comprises a proximal convex portion and a distal convex portion, and wherein the flexible net or mesh self-expands into a radially-expanded second configuration in the aneurysm sac; delivering embolic members and/or embolic material (e.g. embolic balls or beads, microsponges, hydrogel or other gelatinous particles, coils, filaments, embolic liquid or gel, string-of-pearls embolic strands, and/or polymer embolic strands) into the flexible net or mesh; and withdrawing the catheter.

In an example, a method for occluding a cerebral aneurysm can comprise: delivering (e.g. delivering, advancing, and/or navigating) a distal-to-proximal longitudinal series of mesh balls connected by wires (or strands) through a lumen into an aneurysm sac; and withdrawing the lumen from the aneurysm sac. In another example, a method for occluding a cerebral aneurysm can comprise: delivering (e.g. delivering, advancing, and/or navigating) a distal-to-proximal longitudinal series of mesh balls of increasing size which are connected by wires (or strands) through a lumen into an aneurysm sac; and withdrawing the lumen from the aneurysm sac. In another example, a method for occluding a cerebral aneurysm can comprise: delivering (e.g. delivering, advancing, and/or navigating) a distal-to-proximal longitudinal series of mesh balls of decreasing size which are connected by wires (or strands) through a lumen into an aneurysm sac; and withdrawing the lumen from the aneurysm sac. In another example, a method for occluding a cerebral aneurysm can comprise: delivering (e.g. delivering, advancing, and/or navigating) a distal-to-proximal longitudinal series of hydrogel balls connected by wires (or strands) through a lumen into an aneurysm sac; and withdrawing the lumen from the aneurysm sac.

Alternatively, a method for occluding a cerebral aneurysm can comprise: delivering (e.g. delivering, advancing, and/or navigating) a distal-to-proximal longitudinal series of hydrogel balls of increasing size which are connected by wires (or strands) through a lumen into an aneurysm sac; and withdrawing the lumen from the aneurysm sac. In another example, a method for occluding a cerebral aneurysm can comprise: delivering (e.g. delivering, advancing, and/or navigating) a distal-to-proximal longitudinal series of hydrogel balls of decreasing size which are connected by wires (or strands) through a lumen into an aneurysm sac; and withdrawing the lumen from the aneurysm sac.

In an example, a method for occluding a cerebral aneurysm can comprise: advancing a flexible net or mesh in a radially-constrained first configuration through a catheter into a cerebral aneurysm, wherein the flexible net or mesh further comprises a proximal portion and a distal portion, and wherein the flexible net or mesh self-expands into a radially-expanded second configuration in the aneurysm sac; and withdrawing the catheter. In an example, a method for occluding a cerebral aneurysm can comprise: advancing a flexible net or mesh in a radially-constrained first configuration through a catheter into a cerebral aneurysm, wherein the flexible net or mesh further comprises a proximal convex portion and a distal convex portion, and wherein the flexible net or mesh self-expands into a radially-expanded second configuration in the aneurysm sac; and withdrawing the catheter.

Alternatively, a method for occluding a cerebral aneurysm can comprise: advancing a flexible net or mesh in a catheter into a cerebral aneurysm, wherein the flexible net or mesh further comprises a proximal portion and a distal portion, and wherein the flexible net or mesh self-expands in the aneurysm sac; and withdrawing the catheter. In another example, a method for occluding a cerebral aneurysm can comprise: advancing a flexible net or mesh in a catheter into a cerebral aneurysm, wherein the flexible net or mesh further comprises a proximal convex portion and a distal convex portion, and wherein the flexible net or mesh self-expands in the aneurysm sac; and withdrawing the catheter.

In an example, a method for occluding a cerebral aneurysm can comprise: manufacturing a flexible implant (e.g. a flexible net, mesh, braid, shell, and/or stent), wherein the flexible implant is configured to be delivered in a compressed first configuration through a longitudinal lumen (e.g. a catheter) into a cerebral aneurysm, expanded into an uncompressed second configuration in the aneurysm sac; and manufacturing embolic members and/or embolic material (e.g. embolic balls or beads, microsponges, hydrogel or other gelatinous particles, coils, filaments, embolic liquid or gel, string-of-pearls embolic strands, and/or polymer embolic strands) which are configured to be delivered through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration.

In an example, a method for occluding a cerebral aneurysm can comprise: manufacturing a flexible implant (e.g. a flexible net, mesh, braid, shell, and/or stent) which is configured to be delivered through a longitudinal lumen (e.g. a catheter) into a cerebral aneurysm, wherein the flexible implant has a radially-constrained first configuration as it is delivered through the lumen, and wherein the flexible implant self-expands into a radially-expanded second configuration in the aneurysm sac; and manufacturing embolic members and/or embolic material (e.g. embolic balls or beads, microsponges, hydrogel or other gelatinous particles, coils, filaments, embolic liquid or gel, string-of-pearls embolic strands, and/or polymer embolic strands) which are configured to be delivered through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration, and wherein the third configuration conforms to the walls of the aneurysm sac more closely than the second configuration.

In an example, a method for occluding a cerebral aneurysm can comprise: forming a flexible implant (e.g. a flexible net, mesh, braid, shell, and/or stent), wherein the flexible implant is configured to be delivered in a compressed first configuration through a longitudinal lumen (e.g. a catheter) into a cerebral aneurysm, expanded into an uncompressed second configuration in the aneurysm sac; and forming embolic members and/or embolic material (e.g. embolic balls or beads, microsponges, hydrogel or other gelatinous particles, coils, filaments, embolic liquid or gel, string-of-pearls embolic strands, and/or polymer embolic strands) which are configured to be delivered through an opening (e.g. an opening, hole, ring, valve, and/or lumen) in the flexible implant into the interior (e.g. the space inside a concavity or convexity) of the flexible implant, wherein accumulation of embolic members and/or embolic material inside the flexible implant causes the flexible implant to further expand into a third configuration in the aneurysm sac, wherein the third configuration is larger than the second configuration.

In an example, a flexible implant enclosure can receive and retain a plurality of fill members. In an example, a resulting accumulation of the plurality of fill members within a flexible implant can cause a flexible implant to expand and to come into contact with and generally conform to an interior wall of an aneurysm sac. This can substantially occlude the aneurysm and retain the implant within the aneurysm. In an example, a flexible implant can have non-uniform tensile strength, flexibility, plasticity, or elasticity. In an example, a flexible implant can be stronger near one location and less strong but more flexible near another location.

A flexible implant need not be of uniform tensile strength, flexibility, plasticity, or elasticity. It can be more flexible at one or more locations. In an example, a flexible implant can comprise a high-flexibility distal portion and a low-flexibility proximal portion. In an example, a flexible implant can have a distal portion with a first level of flexibility and a proximal portion with a second level of flexibility, wherein the second level is less than the first level. In an example, a flexible implant can have a distal portion with a first level of elasticity and a proximal portion with a second level of elasticity, wherein the second level is less than the first level. In an example, the high-flexibility distal portion of a flexible implant can have an irregular expanded arcuate three-dimensional shape which conforms to the walls of an irregularly-shaped aneurysm sac, while the low-flexibility proximal portion prevents the expandable member from protruding out of the aneurysm sac.

In an example, a flexible implant can comprise a resilient compression-resistant proximal portion. In an example, a flexible implant can be selected from the group consisting of: net; mesh; lattice; balloon; bag; and liner. In an example, a flexible implant can have a shape selected from the group consisting of: apple shape; bowl shape; compress-sphere shape; cylinder; disk; doughnut shape; egg shape; ellipsoid; Frisbee™ shape; frustum; hourglass shape; oval; peanut shape; pear shape; pumpkin shape; ring shape; Saturn shape; sphere; tire shape; and torus. In an example, a flexible implant can have an irregular expanded arcuate three-dimensional shape which conforms to the walls of an irregularly-shaped aneurysm sac.

In an example, a flexible implant can have a low-flexibility proximal portion and a high-flexibility distal portion. In an example, a resilient compression-resistant proximal portion of a flexible implant can further comprise a mesh, network, lattice, or radial array of wires or other stiff fibers. In an example, a resilient compression-resistant proximal portion of a flexible implant can be reinforced with wires or other stiff fibers in order to prevent the expandable member from lapsing out of the aneurysm sac.

In an example, a proximal portion of a flexible implant can comprise a resilient wider-than-neck portion with a first density level and a distal portion of this flexible implant can comprise a flexible sac-filling portion with a second density level, wherein the second level is less than the first level. In an example, the proximal portion of a flexible implant can comprise a resilient wider-than-neck portion with a first elasticity level and a distal portion of this flexible implant can comprise a flexible sac-filling portion with a second elasticity level, wherein the second level is greater than the first level. In an example, the proximal portion of a flexible implant can comprise a resilient wider-than-neck portion with a first flexibility level and a distal portion of this flexible implant can comprise a flexible sac-filling portion with a second flexibility level, wherein the second level is greater than the first level.

In an example, a flexible implant can be braided. In an example, different portions, segments, bulges, or undulations of a flexible implant can have different braid patterns. In an example, a proximal portion, segment, or undulation of a flexible implant can have a first braid pattern and a distal portion, segment, or undulation of this device can have a second braid pattern. In an example, different portions, segments, bulges, or undulations of a flexible implant can have different braid densities. In an example, a proximal portion, segment, or undulation of a flexible implant can have a higher braid density than a distal portion, segment, or undulation of this device. In an example, different portions, segments, bulges, or undulations of a flexible implant can have different braid angles. In an example, a proximal portion, segment, or undulation of a flexible implant can have a greater braid angle than a distal portion, segment, or undulation of this device.

In an example, different portions, segments, bulges, or undulations of a flexible implant can have different braid pitches. In an example, a proximal portion, segment, or undulation of a flexible implant can have a first braid pitch and a distal portion, segment, or undulation of this device can have a second braid pitch. In an example, different portions, segments, bulges, or undulations of a flexible implant can have different braid filament sizes. In an example, a proximal portion, segment, or undulation of a flexible implant can have a first braid filament size and a distal portion, segment, or undulation of this device can have a second braid filament size.

In an example, an intrasacular aneurysm occlusion device can comprise: a flexible implant which is inserted into and expanded within an aneurysm sac; wherein a flexible implant further can comprise a proximal portion whose centroid is a first distance from the aneurysm neck after expansion within the aneurysm sac; and wherein the proximal portion has a first average level of flexibility and a first average level of stiffness; wherein a flexible implant further can comprise a distal portion whose centroid is a second distance from the aneurysm neck after expansion within the aneurysm sac; wherein the distal portion has a second average level of flexibility and a second average level of stiffness; wherein the first distance is less than the second distance; wherein the first average level of flexibility is less than the second average level of flexibility and/or the first average level of stiffness is greater than the second average level of stiffness; an opening through the proximal portion of the flexible implant; embolic members and/or embolic material which is inserted through the opening into the flexible implant, wherein insertion of the embolic members and/or material into a flexible implant causes a flexible implant to expand and conform to the walls of even an irregularly-shaped aneurysm sac; and a closure mechanism which closes the opening after embolic members and/or material has been inserted through the opening into the flexible implant.

In an example, elasticity, stretchability, conformability, pliability, or softness can be substituted for flexibility as a measured characteristic of the proximal and distal portions of the implant. In an example, Young's Modulus, resiliency, strength, or durometer can be substituted for stiffness as a measured characteristic of the proximal and distal portions of the implant.

In an example, the stiffness of the proximal portion of the implant relative to that of the distal portion of the implant can be increased by using thicker wires, tubes, filaments, and/or strands for the proximal portion than those used for the distal portion. In an example, the stiffness of the proximal portion of the implant relative to that of the distal portion of the implant can be increased by using stiffer wires, tubes, filaments, and/or strands for the proximal portion than those used for the distal portion. In an example, the stiffness of the proximal portion of the implant relative to that of the distal portion of the implant can be increased by creating a greater density of wires, tubes, filaments, and/or strands in the proximal portion than in the distal portion.

In an example, the stiffness of the proximal portion of the implant relative to that of the distal portion of the implant can be increased by using a first proportion of metal relative to polymer to create the proximal portion and using a second proportion of metal relative to polymer to create the distal portion, wherein the second proportion is less than the first proportion. In an example, the stiffness of the proximal portion of the implant relative to that of the distal portion of the implant can be increased by adding radial spokes or struts to the proximal portion, wherein a radial array of wires, tubes, or struts extend radially-outward from a central area of the proximal portion of the implant.

In an example, the stiffness of the proximal portion of the implant relative to that of the distal portion can be increased by integrating an array of nested wire rings into the proximal portion. In an example, the stiffness of the proximal portion of the implant relative to that of the distal portion can be increased by integrating an undulating ring of wire into the proximal portion. In an example, the stiffness of the proximal portion of the implant relative to that of the distal portion can be increased by integrating a helical wire into the proximal portion of the implant.

In an example, the stiffness of the proximal portion of the implant relative to that of the distal portion can be increased by integrating one or more coils into the proximal portion of the implant. In an example, the stiffness of the proximal portion of the implant relative to that of the distal portion can be increased by coating wires, tubes, filaments, and/or strands in the proximal portion of the implant with a stiffening material. In an example, the stiffness of the proximal portion of the implant relative to that of the distal portion can be increased by using stiffer material, such as material with a higher Young's Modulus and/or durometer, to create the proximal portion than to create the distal portion.

In an example, the stiffness of the proximal portion of the implant relative to that of the distal portion of the implant can be increased by having a greater number of layers in the proximal portion than in the distal portion. In an example, a flexible implant can comprise a convex spherical, ellipsoidal, and/or generally-globular mesh at least partially within the concavity of a proximal concave mesh with a distal-facing concavity.

In an example, a flexible implant can comprise a convex spherical, ellipsoidal, and/or generally-globular mesh made primarily or entirely from a polymer and at least partially within the concavity of a proximal concave mesh with a distal-facing concavity made primarily or entirely from metal.

In an example, a flexible implant can be made by 3D printing. In an example, a flexible implant can be made by 3D printing with a flexible polymer, wherein the proximal portion of the implant is thicker than the distal portion of the implant. In an example, a flexible implant can be made by 3D printing with a flexible polymer, wherein the proximal portion of the implant is printed with a stiffer polymer than the distal portion of the implant.

In an example, a flexible implant can have a single-layer hemispherical and/or bowl-shaped first configuration which is formed by radially-constraining the proximal end of a tubular mesh with a ring, band, and/or cylinder. In an example, a flexible implant can have a double-layer hemispherical and/or bowl-shaped first configuration which formed by radially-constraining a mid-section of a tubular mesh and then everting a proximal portion of the tubular mesh over a distal portion of the tubular mesh. In an example, a flexible implant can have a double-layer hemispherical and/or bowl-shaped first configuration which is formed by radially-constraining the proximal end of a tubular mesh by a proximal annular member, radially-constraining the distal end of the tubular mesh by a distal annual member, and then inverting the distal portion of the tubular mesh into the concavity of the proximal portion of the tubular mesh. In an example, a flexible implant can have a double-layer hemispherical and/or bowl-shaped first configuration which is formed by radially-constraining both the proximal end and distal ends of a tubular mesh by a proximal member, thereby inverting the distal portion of the tubular mesh into the concavity of the proximal portion of the tubular mesh.

In an example, a proximal portion of a flexible implant can be made from one or more metals and a distal portion of a flexible implant can be made from one or more polymers. In an example, a proximal portion of a flexible implant can be made from Nitinol. In an example, a proximal portion of an implant can be a flexible metal mesh. In an example, a proximal portion of a flexible implant can be a braided metal mesh. In an example, a proximal portion of a flexible implant can be woven or braided from metal filaments, wires, or tubes. In an example, a proximal portion of a flexible implant can be made from shape-memory material.

In an example, a distal portion of a flexible implant can be made from a polymer. In an example, a distal portion of a flexible implant can be woven or braided from polymer threads, filaments, yarns, or strips. In an example, a distal portion of a flexible implant can be 3D printed. In an example, a distal portion of a flexible implant can be made from an elastic and/or stretchable polymer. In an example, a distal portion of a flexible implant can be elastic and/or stretchable and can expand as it is filled with embolic members and/or material. In an example, a distal portion of a flexible implant can be sufficiently flexible to conform to the shape of even an irregularly-shaped aneurysm sac as the implant is filled with embolic members and/or material. In an example, a distal portion of a flexible implant can be sufficiently flexible to conform to the shape of even an irregularly-shaped (e.g. non-spherical) aneurysm sac as the implant is filled with embolic members and/or material. In an example, a distal portion of a flexible implant can be made from one or more materials selected from the group consisting of: Dacron, elastin, hydroxy-terminated polycarbonate, methylcellulose, nylon, PDMS, polybutester, polycaprolactone, polyester, polyethylene terephthalate, polypropylene, polytetrafluoroethene, polytetrafluoroethylene, polyurethane, silicone, and silk.

Alternatively, both the proximal and distal portions of a flexible implant can be made from one or more metals. In an example, the proximal and distal portions of a flexible implant can be made from Nitinol. In an example, the proximal and distal portions can be flexible metal mesh. In an example, the proximal and distal portions of a flexible implant can be a braided metal mesh. In an example, the proximal and distal portions of a flexible implant can be woven or braided from metal filaments, wires, or tubes. In an example, the proximal and distal portions of a flexible implant can be made from shape-memory material.

Alternatively, both the proximal and distal portions of a flexible implant can be made from one or more polymers. In an example, the proximal and distal portions of a flexible implant can be woven or braided from polymer threads, filaments, yarns, or strips. In an example, the proximal and distal portions of a flexible implant can be 3D printed. In an example, the proximal and distal portions of a flexible implant can be made from an elastic and/or stretchable polymer. In an example, the proximal and distal portions of a flexible implant can be made from one or more materials selected from the group consisting of: Dacron, elastin, hydroxy-terminated polycarbonate, methylcellulose, nylon, PDMS, polybutester, polycaprolactone, polyester, polyethylene terephthalate, polypropylene, polytetrafluoroethene, polytetrafluoroethylene, polyurethane, silicone, and silk.

In an example, the proximal and/or distal portions of an implant can be made from polycarbonate urethane (PCU). In an example, the proximal and/or distal portions of an implant can be made from polydimethylsiloxane (PDMS). In an example, the proximal and/or distal portions of an implant can be made from polyesters. In an example, the proximal and/or distal portions of an implant can be made from polyether block amide (PEBA). In an example, the proximal and/or distal portions of an implant can be made from polyetherether ketone (PEEK). In an example, the proximal and/or distal portions of an implant can be made from polyethylene. In an example, the proximal and/or distal portions of an implant can be made from polyethylene glycol (PEG). In an example, the proximal and/or distal portions of an implant can be made from polyethylene terephthalate (PET).

In an example, the proximal and/or distal portions of an implant can be made from polyglycolic acid (PGA). In an example, the proximal and/or distal portions of an implant can be made from polylactic acid (PLA). In an example, the proximal and/or distal portions of an implant can be made from poly-N-acetylglucosamine (PNAG). In an example, the proximal and/or distal portions of an implant can be made from polyolefin. In an example, the proximal and/or distal portions of an implant can be made from polypropylene. In an example, the proximal and/or distal portions of an implant can be made from polytetrafluoroethylene (PTFE). In an example, the proximal and/or distal portions of an implant can be made from polyurethane (PU). In an example, the proximal and/or distal portions of an implant can be made from polyvinyl alcohol (PVA). In an example, the proximal and/or distal portions of an implant can be made from polyvinyl pyrrolidone (PVP).

In an example, pores or holes in a flexible implant can be smaller than the size (e.g. diameter, width, and/or length) of embolic members and/or material which is inserted into the implant so that the embolic members and/or material do not escape out of the implant. In an example, pores or holes in a flexible implant can less than half of the size (e.g. diameter, width, and/or length) of embolic members and/or material which is inserted into the implant so that the embolic members and/or material do not escape out of the implant. In an example, pores or holes in a flexible implant can have a size which is less than half of the smallest diameter and/or width of embolic members and/or material which is inserted into the implant so that the embolic members and/or material do not escape out of the implant. In an example, pores or holes in a flexible implant can have a size which less than half of the smallest length of embolic members and/or material which is inserted into the implant so that the embolic members and/or material do not escape out of the implant.

In an example, an implant can have hexagonal pores. In an example, an implant with hexagonal pores can be made using 3D printing. In an example, a flexible metal net or mesh with hexagonal pores can be made by 3D printing with liquid metal. In an example, an implant with hexagonal pores can be made by 3D printing with a polymer. In an example, an implant with hexagonal pores can be made by 3D printing with an elastomeric polymer. In an example, an implant with hexagonal pores can be made by 3D printing with a silicone-based polymer. In an example, an implant with hexagonal pores can be made by 3D printing with polydimethylsiloxane (PDMS).

In an example, an implant can have quadrilateral pores. In an example, an implant with quadrilateral pores can be made using 3D printing. In an example, a flexible metal net or mesh with quadrilateral pores can be made by 3D printing with liquid metal. In an example, an implant with quadrilateral pores can be made by 3D printing with a polymer. In an example, an implant with quadrilateral pores can be made by 3D printing with an elastomeric polymer. In an example, an implant with quadrilateral pores can be made by 3D printing with a silicone-based polymer. In an example, an implant with quadrilateral pores can be made by 3D printing with polydimethylsiloxane (PDMS).

In an example, an implant can have circular pores. In an example, an implant with circular pores can be made using 3D printing. In an example, a flexible metal net or mesh with circular pores can be made by 3D printing with liquid metal. In an example, an implant with circular pores can be made by 3D printing with a polymer. In an example, an implant with circular pores can be made by 3D printing with an elastomeric polymer. In an example, an implant with circular pores can be made by 3D printing with a silicone-based polymer. In an example, an implant with circular pores can be made by 3D printing with polydimethylsiloxane (PDMS).

In an example, an implant can be made with a cobalt chromium alloy. In an example, an implant can be made with a nickel-titanium alloy. In an example, an implant can comprise cobalt chromium alloy wires, filaments, or tubes. In an example, an implant can comprise nickel-titanium alloy wires, filaments, or tubes. In an example, an implant can comprise nitinol wires, filaments, or tubes. In an example, an implant can be made with nitinol. In an example, an implant can comprise platinum wires, filaments, or tubes. In an example, an implant can be made with platinum. In an example, an implant can comprise stainless steel wires, filaments, or tubes. In an example, an implant can comprise tantalum wires, filaments, or tubes. In an example, an implant can be made with tantalum.

In an example, a flexible implant can be folded and/or compressed as it is delivered through a catheter to an aneurysm sac. In an example, a flexible implant can have radial folds as it is delivered through a catheter to an aneurysm sac. In an example, a flexible implant can have longitudinal folds as it is delivered through a catheter to an aneurysm sac. In an example, a flexible implant can have cross-sectional folds as it is delivered through a catheter to an aneurysm sac.

In an example, an implant can be transformed into a single-layer ellipsoidal and/or generally globular flexible implant by two annular members which radially-constrain the proximal and distal ends of an implant. In an example, both of these radially-constrained ends can be inverted to project into the interior of flexible implant. In an example, the proximal end can be inverted to project into the interior of flexible implant and the distal end can remain outside the interior of the flexible implant. In an example, an implant is transformed into single-layer spherical flexible implant by two annular members which radially-constrain the proximal and distal ends of an implant.

In an example, bound and/or inverted ends of a flexible implant can both extend into the interior of a flexible implant in a spherical, ellipsoidal, and/or globular configuration. In an example, a distal bound and/or inverted end of a flexible implant can extend into the interior of a flexible implant in a spherical, ellipsoidal, and/or globular configuration and a proximal bound and/or inverted end of a flexible implant can extend outward from a flexible implant in a spherical, ellipsoidal, and/or globular configuration. In an example, a proximal bound and/or inverted end of a flexible implant can extend into the interior of a flexible implant in a spherical, ellipsoidal, and/or globular configuration and a distal bound and/or inverted end of a flexible implant can extend outward from a flexible implant in a spherical, ellipsoidal, and/or globular configuration.

In an example, a tubular mesh can be transformed into a single-layer, distally-concave, bowl-shaped flexible implant by a single annular member which radially-constrains the proximal end of a tubular mesh. In an example, a tubular mesh can be transformed into single-layer, proximally-concave, bowl-shaped flexible implant by a single annular member which radially-constrains the distal end of a tubular mesh.

In an example, a tubular mesh can be transformed into a double-layer, distally-concave, bowl-shaped flexible implant by two annular members which radially-constrain the proximal and distal ends of a tubular mesh, wherein the distal portion of a tubular mesh is inverted proximally (e.g. folded proximally) until it has a distally-concave shape. In an example, the distal circumference of a flexible implant is a fold in the implant. In an example, both of the radially-constrained ends can project into the interior of flexible implant. In an example, the proximal end can be inverted to project into the interior of bowl-shaped flexible implant and the distal end is not. Alternatively, a tubular mesh can be transformed into double-layer, distally-concave, bowl-shaped flexible implant by a single annular member in a middle section (between the ends) of a tubular mesh which radially-constrains the middle of a tubular mesh, wherein the proximal portion of a tubular mesh is everted distally until it has a distally-concave shape. In an example, the distal circumference of a flexible implant can comprise two nested tubular openings.

In an example, a tubular mesh from which a flexible implant is formed can be tapered. In an example, the distal end of a tubular mesh can have a smaller diameter than the proximal end of a tubular mesh. In an example, the distal end of a tubular mesh can have a larger diameter than the proximal end of a tubular mesh. In an example, a tubular mesh from which a flexible implant is formed can have differential flexibility. In an example the distal portion of a tubular mesh can have a first level of flexibility and the proximal portion of a tubular mesh can have a second level of flexibility, wherein the first level is less than the second level. In an example the distal portion of a tubular mesh can have a first level of flexibility and the proximal portion of a tubular mesh can have a second level of flexibility, wherein the first level is greater than the second level.

In an example, a tubular mesh from which a flexible implant is formed can have differential porosity. In an example the distal portion of a tubular mesh can have a first porosity level and the proximal portion of a tubular mesh can have a second porosity level, wherein the first level is less than the second level. In an example the distal portion of a tubular mesh can have a first porosity level and the proximal portion of a tubular mesh can have a second porosity level, wherein the first level is greater than the second level. In an example, a tubular mesh from which a flexible implant is formed can have differential durometer. In an example the distal portion of a tubular mesh can have a first durometer level and the proximal portion of a tubular mesh can have a second durometer level, wherein the first level is less than the second level. In an example the distal portion of a tubular mesh can have a first durometer level and the proximal portion of a tubular mesh can have a second durometer level, wherein the first level is greater than the second level.

In an example, the width of a flexible implant in a bowl-shaped configuration can be larger than the width of the aneurysm neck. In an example, the circumference of a flexible implant in a bowl-shaped configuration can be larger than the circumference of the aneurysm neck. In an example, the width of a flexible implant in a bowl-shaped configuration can be at least 10% larger than the width of the aneurysm neck. In an example, the circumference of a flexible implant in a bowl-shaped configuration can be at least 10% larger than the circumference of the aneurysm neck. In an example, the width of a flexible implant in a bowl-shaped configuration can be at least 90% of the maximum width of the aneurysm sac (parallel to the aneurysm neck). In an example, the circumference of a flexible implant in a bowl-shaped configuration can be at least 90% of the circumference of the maximum circumference of the aneurysm sac (parallel to the aneurysm neck). In an example, a flexible implant can function as a neck bridge, reducing or completely blocking blood flow from the parent vessel into the aneurysm sac.

In an example, a flexible implant formed from a tubular mesh can have a generally-hemispherical shape after a tubular mesh has been radially-constrained by one or more annular members. In an example, a flexible implant formed from a tubular mesh can have a generally globular and/or spherical shape after a tubular mesh has been radially-constrained by one or more annular members. In an example, a flexible implant formed from a tubular mesh can have an ellipsoidal or oval shape after a tubular mesh has been radially-constrained by one or more annular members. In an example, a flexible implant formed from a tubular mesh can have a disk shape after a tubular mesh has been radially-constrained by one or more annular members. In various examples, a flexible implant can have a post-expansion shape that is selected from the group consisting of spherical, ellipsoidal, toroidal, compressed-sphere shaped, egg shaped, Saturn shaped, hour-glass shaped, peanut shaped, beehive shaped and geodesic.

In an example, a flexible implant formed from a tubular mesh can have the shape of a paraboloid-of-revolution (e.g. a paraboloid revolved around a left or right vertical edge) after a tubular mesh has been radially-constrained by one or more annular members. In an example, a flexible implant formed from a tubular mesh can comprise a carlavian curve shape after a tubular mesh has been radially-constrained by one or more annular members. In an example, a flexible implant formed from a tubular mesh can have a toroidal shape after a tubular mesh has been radially-constrained by one or more annular members. In an example, a flexible implant formed from a tubular mesh can have a half-toroidal shape (e.g. a sliced bagel shape) after a tubular mesh has been radially-constrained by one or more annular members.

In an example, the distal end of a tubular mesh can be radially-constrained by a distal annular member and the proximal end of a tubular mesh can be radially-constrained by a proximal annular member to form a generally-globular, spherical, and/or ellipsoidal flexible implant which is inserted into an aneurysm sac. In an example, the distal end of a tubular mesh can be radially-constrained by a distal annular member and the proximal end of a tubular mesh can be radially-constrained by a proximal annular member to form a generally-globular, spherical, and/or ellipsoidal shape, wherein the distal portion is then inverted and/or folded to create a two-layer bowl-shaped flexible implant which is inserted into an aneurysm sac. In an example, both the distal end of a tubular mesh and the proximal end of a tubular mesh can be radially-constrained by a proximal annular member to form a two-layer bowl-shaped flexible implant which is inserted into an aneurysm sac.

In an example a flexible implant can be a two-layer bowl-shaped mesh with a distally-concave proximal layer and a distally-concave distal layer. In an example a flexible implant can be a two-layer bowl-shaped mesh with a distally-concave proximal layer and a distally-concave distal layer, wherein the distance between the proximal and distal layers is greater in a radially-central portion of a flexible implant than in radially-peripheral portions of the flexible implant. In an example a flexible implant can be a two-layer bowl-shaped mesh with a proximal layer and a distal layer, wherein the proximal layer has a uniform distal-facing concavity, but the distal layer has locally-concave and locally-convex portions. In an example, the radially-central portion of the distal layer is locally-convex and the radially-peripheral portions of the distal layer are locally-concave. In an example, the radially-central portion of the distal layer is less distally-concave than the radially-peripheral portions of the distal layer.

There are several material and structural factors which can affect the relative stiffness and flexibility of the proximal and distal portions, respectively, of a flexible implant. These factors can be selected, adjusted, and/or combined during the design and creation of a flexible implant in order to create the desired stiffness (or flexibility) of the proximal portion of a flexible implant relative to the flexibility (or stiffness) of the distal of the implant.

In an example, the stiffness of a proximal portion of the implant relative to that of a distal portion of the implant can be increased by using thicker wires, tubes, filaments, and/or strands for a proximal portion than those used for a distal portion. In an example, the stiffness of a proximal portion of the implant relative to that of a distal portion of the implant can be increased by using stiffer wires, tubes, filaments, and/or strands for a proximal portion than those used for a distal portion. In an example, the stiffness of a proximal portion of the implant relative to that of a distal portion of the implant can be increased by creating a greater density of wires, tubes, filaments, and/or strands in a proximal portion than in a distal portion. In an example, the stiffness of a proximal portion of the implant relative to that of a distal portion of the implant can be increased by using a first proportion of metal relative to polymer to create a proximal portion and using a second proportion of metal relative to polymer to create a distal portion, wherein the second proportion is less than the first proportion.

In an example, the stiffness of a proximal portion of the implant relative to that of a distal portion of the implant can be increased by adding radial spokes or struts to a proximal portion, wherein a radial array of wires, tubes, or struts extend radially-outward from a central area of a proximal portion of the implant. In an example, the stiffness of a proximal portion of the implant relative to that of a distal portion can be increased by integrating an array of nested wire rings into a proximal portion. In an example, the stiffness of a proximal portion of the implant relative to that of a distal portion can be increased by integrating an undulating ring of wire into a proximal portion. In an example, the stiffness of a proximal portion of the implant relative to that of a distal portion can be increased by integrating a helical wire into a proximal portion of the implant.

In an example, the stiffness of a proximal portion of the implant relative to that of a distal portion can be increased by integrating one or more coils into a proximal portion of the implant. In an example, the stiffness of a proximal portion of the implant relative to that of a distal portion can be increased by coating wires, tubes, filaments, and/or strands in a proximal portion of the implant with a stiffening material. In an example, the stiffness of a proximal portion of the implant relative to that of a distal portion can be increased by using stiffer material, such as material with a higher Young's Modulus and/or durometer, to create a proximal portion than to create a distal portion.

In an example, a flexible implant can be made by 3D printing. In an example, a flexible implant can be made by 3D printing with a flexible polymer, wherein a proximal portion of the implant is thicker than a distal portion of the implant. In an example, a flexible implant can be made by 3D printing with a flexible polymer, wherein a proximal portion of the implant is printed with a stiffer polymer than a distal portion of the implant.

In an example, the stiffness of a proximal portion of the implant relative to that of a distal portion of the implant can be increased by having a greater number of layers in a proximal portion than in a distal portion. In an example, a flexible implant can comprise a convex spherical, ellipsoidal, and/or generally-globular mesh at least partially within the concavity of a proximal concave mesh with a distal-facing concavity. In an example, a flexible implant can comprise a convex spherical, ellipsoidal, and/or generally-globular mesh made primarily or entirely from a polymer and at least partially within the concavity of a proximal concave mesh with a distal-facing concavity made primarily or entirely from metal.

In an example, the stiffness of a proximal portion of the implant can be increased by using thick wires, tubes, filaments, and/or strands in the proximal portion. In an example, the stiffness of a proximal portion of the implant can be increased by using stiff wires, tubes, filaments, and/or strands in the proximal portion. In an example, the stiffness of a proximal portion of the implant can be increased by creating a high density of wires, tubes, filaments, and/or strands in the proximal portion. In an example, the stiffness of a proximal portion of the implant can be increased by using a high proportion of metal relative to polymer to create the proximal portion.

In an example, the stiffness of a proximal portion of the implant can be increased by adding radial spokes or struts to a proximal portion of an implant, wherein a radial array of wires, tubes, or struts extend radially-outward from a central area of the proximal portion. In an example, the stiffness of a proximal portion of the implant can be increased by integrating an array of nested wire rings into a proximal portion. In an example, the stiffness of a proximal portion of the implant can be increased by integrating an undulating ring of wire into a proximal portion. In an example, the stiffness of a proximal portion of the implant can be increased by integrating a helical wire into a proximal portion of the implant.

In an example, the stiffness of a proximal portion of the implant can be increased by integrating one or more coils into a proximal portion of the implant. In an example, the stiffness of a proximal portion of the implant can be increased by coating wires, tubes, filaments, and/or strands in the proximal portion with a stiffening material. In an example, the stiffness of a proximal portion of the implant can be increased by using stiff material, such as material with a high Young's Modulus and/or durometer, to create the proximal portion. In an example, the stiffness of a proximal portion of the implant can be increased by having multiple layers (e.g. two or more layers) in the proximal portion.

In an example, the stiffness of a proximal portion of an implant relative to that of a distal portion of the implant can be increased by creating a greater number of layers (e.g. two or more mesh layers instead of one) for the proximal portion than for the distal portion. In an example, the stiffness of a proximal portion of an implant relative to that of the distal portion of the implant can be increased by adding a radial-spoke structure to the proximal portion, wherein a radial array of thicker wires, tubes, or struts extend radially outward from the center of the proximal portion of the implant. In an example, the stiffness of a proximal portion of an implant relative to that of the distal portion of the implant can be increased by integrating a radial-spoke wire structure into the proximal portion. In various examples, this can be done by adhesion, melting, weaving, or braiding. In an example, the stiffness of a proximal portion of an implant relative to that of the distal portion of an implant can be increased by coating wires, tubes, and/or strands in the proximal portion of the implant with a polymer coating.

In an example, the Young's modulus of (the material used to make) the distal portion of an implant can be between 1 and 5. In an example, the stiffness (or resiliency, strength, and/or durometer) of a proximal portion of an implant relative to that of a distal portion of the implant can be expressed as a percentage. In another example, the Young's modulus of (the material used to make) the distal portion of an implant can be between 0.005 and 0.01. In one embodiment, the Young's modulus of (the material used to make) the proximal portion of an implant can be greater than 0.1. In another example, the average flexibility of a proximal portion of an implant can be between 33% and 75% of the average flexibility of a distal portion of the implant. Alternatively, the stiffness of the proximal portion of an implant can be greater than 0.001 N/mm and the stiffness of the distal portion of an implant can be less than 0.001 N/mm. In an example, the Young's modulus of (the material used to make) the proximal portion of an implant can be between 1 and 10.

In another example, the Young's modulus of (the material used to make) the proximal portion of an implant can be between 0.005 and 0.01. In an example, the stiffness (or resiliency, strength, and/or durometer) of a distal portion of an implant relative to that of a proximal portion of the implant can be expressed as a percentage. Alternatively, the Young's modulus of (the material used to make) the proximal portion of an implant can be between 0.01 and 0.05. In an example, the Young's modulus of (the material used to make) the proximal portion of an implant can be greater than 1. Alternatively, the average stiffness of a distal portion of an implant can be between one-third and three-quarters that of a proximal portion of the implant. In an example, the stiffness of the proximal portion of an implant can be greater than 0.01 N/mm and the stiffness of the distal portion of an implant can be less than 0.005 N/mm.

In an example, the Young's modulus of (the material used to make) the proximal portion of an implant can be between 5 and 10. In an example, the average flexibility of a proximal portion of an implant can be between one-third and three-quarters that of a distal portion of the implant. In an example, the stiffness of the proximal portion of an implant can be greater than 0.005 N/mm and the stiffness of the distal portion of an implant can be less than 0.005 N/mm. In an example, the Young's modulus of (the material used to make) the proximal portion of an implant can be between 1 and 5. In one embodiment, the stiffness of the distal portion of an implant can be less than 0.025 N/mm. Alternatively, the Young's modulus of (the material used to make) the distal portion of an implant can be between 0.1 and 0.5.

In an example, the stiffness of a proximal portion of an implant relative to that of the distal portion can be increased by using a higher-density mesh for the proximal portion than for the distal portion. In an example, the stiffness of a proximal portion of an implant relative to that of the distal portion can be increased by adhering and/or melting a helical wire structure onto the proximal portion. In an example, the stiffness of a proximal portion of an implant relative to that of the distal portion can be increased by using material with a higher Young's modulus and/or durometer to create the proximal portion than for the distal portion.

In an example, the stiffness of the proximal portion of an implant can be greater than 0.1 N/mm and the stiffness of the distal portion of an implant can be less than 0.05 N/mm. In an example, the Young's modulus of (the material used to make) the proximal portion of an implant can be between 0.001 and 0.01. In an example, the Young's modulus of (the material used to make) the proximal portion of an implant can be greater than 0.01. In an example, the average flexibility of a distal portion of an implant can be at least 200% of average flexibility of a proximal portion of the implant. Alternatively, the stiffness of the distal portion of an implant can be less than 0.05 N/mm. In one embodiment, the Young's modulus of (the material used to make) the proximal portion of an implant can be between 0.1 and 0.5.

In an example, the average stiffness of a proximal portion of an implant can be at least 200% of the average stiffness of a distal portion of the implant. In one embodiment, the Young's modulus of (the material used to make) the proximal portion of an implant can be between 0.1 and 1. In an example, the Young's modulus of (the material used to make) the distal portion of an implant can be less than 0.1. Alternatively, the average stiffness of a proximal portion of an implant can be between 1.5 and 3 times that of a distal portion of the implant. In an example, the Young's modulus of (the material used to make) the distal portion of an implant can be between 0.1 and 1. In an example, the Young's modulus of (the material used to make) the distal portion of an implant can be less than 1.

In an example, the flexibility (or elasticity, stretchability, pliability, and/or softness) of a distal portion of an implant relative to that of a proximal portion of the implant can be expressed as a proportion, ratio, or fraction. In an example, the Young's modulus of (the material used to make) the distal portion of an implant can be between 0.01 and 0.05. Alternatively, the Young's modulus of (the material used to make) the proximal portion of an implant can be greater than 10. In an example, the average flexibility of a distal portion of an implant can be between 1.5 and 3 times that of a proximal portion of the implant. In one embodiment, the Young's modulus of (the material used to make) the distal portion of an implant can be between 0.5 and 1. In an example, the Young's modulus of (the material used to make) the distal portion of an implant can be less than 10.

In an example, the stiffness of a proximal portion of an implant relative to that of the distal portion can be increased by using a tighter braid or weave of wires, tubes, and/or strands to create the proximal portion than for the distal portion. In an example, the stiffness of a proximal portion of an implant relative to that of the distal portion can be increased by adding a "flower petals" shape configuration of structural elements (e.g. large-diameter wires) to the proximal portion of the implant. In an example, the stiffness of a proximal portion of an implant relative to that of the distal portion can be increased by having two layers in the proximal portion of the implant by radially constraining a middle section of a tubular mesh and inverting (or everting) a proximal portion of the implant to create a "ball in a bowl" configuration. In an example, the stiffness of a proximal portion of an implant relative to that of the distal portion can be increased by adding a hub-and-spoke configuration of radial structural elements (e.g. large wires) to the proximal portion of the implant. In an example, the stiffness of a proximal portion of an implant relative to that of the distal portion can be increased by integrating a hub-and-spoke wire structure with the proximal portion.

In an example, the average flexibility of a distal portion of an implant can be between 150% and 300% of the average flexibility of a proximal portion of the implant. Alternatively, the Young's modulus of (the material used to make) the proximal portion of an implant can be between 0.5 and 1. In an example, the Young's modulus of (the material used to make) the proximal portion of an implant can be greater than 0.5 and the Young's modulus of (the material used to make) the distal portion can be less than 0.5. Alternatively, the average stiffness of a proximal portion of an implant can be between 150% and 300% of the average stiffness of a distal portion of the implant. In an example, the Young's modulus of (the material used to make) the distal portion of an implant can be between 1 and 10. In an example, the Young's modulus of (the material used to make) the proximal portion of an implant can be greater than 1 and the Young's modulus of (the material used to make) the distal portion can be less than 1.

In another example, the average flexibility of a proximal portion of an implant can be less than half that of a distal portion of the implant. In one embodiment, the stiffness of the proximal portion of an implant can be greater than 0.025 N/mm and the stiffness of the distal portion of an implant can be less than 0.025 N/mm. In an example, the Young's modulus of (the material used to make) the proximal portion of an implant can be greater than 0.001. Alternatively, the average stiffness of a distal portion of an implant can be less than 50% of the average stiffness of a proximal portion of the implant. In another example, the stiffness of the proximal portion of an implant can be greater than 0.001 N/mm. In an example, the stiffness of the proximal portion of an implant can be greater than 0.025 N/mm and the stiffness of the distal portion of an implant can be less than 0.01 N/mm.

In an example, the flexibility (or elasticity, stretchability, pliability, and/or softness) of a proximal portion of an implant relative to that of a distal portion of the implant can be expressed as a proportion, ratio, or fraction. Alternatively, the stiffness of the distal portion of an implant can be less than 0.001 N/mm. In another example, the Young's modulus of (the material used to make) the distal portion of an implant can be between 0.01 and 0.1. In an example, the stiffness (or resiliency, strength, and/or durometer) of a proximal portion of an implant relative to that of a distal portion of the implant can be expressed as a proportion, ratio, or fraction. In another example, the stiffness of the distal portion of an implant can be less than 0.005 N/mm. In an example, the Young's modulus of (the material used to make) the proximal portion of an implant can be between 0.01 and 0.1.

In an example, the stiffness of a proximal portion of an implant relative to that of the distal portion can be increased by adhering and/or melting a hub-and-spoke wire structure onto the proximal portion. In an example, the stiffness of a proximal portion of an implant relative to that of the distal portion can be increased by using wider-diameter and/or thicker wires, tubes, and/or strands to create the proximal portion than for the distal portion. In an example, the stiffness of a proximal portion of an implant relative to that of the distal portion can be increased by adding a nested ring configuration (e.g. concentric circles) of radial structural elements (e.g. large wires) to the proximal portion of the implant. In an example, the stiffness of a proximal portion of an implant relative to that of the distal portion can be increased by integrating a nested wire rings (e.g. concentric wire rings) with the proximal portion. In an example, the stiffness of a proximal portion of an implant relative to that of the distal portion can be increased by adding a sinusoidal-circular configuration of structural elements (e.g. large wires) to the proximal portion of the implant.

In an example, the stiffness of a proximal portion of an implant relative to that of the distal portion can be increased by integrating an undulating circle of wire onto the proximal portion. In an example, the stiffness of a proximal portion of an implant relative to that of the distal portion can be increased by having two layers in the proximal portion of the implant and only one layer in the distal portion. In an example, the stiffness of a proximal portion of an implant relative to that of the distal portion can be increased by adding a helical (large-diameter wire) structure to the proximal portion of the implant. In an example, the stiffness of a proximal portion of an implant relative to that of the distal portion can be increased by increasing the wire density in the proximal portion of the implant.

In an example, a proximal portion of a flexible implant can be made by braiding or weaving metal wires, tubes, or filaments and a distal portion of the implant can be made by 3D printing with a flexible, elastic, and/or stretchable polymer. In an example, a flexible implant can be made by 3D printing with a flexible polymer, wherein the proximal portion of the printed 3D mesh is thicker than the distal portion of the printed 3D mesh. In an example, a flexible implant can be made by 3D printing with a flexible polymer, wherein the proximal portion of the printed 3D mesh is denser than the distal portion of the printed 3D mesh. In an example, a flexible implant can be made by 3D printing with a flexible polymer, wherein the proximal portion of the printed mesh is printed with a stiffer polymer than the distal portion of the printed mesh. In an example, a flexible implant can be made by 3D printing with a flexible polymer, wherein the proximal portion of the 3D printed mesh has more layers than the distal portion of the 3D printed mesh.

In an example, the stiffness of a proximal portion of an implant relative to that of the distal portion can be increased by having two layers in the proximal portion of the implant by radially constraining and inverting (or everting) a proximal portion of the implant. In an example, the stiffness of a proximal portion of an implant relative to that of the distal portion can be increased by adhering and/or melting a radial-spoke wire structure onto the proximal portion. In an example, the stiffness of a proximal portion of an implant relative to that of the distal portion can be increased by weaving and/or braiding additional large wires into the proximal portion. In an example, the stiffness of a proximal portion of an implant relative to that of the distal portion can be increased by adding a helical (large-diameter wire) coil to the proximal portion of the implant. In an example, the stiffness of a proximal portion of an implant relative to that of the distal portion can be increased by integrating a helical wire structure with the proximal portion.

In an example, the stiffness (or resiliency, strength, and/or durometer) of a distal portion of an implant relative to that of a proximal portion of the implant can be expressed as a proportion, ratio, or fraction. In an example, the average flexibility of a distal portion of an implant can be at least 2 times that of a proximal portion of the implant. In an example, the stiffness of the distal portion of an implant can be less than 0.01 N/mm. In an example, the Young's modulus of (the material used to make) the proximal portion of an implant can be between 0.05 and 0.1. In one embodiment, the average flexibility of a proximal portion of an implant can be less than 50% of the average flexibility of a distal portion of the implant. Alternatively, the stiffness of the proximal portion of an implant can be greater than 0.01 N/mm and the stiffness of the distal portion of an implant can be less than 01 N/mm.

In an example, the stiffness of a proximal portion of an implant relative to that of the distal portion can be increased by weaving and/or braiding radial spokes into the proximal portion. In an example, the stiffness of a proximal portion of an implant relative to that of the distal portion can be increased by adhering and/or melting nested wire rings (e.g. concentric wire rings) onto the proximal portion. In an example, the stiffness of a proximal portion of an implant relative to that of the distal portion can be increased by weaving and/or braiding thicker and/or wider-diameter wires, tubes, and/or strands into the mesh of the proximal portion, relative to that of the distal portion. In an example, the stiffness of a proximal portion of an implant relative to that of the distal portion can be increased by coating wires, tubes, and/or strands in the proximal portion of the implant with a stiffening material. In an example, the stiffness of a proximal portion of an implant relative to that of the distal portion can be increased by weaving and/or braiding wires, tubes, and/or strands with a higher Young's modulus and/or durometer into the mesh of the proximal portion, relative to that of the distal portion.

In an example, the stiffness of a proximal portion of an implant relative to that of the distal portion can be increased by having two layers in the proximal portion of the implant by radially constraining a middle section of a tubular mesh and inverting (or everting) a proximal portion of the implant. In an example, the stiffness of a proximal portion of an implant relative to that of the distal portion can be increased by having two layers in the proximal portion of the implant by radially constraining a middle section of the implant and inverting (or everting) a proximal portion of the implant. In an example, the stiffness of a proximal portion of an implant relative to that of the distal portion can be increased by adding large wires or tubes which radiate out from the proximal center of the implant on the proximal portion. In an example, the stiffness of a proximal portion of an implant relative to that of the distal portion can be increased by using a thicker layer of material to create the proximal portion than for the distal portion. In an example, the stiffness of a proximal portion of an implant relative to that of the distal portion can be increased by adding resilient structural elements (e.g. thick radial wires or tubes) to the proximal portion which are not in the distal portion.

In another example, the Young's modulus of (the material used to make) the distal portion of an implant can be between 5 and 10. In an example, the stiffness of the proximal portion of an implant can be greater than 0.01 N/mm. In another example, the stiffness of the proximal portion of an implant can be greater than 0.05 N/mm and the stiffness of the distal portion of an implant can be less than 0.05 N/mm. In one embodiment, the Young's modulus of (the material used to make) the proximal portion of an implant can be between 0.001 and 0.005. In an example, the average stiffness of a distal portion of an implant can be between 33% and 75% of the average stiffness of a proximal portion of the implant. Alternatively, the stiffness of the proximal portion of an implant can be greater than 0.005 N/mm and the stiffness of the distal portion of an implant can be less than 0.001 N/mm.

In an example, a flexible implant whose proximal portion is stiffer than its distal portion can be made by connecting a globular, elastic polymer mesh with a proximal bowl-shaped metal mesh. In an example, a flexible implant whose proximal portion is stiffer than its distal portion can be made by attaching a generally-globular flexible and elastic polymer mesh to a distal-facing concavity of proximal bowl-shaped metal mesh. In an example, a flexible implant can comprise a convex (e.g. spherical, ellipsoidal, and/or generally-globular) polymer mesh and a proximal concave (e.g. hemispherical and/or bowl-shaped) metal mesh. In an example, a flexible implant can be made by combining a convex (e.g. spherical, ellipsoidal, and/or generally-globular) polymer mesh and a proximal concave (e.g. hemispherical and/or bowl-shaped) metal mesh.

In an example, the Young's modulus of (the material used to make) the distal portion of an implant can be between 0.001 and 0.01. In an example, the average stiffness of a proximal portion of an implant can be at least 2 times that of a distal portion of the implant. Alternatively, the Young's modulus of (the material used to make) the distal portion of an implant can be between 0.05 and 0.1. In an example, the Young's modulus of (the material used to make) the distal portion of an implant can be less than 0.01. In another example, the flexibility (or elasticity, stretchability, pliability, and/or softness) of a proximal portion of an implant relative to that of a distal portion of the implant can be expressed as a percentage. In an example, the stiffness of the proximal portion of an implant can be greater than 0.05 N/mm.

In an example, the stiffness of a proximal portion of an implant relative to that of the distal portion can be increased by adding a star-burst configuration of radial structural elements (e.g. large wires) to the proximal portion of the implant. In an example, the stiffness of a proximal portion of an implant relative to that of the distal portion can be increased by integrating one or more coils into the proximal portion of the implant. In an example, the stiffness of a proximal portion of an implant relative to that of the distal portion can be increased by coating wires, tubes, and/or strands in the proximal portion of the implant with an expanding material. In an example, the stiffness of a proximal portion of an implant relative to that of the distal portion can be increased by coating wires, tubes, and/or strands in the proximal portion of the implant with hydrogel material. In an example, the stiffness of a proximal portion of an implant relative to that of the distal portion can be increased by coating wires, tubes, and/or strands in the proximal portion of the implant with a metal coating. In an example, the stiffness of a proximal portion of an implant relative to that of the distal portion can be increased by adhering and/or melting an undulating circle of wire onto the proximal portion (and it burns, burns, burns, the ring of wire, the ring of wire).

In an example, the average stiffness of a distal portion of an implant can be less than half that of a proximal portion of the implant. In one embodiment, the stiffness of the proximal portion of an implant can be greater than 0.005 N/mm. In an example, the stiffness of the proximal portion of an implant can be greater than 0.05 N/mm and the stiffness of the distal portion of an implant can be less than 0.025 N/mm. In another example, the Young's modulus of (the material used to make) the distal portion of an implant can be between 0.001 and 0.005. Alternatively, the flexibility (or elasticity, stretchability, pliability, and/or softness) of a distal portion of an implant relative to that of a proximal portion of the implant can be expressed as a percentage. In another example, the stiffness of the proximal portion of an implant can be greater than 0.025 N/mm.

In an example, an opening through a flexible implant through which embolic members and/or embolic material is inserted can be centrally located with respect to the proximal portion of the implant. In an example, an opening through a flexible implant through which embolic members and/or embolic material is inserted can be aligned with the longitudinal axis of the proximal portion of the implant. In an example, an opening through a flexible implant through which embolic members and/or embolic material is inserted can be connected to a catheter. In an example, an opening through a flexible implant through which embolic members and/or embolic material is inserted can be detachably connected to a catheter. In an example, an opening through a flexible implant through which embolic members and/or embolic material is inserted can be connected to a catheter, wherein this connection can be broken by application of electromagnetic energy.

In an example, an opening through a flexible implant through which embolic members and/or embolic material is inserted can be formed by an annular member. In an example, an opening through a flexible implant through which embolic members and/or embolic material is inserted can be formed by an annular member selected from the group consisting of a ring, band, cylinder, tube, or catheter. In an example, an opening through a flexible implant through which embolic members and/or embolic material is inserted can be formed by one or more rings, bands, cylinders, tubes, or catheters. In an example, an opening through a flexible implant through which embolic members and/or embolic material is inserted can be formed by two or more nested (e.g. concentric) rings, bands, cylinders, tubes, or catheters. In an example, annular members which form an opening through a flexible implant can be rings or bands which encircle the ends of the implant.

In an example, an annular member which forms an opening through a flexible implant can be a metal ring, band, or cylinder. In an example, an annular member which forms an opening through a flexible implant can be a polymer ring, band, or cylinder. In an example, an annular member which forms an opening through a flexible implant can be a wire, cord, or string. In an example, an annular member which forms an opening through a flexible implant can be a ring or band which encircles an implant, thereby radially-constraining and/or pinching an implant but allowing embolic members and/or embolic material to pass through it into the interior and/or a concavity of the flexible implant. In an example, an annular member which forms an opening through a flexible implant can be a cylinder which encircles an implant, thereby radially-constraining and/or pinching an implant but allowing embolic members and/or embolic material to pass through it into the interior and/or a concavity of the flexible implant.

In an example, an annular member which forms an opening through a flexible implant can be a cord or wire which encircles an implant, thereby radially-constraining and/or pinching an implant but allowing embolic members and/or embolic material to pass through it into the interior and/or a concavity of the flexible implant. In an example, an annular member which forms an opening through a flexible implant can be a catheter or tube around which an implant is attached, thereby radially-constraining and/or pinching an implant but allowing embolic members and/or embolic material to pass through it into the interior and/or a concavity of the flexible implant. In an example, an annular member which forms an opening through a flexible implant can be a lumen through a flexible implant through which embolic members and/or material is inserted into the flexible implant.

In an example, an implant can be soldered, melted, glued, or crimped onto an annular member which forms an opening through a flexible implant. In an example, an annular member which forms an opening through a flexible implant can have an inner ring and an outer ring, wherein an implant is fixed (e.g. soldered, melted, glued, or crimped) between the two rings. In an example, an annular member which forms an opening through a flexible implant can comprise an inner ring or cylinder and an outer elastic band, wherein an implant is held between the inner and outer portions. In an example, an annular member which forms an opening through a flexible implant can be centrally-located with respect to a proximal surface of the flexible implant. In an example, an annular member which forms an opening through a flexible implant can be centrally-located with respect to the longitudinal axis of the flexible implant. In an example, an annular member which forms an opening through a flexible implant can be a hub into which proximal ends of braided wires or tubes of the stent are bound or attached. In an example, an annular member which forms an opening through a flexible implant can be off-axial with respect to the longitudinal axis of the flexible implant.

In an example, an annular member which forms an opening through a flexible implant can comprise two nested and/or concentric (inner and outer) cylinders, wherein an implant is pinched and/or crimped between the two cylinders. In an example, an annular member which forms an opening through a flexible implant can comprise two nested and/or concentric (inner and outer) rings or bands, wherein an implant is pinched and/or crimped between the two rings or bands. In an example, an annular member which forms an opening through a flexible implant can comprise two nested and/or concentric (inner and outer) cylinders, wherein an implant is melted or glued between the two cylinders. In an example, an annular member which forms an opening through a flexible implant can comprise two nested and/or concentric (inner and outer) rings or bands, wherein an implant is melted or glued between the two rings or bands.

In an example, an annular member which forms an opening through a flexible implant can be a catheter which extends through the proximal surface of a flexible implant, wherein the catheter is detached and/or removed after embolic members and/or material has been inserted through the catheter into the interior or distal-facing concavity of the flexible implant. In an example, a distal portion of the catheter used to deliver embolic members and/or material can extend through the proximal surface of a flexible implant and be detached from the rest of the catheter after embolic members and/or material has been inserted through the catheter. In an example, an annular member which forms an opening through a flexible implant can be attached to a catheter during delivery of embolic members and/or material, and then detached (e.g. by the application of electromagnetic energy) from the catheter after delivery of the embolic members and/or material.

In an example, an annular member which forms an opening through a flexible implant can have an outer diameter which is between 5% and 20% of the diameter of an implant before an implant is radially constrained. In an example, an annular member which forms an opening through a flexible implant can have an outer diameter which is between 10% and 33% of the diameter of an implant before an implant is radially constrained. In an example, an annular member which forms an opening through a flexible implant can have an outer ring (or cylinder) with a first diameter and an inner ring (or cylinder) with a second diameter, wherein an implant is crimped or pinched between the outer ring (or cylinder) and inner ring (or cylinder), and wherein the first diameter is between 50% and 75% of the second diameter. In an example, an annular member which forms an opening through a flexible implant can have an outer ring (or cylinder) with a first diameter and an inner ring (or cylinder) with a second diameter, wherein an implant is crimped or pinched between the outer ring (or cylinder) and inner ring (or cylinder), and wherein the first diameter is between 66% and 90% of the second diameter.

In an example, an annular member which forms an opening through a flexible implant can comprise two nested rings, bands, or cylinders, wherein a section of an implant is inserted and held between the nested rings, bands, or cylinders. In an example, an annular member which forms an opening through a flexible implant can comprise an outer ring, band, or cylinder and an inner ring, band, or cylinder, wherein a section of an implant is inserted and held between them. In an example, an annular member which forms an opening through a flexible implant can comprise an outer ring, band, or cylinder and an inner ring, band, or cylinder, wherein one or both of the rings, bands, or cylinders are threaded. In an example, an annular member which forms an opening through a flexible implant can comprise an outer ring, band, or cylinder and an inner ring, band, or cylinder, wherein one or both of the rings, bands, or cylinders has a helical thread. In an example, an annular member which forms an opening through a flexible implant can comprise an outer ring, band, or cylinder and an inner ring, band, or cylinder, wherein one or both of the rings, bands, or cylinders has a helical thread to hold a section of an implant.

In an example, insertion of embolic members and/or material into an implant can cause the implant to expand and conform to the walls of even an irregularly-shaped aneurysm sac. In an example, an implant can self-expand to a first extent after being released from a catheter into an aneurysm sac and the implant can further expand, to a second extent, due to pressure from the accumulation of embolic members and/or embolic material inside the implant. In an example, an implant can further expand to conform to the wall contours of even an irregularly-shaped aneurysm sac.

In an example, embolic members and/or material which is inserted into an implant in an aneurysm sac can comprise one or more longitudinal metal coils. In an example, embolic members and/or material can comprise one or more longitudinal mesh ribbons. In an example, embolic members and/or material can comprise one or more longitudinal polymer strands. In an example, embolic members and/or material can comprise one or more string-of-pearls embolic strands, wherein a string-of-pearls embolic strand is a plurality of embolic beads or other embolic masses connected by a longitudinal wire, filament, string, cord, yarn, or thread. In an example, embolic members and/or material can comprise a plurality of hydrogel pieces or microsponges. In an example, embolic members and/or material can comprise liquid or gel which congeals after delivery into the implant.

In an example, embolic members and/or material which is inserted into the implant can be microspheres or microballs. In an example, embolic members and/or material inserted into the implant can be microsponges. In an example, embolic members and/or material inserted into the implant can be pieces of foam. In an example, embolic members and/or material inserted into the implant can be microbeads. In an example, embolic members and/or material inserted into the implant can be pieces of hydrogel. In an example, embolic members and/or material inserted into the implant can be metal embolic coils. In an example, embolic members and/or material inserted into the implant can be embolic ribbons. In an example, embolic members and/or material inserted into the implant can be yarns or filaments. In an example, embolic members and/or material can be polymer strands or coils. In an example, accumulation of embolic members and/or material in an aneurysm sac can compress an implant from a spherical, ellipsoidal, and/or globular configuration into a hemispherical, bowl-shaped, and/or distally-concave configuration by pressing against the distal surface of the implant.

In an example, embolic members and/or material inserted into the implant can be microspheres or microballs connected by a longitudinal wire, cord, and/or filament (e.g. in a "string-of-pearls" configuration). In an example, embolic members and/or material inserted into the implant can be microsponges connected by a longitudinal wire, cord, and/or filament (e.g. in a "string-of-pearls" configuration). In an example, embolic members and/or material inserted into the implant can be pieces of foam connected by a longitudinal wire, cord, and/or filament (e.g. in a "string-of-pearls" configuration). In an example, embolic members and/or material inserted into the implant can be microbeads connected by a longitudinal wire, cord, and/or filament (e.g. in a "string-of-pearls" configuration).

In an example, embolic members and/or material inserted into the implant can be pieces of hydrogel connected by a longitudinal wire, cord, and/or filament (e.g. in a "string-of-pearls" configuration). In an example, embolic members and/or material inserted into the implant can be embolic coils connected by a longitudinal wire, cord, and/or filament (e.g. in a "string-of-pearls" configuration). In an example, embolic members and/or material inserted into the implant can be embolic ribbons connected by a longitudinal wire, cord, and/or filament (e.g. in a "string-of-pearls" configuration). In an example, embolic members and/or material inserted into the implant can be yarns or filaments connected by a longitudinal wire, cord, and/or filament (e.g. in a "string-of-pearls" configuration).

In an example, embolic members and/or material inserted into the implant can be liquid which congeals and/or solidifies. In an example, embolic members and/or material inserted into the implant can be a polymer which congeals and/or solidifies. In an example, embolic members and/or material inserted into the implant can be a liquid embolic material. In an example, embolic members and/or material inserted into the implant can be hydrogel material. In an example, embolic members and/or material inserted into the implant can be congealing adhesive material. In an example, accumulation of embolic members and/or material in an aneurysm sac can compress an implant from a spherical, ellipsoidal, and/or globular configuration to a hemispherical, bowl-shaped, and/or distally-concave configuration by pressing against the distal surface of the implant.

In an example, embolic members and/or material which is inserted through an annular member into an implant can be one or more mesh ribbons. In an example, embolic members and/or material which is inserted through an annular member into an implant can be one or more wire mesh ribbons. In an example, embolic members and/or material which is inserted through an annular member into an implant can be one or more polymer mesh ribbons. In an example, embolic members and/or material which is inserted through an annular member into an implant can be one or more undulating and/or sinusoidal ribbons. In an example, embolic members and/or material which is inserted through an annular member into an implant can be one or more double-layer mesh ribbons.

In an example, embolic members and/or material can be made with a cobalt chromium alloy. In an example, embolic members and/or material can be made with a nickel-titanium alloy. In an example, embolic members and/or material can be cobalt chromium alloy coils or ribbons. In an example, embolic members and/or material can be nickel-titanium alloy coils or ribbons. In an example, embolic members and/or material can be nitinol coils or ribbons. In an example, embolic members and/or material can be made with nitinol. In an example, embolic members and/or material can be platinum coils or ribbons. In an example, embolic members and/or material can be made with platinum. In an example, embolic members and/or material can be stainless steel coils or ribbons. In an example, embolic members and/or material can be made with stainless steel. In an example, embolic members and/or material can be tantalum coils or ribbons. In an example, embolic members and/or material can be made with tantalum.

In an example, embolic members and/or material can be pushed through a catheter into an implant by a pusher wire and/or plug. In an example, liquid embolic material (which congeals after insertion into the implant) can be pushed through a catheter into an implant by fluid pressure. In an example, embolic members can be pushed into an implant by a flow of liquid (e.g. saline solution), wherein embolic members are retained in the implant and the saline solution escapes out of openings in the implant. In an example, embolic members and/or material can be pushed through a catheter into an implant by a conveyer belt mechanism. In an example, embolic members and/or material can be pushed through a catheter into an implant by a rotating helical delivery mechanism.

In an example, embolic members which are inserted into an implant can be embolic coils or ribbons. In an example, embolic members which are inserted into an implant can be pieces of foam or gel (such as hydrogel). In an example, embolic members which are inserted into an implant can be microballs or microspheres. In an example, embolic members which are inserted into an implant can be microsponges. In an example, embolic members which are inserted into an implant can be filaments or yarns. In an example, liquid embolic material can be inserted into an implant.

In an example, embolic members which are inserted into an implant can be selected from the group consisting of: pieces of gel; pieces of foam; and micro-sponges. In an example, embolic members which are inserted into an implant can be pieces of gel, such as hydrogel. In an example, embolic members which are inserted into an implant can be pieces of foam. In an example, embolic members which are inserted into an implant can be microsponges. In an example, embolic members which are inserted into an implant can be microscale gel balls. In an example, embolic members which are inserted into an implant can be microscale foam balls. In an example, embolic members which are inserted into an implant can be microscale sponge balls. In an example, embolic members which are inserted into an implant can be microscale gel polyhedrons. In an example, embolic members which are inserted into an implant can be microscale foam polyhedrons. In an example, embolic members which are inserted into an implant can be microscale sponge polyhedrons.

In an example, embolic members which are inserted into an implant can have generally spherical or globular shapes. In an example, embolic members which are inserted into an implant can have generally prolate spherical, ellipsoidal, or ovaloid shapes. In an example, embolic members which are inserted into an implant can have apple, barrel, or pair shapes. In an example, embolic members which are inserted into an implant can have torus or ring shapes. In an example, embolic members which are inserted into an implant can have disk or pancake shapes. In an example, embolic members which are inserted into an implant can have peanut or hour-glass shapes. In an example, embolic members which are inserted into an implant can be polyhedrons comprised of hexagonal surfaces. In an example, embolic members which are inserted into an implant can be polyhedrons comprised of quadrilateral surfaces. In an example, embolic members which are inserted into an implant can be polyhedrons comprised of triangular surfaces.

In an example, an embolic member can have a shape which is selected from the group consisting of: apple-shaped, barrel-shaped, bulbous, convex, ellipsoidal, globular, oblate spheroid, ovaloid, prolate-spheroid-shaped, spherical, and truncated-sphere-shaped. In an example, an embolic member can have a shape which is selected from the group consisting of: bowl-shaped, concave, hemispherical, and paraboloid of revolution. In an example, an embolic member can have a shape which is selected from the group consisting of: cubic, hexagon-shaped, hexahedron, octagon-shaped, octahedron, pentagonal-shaped, polyhedron-shaped, pyramidal, rectangular, square, and tetrahedronal.

In an example, embolic members which are inserted into an implant can have a (diameter) size within the range of 0.5 to 2 millimeters. In an example, embolic members which are inserted into an implant can have a (diameter) size within the range of 1 to 5 millimeters. In an example, embolic members which are inserted into an implant can have a (diameter) size within the range of 2 to 10 millimeters. In an example, embolic members which are inserted into an implant can have a (diameter) size within the range of 5 to 20 millimeters. In an example, embolic members which are inserted into an implant can have a (diameter) size within the range of 0.5 to 2 microns. In an example, embolic members which are inserted into an implant can have a (diameter) size within the range of 1 to 5 microns. In an example, embolic members which are inserted into an implant can have a (diameter) size within the range of 2 to 10 microns. In an example, embolic members which are inserted into an implant can have a (diameter) size within the range of 5 to 20 microns.

In an example, between 5 and 20 embolic members can be inserted into an implant. In an example, between 10 and 50 embolic members can be inserted into an implant. In an example, between 20 and 100 embolic members can be inserted into an implant. In an example, between 50 and 500 embolic members can be inserted into an implant.

In an example, embolic members which are inserted into an implant can expand in size within the implant. In an example, embolic members can have a first (average) size while being delivered to an aneurysm sac via a micro-catheter and a second (average) size after expansion within the aneurysm sac, wherein the second (average) size is 10% to 50% larger than the first (average) size. In an example, embolic members can have a first (average) size while being delivered to an aneurysm sac via a micro-catheter and a second (average) size after expansion within the aneurysm sac, wherein the second (average) size is 40% to 100% larger than the first (average) size. In an example, embolic members can have a first (average) size while being delivered to an aneurysm sac via a micro-catheter and a second (average) size after expansion within the aneurysm sac, wherein the second (average) size is more than twice the first (average) size.

In an example, embolic members can self-expand within an implant after they are released from a delivery catheter. In an example, embolic members can swell upon hydration from interaction with blood or other body fluid. In an example, embolic members can be expanded within the implant by one or more mechanisms selected from the group consisting of: expansion due to interaction with body fluid; expansion due to application of thermal energy; expansion due to exposure to a chemical agent; and expansion due to exposure to light energy. In an example, embolics can expand by a factor of 2-5 times. In an example, embolics can expand by a factor of 4-10 times. In an example, embolics can expand by a factor of more than 10 times. In an example, embolic members can expand to a sufficiently-large size that they cannot escape from the implant after insertion into the implant.

In an example, three-dimensional embolic members which are inserted into an implant can be soft and compressible. In an example, three-dimensional embolic members which are inserted into an implant can have a durometer less than 50. In an example, three-dimensional embolic members which are inserted into an implant can have an average durometer within the range of 10 to 30. In an example, three-dimensional embolic members which are inserted into an implant can have an average durometer within the range of 25 to 50. In an example, three-dimensional embolic members which are inserted into an implant can have an average durometer which is less than 70.

In an example, embolic members which are inserted into an implant can be made from a polymer. In an example, embolic members which are inserted into an implant can be made from an elastomeric polymer. In an example, embolic members which are inserted into an implant can be made from a silicone-based polymer. In an example, embolic members which are inserted into an implant can be made from polydimethylsiloxane (PDMS).

In an example, an embolic member can further comprise one or more layers made with different materials. In an example, an inner layer of an embolic member can be made from a first material and an outer layer of an embolic member can be made from a second material. In an example, an inner layer of an embolic member can be made from a first material with a first durometer and an outer layer of an embolic member can be made from a second material with a second durometer, wherein the second durometer is less than the first durometer. In an example, an embolic member can have an outer layer which is adhesive. In an example, an embolic member can have an outer layer with an adhesive property which is activated by application of electromagnetic and/or thermal energy. In an example, an embolic member can have an outer layer with an adhesive property which is activated by interaction with blood.

In an example, there can be a first average durometer of embolic members which are inserted into the implant at a first time and a second average durometer of embolic members which are inserted into the implant at a second time, wherein the second average durometer is greater than the first average durometer. In an example, there can be a first average durometer of embolic members which are inserted into the implant at a first time and a second average durometer of embolic members which are inserted into the implant at a second time, wherein the second average durometer is less than the first average durometer.

In an example, there can be a first average length of longitudinal strands between proximal pairs of embolic members which are inserted into an implant at a first time, a second average length of longitudinal strands between proximal pairs of embolic members which are inserted into the implant at a second time, and the second average length can be greater than the first average length. In an example, there can be a first average length of longitudinal strands between proximal pairs of embolic members which are inserted into an implant at a first time, a second average length of longitudinal strands between proximal pairs of embolic members which are inserted into the implant at a second time, and the second average length can be less than the first average length.

In an example, there can be a first set of embolic members which are inserted into an implant at a first time and a second set of embolic members which are inserted into the implant at a second time, wherein the second set of embolic members are closer together than the first set of embolic members. In an example, there can be a first set of embolic members which are inserted into an implant at a first time and a second set of embolic members which are inserted into the implant at a second time, wherein the first set of embolic members are closer together than the second set of embolic members. In an example, there can be a longitudinal series of embolic members connected by one or more longitudinal strands which is inserted into an implant within an aneurysm sac, wherein embolic members in the longitudinal series are progressively closer to each other moving along the length of the series in a distal to proximal manner. In an example, there can be a longitudinal series of embolic members connected by one or more longitudinal strands which is inserted into an implant within an aneurysm sac, wherein embolic members in the longitudinal series are progressively farther from each other moving along the length of the series in a distal to proximal manner.

In an example, embolic members which are inserted into the implant at a first time can have first shapes, embolic members which are inserted into the implant at a second time can have second shapes, and the second shape can be different than the first shape. In an example, embolic members which are inserted into the implant at a first time can be made with a first (combination of) material, embolic members which are inserted into the implant at a second time can be made with a second (combination of) material, and the second (combination of) material can be different from the first (combination of) material. In an example, embolic members which are inserted into the implant at a first time can be made with a first (combination of) material, embolic members which are inserted into the implant at a second time can be made with a second (combination of) material, and the second (combination of) material can be more flexible, elastic, and/or compliant than the first (combination of) material.

In an example, embolic members which are inserted into the implant at a first time can be made with a first (combination of) material, embolic members which are inserted into the implant at a second time can be made with a second (combination of) material, and the second (combination of) material can have a lower durometer than the first (combination of) material. In an example, embolic members which are inserted into the implant at a first time can be made with a first (combination of) material, embolic members which are inserted into the implant at a second time can be made with a second (combination of) material, and the second (combination of) material can be less flexible, elastic, and/or compliant than the first (combination of) material. In an example, embolic members which are inserted into the implant at a first time can be made with a first (combination of) material, embolic members which are inserted into the implant at a second time can be made with a second (combination of) material, and the second (combination of) material can have a higher durometer than the first (combination of) material.

In an example, there can be a first average size of embolic members which are inserted into the implant at a first time, a second average size of embolic members which are inserted into the implant at a second time, and the second average size can be greater than the first average size. In an example, there can be a first average size of embolic members which are inserted into the implant at a first time, a second average size of embolic members which are inserted into the implant at a second time, and the second average size can be less than the first average size.

In an example, an implant can be delivered into an aneurysm sac via a catheter and/or delivery tube. In an example, a plurality of embolic members can be delivered into the implant via the same catheter and/or delivery tube. In an example, an implant can be delivered into an aneurysm sac via a first catheter and/or delivery tube and a plurality of embolic members can be delivered into the implant via a second catheter and/or delivery tube.

In an example, embolic members can be made from ethylene vinyl alcohol (EVA). In an example, embolic members can be made from polyolefin. In an example, embolic members can be made from fibrinogen. In an example, embolic members can be made from polylactic acid (PLA). In an example, embolic members can be made from polyethylene terephthalate (PET). In an example, embolic members can be made from steel (e.g. stainless steel). In an example, embolic members can be made from methylcellulose.

In an example, embolic members can be made from acrylic. In an example, embolic members can be made from polyethylene glycol (PEG). In an example, embolic members can be made from silk. In an example, embolic members can be made from alginate. In an example, embolic members can be made from gold. In an example, embolic members can be made from polyethylene. In an example, embolic members can be made from tantalum. In an example, embolic members can be made from cobalt-chrome alloy (cobalt chromium).

In an example, embolic members can be made from polyetherether ketone (PEEK). In an example, embolic members can be made from thermoplastic elastomer. In an example, embolic members can be made from polycarbonate urethane (PCU). In an example, embolic members can be made from water-soluble synthetic polymer. In an example, embolic members can be made from collagen. In an example, embolic members can be made from polyvinyl alcohol (PVA).

In an example, embolic members can be made from titanium. In an example, embolic members can be made from polyether block amide (PEBA). In an example, embolic members can be made from radiopaque material. In an example, embolic members can be made from copolymer. In an example, embolic members can be made from polyvinyl pyrrolidone (PVP). In an example, embolic members can be made from polydimethylsiloxane (PDMS). In an example, embolic members can be made from zirconium-based alloy. In an example, embolic members can be made from polyesters. In an example, embolic members can be made from hydrogel. In an example, embolic members can be made from silicone. In an example, embolic members can be made from nitinol (or other nickel titanium alloy).

In an example, embolic members can be made from polyglycolic acid (PGA). In an example, embolic members can be made from small intestinal submucosa. In an example, embolic members can be made from nylon. In an example, embolic members can be made from polypropylene. In an example, embolic members can be made from platinum. In an example, embolic members can be made from polyurethane (PU). In an example, embolic members can be made from tungsten. In an example, embolic members can be made from fibrin.

In an example, embolic members can be made from poly-N-acetylglucosamine (PNAG). In an example, embolic members can be made from latex. In an example, embolic members can be made from fibronectin. In an example, embolic members can be made from palladium. In an example, embolic members can be made from polytetrafluoroethylene (PTFE). In an example, embolic members can be made from gelatin.

In an example, a selected quantity, series, length, and/or volume of embolic members can be selectively dispensed and/or detached into the implant in situ by a mechanism selected from the group consisting of: breaking a connection between embolic members in a series of embolic members; cutting a connection between embolic members in a series of embolic members (e.g. with a cutting edge or laser); dissolving a connection between embolic members in a series of embolic members (e.g. with thermal energy or a chemical); electrolytic mechanism; hydraulic mechanism; injecting a flow of embolic members suspended in a liquid or gel into an implant; melting a connection between embolic members in a series of embolic members (e.g. with thermal or light energy); progressing embolic members into an implant via a conveyor belt (e.g. chain-based conveyor); progressing embolic members into an implant via a helical conveyor (e.g. with an Archimedes' screw); pushing embolic members into an implant using the force of a liquid flow; pusher rod and/or plunger; release detachment mechanism; and thermal detachment mechanism.

In an example, embolic members can differ among themselves with respect to one or more characteristics selected from the group consisting of: porosity, shape, size, material, composition, coating, radiopacity, strength, stiffness, and type. In an example, a plurality of embolic members can be delivered into an implant in a linear (longitudinal) array or series of inter-connected embolic members. In an example, a plurality of embolic members can be delivered into an implant in a linear (longitudinal) array of connected embolic members, wherein this linear array can be cut, separated, and/or detached in situ (in a remote manner) at one or more selected locations by the user of the device in order to deliver a selected quantity, length, or volume or embolic members. In an example, a plurality of embolic members can be delivered into an implant in a planar array of inter-connected embolic members. In an example, a plurality of embolic members can be delivered into an implant in a three-dimensional array of inter-connected embolic members.

In an example, a series of embolic members can be delivered into an implant, wherein successive embolic members in the series are closer together. In an example, a series of embolic members can be delivered into an implant, wherein embolic members in the series are progressively closer together (as one progresses along the series in a distal to proximal manner). In an example, a series of embolic members can be delivered into an implant, wherein successive embolic members in the series are farther apart from each other. In an example, a series of embolic members can be delivered into an implant, wherein embolic members in the series are progressively farther apart (as one progresses along the series in a distal to proximal manner).

In an example, a series of embolic members can be delivered into an implant, wherein successive embolic members in the series decrease in durometer. In an example, a series of embolic members can be delivered into an implant, wherein embolic members in the series have progressively lower durometer values (as one progresses along the series in a distal to proximal manner). In an example, a series of embolic members can be delivered into an implant, wherein successive embolic members in the series increase in durometer. In an example, a series of embolic members can be delivered into an implant, wherein embolic members in the series have progressively higher durometer values (as one progresses along the series in a distal to proximal manner).

In an example, a series of embolic members can be delivered into an implant, wherein successive embolic members in the series are made of different materials. In an example, a series of embolic members can be delivered into an implant, wherein successive embolic members in the series are made of different materials, wherein these materials differ in porosity. In an example, a series of embolic members can be delivered into an implant, wherein successive embolic members in the series are made of different materials, wherein these materials differ in radiopacity. In an example, a series of embolic members can be delivered into an implant, wherein successive embolic members in the series are made of different materials, wherein these materials differ in stiffness. In an example, a series of embolic members can be delivered into an implant, wherein successive embolic members in the series are made of different materials, wherein these materials differ in durometer.

In an example, a series of embolic members can be delivered into an implant, wherein successive embolic members in the series decrease in porosity. In an example, a series of embolic members can be delivered into an implant, wherein embolic members in the series become progressively less porous (as one progresses along the series in a distal to proximal manner). In an example, a series of embolic members can be delivered into an implant, wherein successive embolic members in the series increase in porosity. In an example, a series of embolic members can be delivered into an implant, wherein embolic members in the series become progressively more porous (as one progresses along the series in a distal to proximal manner).

In an example, a series of embolic members can be delivered into an implant, wherein successive embolic members in the series differ in shape. In an example, a series of embolic members can be delivered into an implant, wherein successive embolic members in the series differ in their degree of convexity. In an example, a series of embolic members can be delivered into an implant, wherein successive embolic members in the series differ in their degree of concavity.

In an example, a series of embolic members can be delivered into an implant, wherein successive embolic members in the series decrease in size. In an example, a series of embolic members can be delivered into an implant, wherein embolic members in the series become progressively smaller (as one progresses along the series in a distal to proximal manner). In an example, a series of embolic members can be delivered into an implant, wherein successive embolic members in the series increase in size. In an example, a series of embolic members can be delivered into an implant, wherein embolic members in the series become progressively larger (as one progresses along the series in a distal to proximal manner).

In an example, embolic members can be soft, compressible members such as microsponges or blobs of gel. In an example, embolic members can be made from sponge, foam, or gel. In an example, embolic members can be hard, uncompressible members such as hard polymer spheres or beads. In an example, embolic members can be made from one or more materials selected from the group consisting of: cellulose, collagen, acetate, alginic acid, carboxy methyl cellulose, chitin, collagen glycosaminoglycan, divinylbenzene, ethylene glycol, ethylene glycol dimethylmathacrylate, ethylene vinyl acetate, hyaluronic acid, hydrocarbon polymer, hydroxyethylmethacrylate, methlymethacrylate, polyacrylic acid, polyamides, polyesters, polyolefins, polysaccharides, polyurethane, polyvinyl alcohol, silicone, urethane, and vinyl stearate.

In an example, embolic members can have a shape selected from the group consisting of: ball or sphere, ovoid, ellipsoid, and polyhedron. In an example, embolic members can have a Shore 00 value, indicative of softness or hardness, within a range of 5 to about 50. In an example, embolic members can have a diameter or like size within a range of 50 micrometers to 2000 micrometers. In an example, differently-sized embolic members can be used. In an example two or more different sizes of embolic members can be inserted into an implant to occlude an aneurysm. In an example, embolic members can include small balls and large balls. In an example, it may be advantageous to first fill an implant with larger balls and then continue filling the implant with smaller balls. In another example, it may be advantageous to first fill an implant with smaller balls and then continue filling the implant with larger balls.

In an example, an intrasaccular aneurysm occlusion device can be filled with a "string of pearls" string (or wire) connected sequence of embolic members. In an example, an intrasaccular aneurysm occlusion device can include a series of embolic members which are connected by a strand. In an example, a device can include a string of pearls" series of embolic members which are linked by a strand (e.g. a thin flexible member). In an example, a device can include a string of pearls" series of embolic members which are centrally linked by a strand (e.g. a thin flexible member). In an example, a "string of pearls" string-or-wire connected sequence of embolic members can comprise a plurality of embolic members which are separate from each other, but pair-wise connected to each other by at least one string or wire. In an example, a plurality of members can be unevenly-spaced along the longitudinal axis of a flexible member. In an example, uneven spacing of embolic members can be selected based on the size and shape of an aneurysm to be occluded. In an example, the distances between embolic members can vary. In an example, the space between embolic members can differ for occlusion of narrow-neck aneurysms vs. wide-neck aneurysms. In an example, distances between embolic members can become progressively shorter in a distal to proximal direction.

In an example, a line which connects embolic members can be a wire, spring, or chain. In an example, a connecting line can be a string, thread, band, fiber, or suture. In an example, embolic members can be centrally connected to each other by a connecting line. In an example, the centroids of embolic members can be connected by a connecting line. In an example, expanding arcuate embolic members can slide (e.g. up or down) along a connecting line. In an example, embolic members can slide along a connecting line, but only in one direction. In an example, a connecting line can have a ratchet structure which allows embolic members to slide closer to each other but not slide further apart. In an example, this device can further comprise a locking mechanism which stops embolic members from sliding along a connecting line. In an example, application of electromagnetic energy to a connecting line can fuse the line with embolic members and stop them from sliding, effectively locking them in proximity to each other.

In an example, embolic members can be conveyed through a lumen to an aneurysm in a fluid flow, wherein the fluid escapes out from an implant and embolic members are retained within the implant. In an example, embolic members can be conveyed through a lumen to an aneurysm by means of a moving belt or wire loop. In an example, embolic members can be conveyed through a lumen to an aneurysm by means of an Archimedes screw.

In an example, a method to occlude a cerebral aneurysm can comprise: receiving a 3D image of a cerebral aneurysm; and analyzing the 3D image to estimate an optimal amount of embolic members and/or material to be inserted into the aneurysm in order to occlude the aneurysm. In an example, an optimal amount of embolic members and/or material can be calculated by estimating the total interior volume of the aneurysm based on the 3D image of the aneurysm. In an example, estimation of the optimal amount of embolic members and/or material can depend on one or more factors selected from the group consisting of: general aneurysm shape or type; aneurysm size; aneurysm location; aneurysm rupture status; type of embolic material; shape of embolic material; size of embolic material; softness and/or compressibility of embolic material; parent vessel shape; parent vessel location; patient demographic information; and patient medical history.

In an example, embolic members and/or material can comprise embolic coils or ribbons. In an example, embolic members and/or material can comprise hydrogels or other gelatinous material. In an example, embolic members and/or material can comprise a string-of-pearls structure (i.e. a plurality of embolic members connected by a string, filament, wire, or micro-chain). In an example, a flow of liquid or gelatinous embolic material can be (automatically) pumped into a cerebral aneurysm until the optimal amount of embolic material has been dispensed. In an example, embolic members and/or material can be (automatically) delivered into a cerebral aneurysm until the optimal amount of embolic members has been dispensed.

In an example, this invention can be embodied in a method to create a device to occlude a cerebral aneurysm comprising: receiving a 3D image of a cerebral aneurysm; creating a 3D model or 3D mandrel based on the 3D image; and wrapping, weaving, braiding, melting, shrinking, or otherwise conforming wires around the 3D model or 3D mandrel in order to create a custom-shaped convex flexible wire mesh which is configured to be inserted into the aneurysm. In an example, embolic members and/or material can be inserted into the custom-shaped convex flexible wire mesh after the mesh has been inserted into the cerebral aneurysm.

In an example, an in-vivo 3D image of a cerebral aneurysm can be created by a medical imaging method selected from the group consisting of: Computerized Tomography (CT), Computerized Tomography Angiography (CTA), Cone Beam Computed Tomography (CBCT), Conoscopic Holography (CH), Digital Subtraction Angiography (DSA), Magnetic Resonance Angiography (MRA), Magnetic Resonance Imaging (MRI), Maximum Intensity Projection (MIP), Medical Holographic Imaging (MHI), Micro Computerized Tomography (MCT), Positron Emission Tomography (PET), Tuned-Aperture Computed Tomography (TACT), Doubting Thomagraphy (DT), and Ultrasound (U/S). In an example, an in-vivo 3D image of a cerebral aneurysm can be a digital image. In an example, an in-vivo 3D image of a cerebral aneurysm can be a volumetric image. In an example, an in-vivo 3D image can be constructed by digitally merging a plurality of 2D images from different perspectives or at different times. In an example, an in-vivo 3D image of a cerebral aneurysm can be created after injection of contrast media into a person's bloodstream.

In an example, there can be an optimal amount (or an optimal range of amounts) of embolic members and/or material which should be inserted into a flexible net, mesh, bag, liner, or stent within an aneurysm with a particular size and shape in order to occlude that aneurysm most effectively and safely. If the amount of embolic members and/or material inserted into a flexible net, mesh, bag, liner, or stent is less than this optimal amount, then there may be gaps between the flexible net, mesh, bag, liner, or stent and the walls of the aneurysm which allow blood to continue to flow into the aneurysm. If the amount of embolic members and/or material inserted into a flexible net, mesh, bag, liner, or stent is greater than this optimal amount, then the flexible net, mesh, bag, liner, or stent may exert too much pressure on the aneurysm walls (potentially causing the aneurysm to rupture); the flexible net, mesh, bag, liner, or stent may protrude out of the aneurysm into the parent vessel; or the flexible net, mesh, bag, liner, or stent may leak embolic material.

An optimal amount (or an optimal range of amounts) of embolic members and/or material to be inserted into a flexible net, mesh, bag, liner, or stent can be estimated by human judgment. In an example, estimation by human judgment of an optimal amount of embolic members and/or material to be inserted into a flexible net, mesh, bag, liner, or stent can be done based on medical imaging before an aneurysm occlusion procedure. In an example, estimation by human judgment of an optimal amount of embolic members and/or material to be inserted into a flexible net, mesh, bag, liner, or stent can be done based on real-time medical imaging during an aneurysm occlusion procedure.

However, an automated process to estimate an optimal amount of embolic members and/or material, such as a process using computer analysis of digital 3D images of an aneurysm, can be more accurate and quicker than estimation based on human judgment. This can help to reduce errors of under or over injection of embolic members and/or material and can also help to reduce aneurysm occlusion procedure time. In an example, there can be automated estimation of an optimal amount (or optimal amount range) of embolic members and/or material to be inserted into a flexible net, mesh, bag, liner, or stent in an cerebral aneurysm based on analysis of 3D images of that aneurysm.

In an example, an optimal amount (or an optimal range of amounts) of embolic members and/or material can be expressed as a volume, especially for a liquid or gelatinous embolic material which is dispensed (into a flexible net, mesh, bag, liner, or stent) in a flow. In an example, an optical amount (or an optimal range of amounts) of embolic members and/or material can be expressed as a percentage the interior volume of an aneurysm. In an example, an optimal amount (or optimal amount range) of embolic material volume can be calculated in steps comprising: (a) estimating the total interior volume of an aneurysm based on 3D images of the aneurysm; (a) subtracting the volume of the perimeter layer of a flexible net, mesh, bag, liner, or stent which is inserted into the aneurysm in order to calculate a remaining interior volume; and (c) expressing the optimal volume of embolic material to be inserted into the flexible net, mesh, bag, liner, or stent as a percentage of the remaining interior volume.

In an example, a string-of-pearls embolic structure which is inserted into a flexible net, mesh, bag, liner, or stent can comprise a plurality of embolic members (e.g. microsponges, microspheres, beads, or hydrogels) which are connected by one or more longitudinal flexible members (e.g. filaments, strings, threads, fibers, sutures, yarns, coils, or wires), wherein surfaces of the embolic members have microscale (or nanoscale) hook-and-eye structures which cause the embolic members to stick to each other upon contact. This can help to prevent the embolic members from leaking out of the flexible net, mesh, bag, liner, or stent. In an example, the embolic members can be separated from each other during delivery through a lumen so that they do not bunch together and clog the lumen, but can come into engaging contact with each other once they exit the lumen into the flexible net, mesh, bag, liner, or stent.

In an example, embolic members can adhere to each other. In an example, embolic members can adhere to each other after they are inserted into a flexible net, mesh, bag, liner, or stent so that they are less likely to escape out of holes in the flexible net, mesh, bag, liner, or stent. In an example, embolic members can adhere to each other after they are inserted into an aneurysm so that they are less likely to protrude out of the aneurysm into the parent vessel. In an example, embolic members and/or material can have a first level of adhesion (or stickiness) before they are inserted into an aneurysm and have a second level of adhesion (or stickiness) after they are inserted into the aneurysm, wherein the second level is greater than the first level. In an example, embolic members and/or material can be changed from a first level of adhesion (or stickiness) to a second level of adhesion (or stickiness) by a means selected from the group consisting of: exposure to blood; exposure to body thermal energy; selective application of a chemical substance by a provider and/or device operator; selective application of electromagnetic energy by a provider and/or device operator; selective application of light energy in a selected wavelength by a provider and/or device operator; and selective application of thermal energy by a provider and/or device operator.

In an example, embolic members and/or material can be fused, congealed, stuck, or adhered together after insertion into an aneurysm by selective intrasacular application of a chemical substance by a provider and/or device operator. In an example, embolic members and/or material can be fused, congealed, stuck, or adhered together after insertion by selective intrasacular application of electromagnetic energy by a provider and/or device operator. In an example, embolic members and/or material can be fused, congealed, stuck, or adhered together after insertion by selective intrasacular application of light energy in a selected wavelength by a provider and/or device operator. In an example, embolic members and/or material can be fused, congealed, stuck, or adhered together after insertion by selective intrasacular application of thermal energy by a provider and/or device operator.

In an example, the delivery of an optimal amount of embolic material or an optimal number of embolic members can be partially or fully automated based on an estimated amount (or range of amounts). In an example, a device can automatically control the amount of embolic material and/or number of embolic members inserted into a flexible net, mesh, bag, liner, or stent in order to insert an optimal amount of embolic material or an optimal number of embolic members. In an example, a device can automatically pump a flow of liquid or gelatinous embolic material into a flexible net, mesh, bag, liner, or stent until the optimal amount of embolic material has been dispensed. In an example, a device can automatically push a series of longitudinal embolic members (such as coils) into a flexible net, mesh, bag, liner, or stent until the optimal amount or number of embolic members has been dispensed. In an example, a device can automatically deliver a plurality of embolic members into a flexible net, mesh, bag, liner, or stent until the optimal number of embolic members has been dispensed.

In an example, a device can further comprise an embolic delivery component which measures and controls the insertion of embolic members and/or material into a flexible net, mesh, bag, liner, or stent within an aneurysm so that the optimal amount of embolic members and/or material is inserted. In an example, an embolic delivery component for a longitudinal embolic member or series of longitudinal members (such as coils) can measure and control the length or number of embolic members inserted into a flexible net, mesh, bag, liner, or stent within an aneurysm. In an example, an embolic delivery component to deliver an optimal length or number of longitudinal embolic members into a flexible net, mesh, bag, liner, or stent within an aneurysm can push a desired length or number of embolic members through a lumen into a flexible net, mesh, bag, liner, or stent within an aneurysm.

In an example, an embolic delivery component can selectively cut, sever, snap, melt, or segment (and detach) an otherwise continuous length of embolic material (such as a coil) after the optimal length of the material has been inserted into a flexible net, mesh, bag, liner, or stent within an aneurysm. In an example, an embolic delivery component can cut a longitudinal embolic member and detach the severed portion after an optimal length of the longitudinal embolic member has been inserted into a flexible net, mesh, bag, liner, or stent within an aneurysm. In an example, an embolic delivery component can melt a longitudinal embolic member and detach the severed portion after an optimal length of the longitudinal embolic member has been inserted into a flexible net, mesh, bag, liner, or stent within an aneurysm.

In an example, an embolic delivery component for a liquid or gelatinous embolic material can measure and control the flow of this embolic material into a flexible net, mesh, bag, liner, or stent within an aneurysm. In an example, an embolic delivery component for delivering a liquid or gelatinous embolic material can comprise a pump. In an example, an embolic delivery component for delivering a liquid or gelatinous embolic material can be selected from the group consisting of: axial pump, biochemical pump, biological pump, centrifugal pump, convective pump, diffusion pump, dispensing pump, effervescent pump, elastomeric pump, electrodiffusion pump, electrolytic pump, electromechanical pump, electroosmotic pump, fixed-occlusion peristaltic pump, gravity feed pump, helical pump, hose-type peristaltic pump, hydrolytic pump, In various examples, infusion pump, mechanical screw-type pump, Micro Electrical Mechanical System (MEMS) pump, micro pump, multiple-roller peristaltic pump, osmotic pump, peristaltic pump, piezoelectric pump, pulsatile pump, rotary pump, spring-loaded roller pump, tube-type peristaltic pump, and vapor pressure pump.

In an example, a liquid or gelatinous embolic material inserted into a flexible net, mesh, bag, liner, or stent can be a liquid polymer. In an example, a liquid or gelatinous embolic material inserted into a flexible net, mesh, bag, liner, or stent can be selected from the group consisting of: 2-octyl cyanoacrylate; ethyl-2-cyanoacrylate; methyl 2-cyanoacrylate; and n-butyl cyanoacrylate. In an example, a liquid or gelatinous embolic material inserted into a flexible net, mesh, bag, liner, or stent can be selected from the group consisting of: acrylamide-based hydrogel; acrylic-acid-based hydrogel; agar; alginate-based hydrogel; carboxymethyl cellulose; cellulose; chitin; chitosan; collagen; copolymeric hydrogel; gellan; gum arabic; heparin; homopolymeric hydrogel; hyaluronan; hydrocolloid hydrogel; methyl cellulose; multipolymer interpenetrating polymeric hydrogel; pectin; pluronic-acid-based hydrogel; polyacrylic-acid-based hydrogel; polypeptide-based; polyurethane-based; poly-vinyl-alcohol-based hydrogel; starch; superabsorbent hydrogel; superporous hydrogel; and xanthan.

In an example, guidance concerning the optimal amount of embolic members and/or material can be partially, but not fully, automated. In an example, an embolic delivery component can track and display the cumulative amount of embolic members and/or material which is being inserted into a flexible net, mesh, bag, liner, or stent during a procedure. In an example, an embolic delivery component can notify a provider and/or device operator in real time (e.g. with a visual, auditory, or tactile signal) as the cumulative amount of inserted embolic members and/or material is approaching the optimal amount. In an example, an embolic delivery component can notify a provider and/or device operator in real time (e.g. with a visual, auditory, or tactile signal) as the cumulative amount of inserted embolic members and/or material has reached the optimal amount. Example variations discussed in other portions of this disclosure or in priority-linked disclosures can also be applied to these examples where relevant, but are not repeated here in order to reduce narrative redundancy.

In an example, selected types of embolic members and/or material (e.g. those which are less likely to protrude out of an aneurysm into a parent vessel) can be delivered directly into an aneurysm sac without the need for a flexible net, mesh, bag, liner, or stent. In such examples, it can be useful to have an automated method for estimating the optimal amount of embolic members and/or material to be inserted into the aneurysm based on 3D imaging of the aneurysm. In an example, a method to determine an optimal amount of embolic members and/or material to be inserted into an cerebral aneurysm can comprise: (a) receiving a 3D image of a cerebral aneurysm; and (b) analyzing the 3D image to estimate an optimal amount (or an optimal range of amounts) of embolic members and/or material to be inserted into the aneurysm in order to occlude the aneurysm.

In an example, embolic members and/or material inserted into an aneurysm can be biocompatible yarn or fabric. In an example, embolic members and/or material inserted into an aneurysm can be blobs of gel. In an example, embolic members and/or material inserted into an aneurysm can be embolic coils. In an example, embolic members and/or material inserted into an aneurysm can be embolic gel which solidifies after insertion. In an example, embolic members and/or material inserted into an aneurysm can be embolic glue. In an example, embolic members and/or material inserted into an aneurysm can be embolic liquid which solidifies after insertion.

In an example, embolic members and/or material inserted into an aneurysm can be fiber strips. In an example, embolic members and/or material inserted into an aneurysm can be flexible wires. In an example, embolic members and/or material inserted into an aneurysm can be hydrogels. In an example, embolic members and/or material inserted into an aneurysm can be mesh ribbon. In an example, embolic members and/or material inserted into an aneurysm can be micro-beads. In an example, embolic members and/or material inserted into an aneurysm can be microscale mesh spheres.

In an example, embolic members and/or material inserted into an aneurysm can be microspheres. In an example, embolic members and/or material inserted into an aneurysm can be microsponges. In an example, embolic members and/or material inserted into an aneurysm can be stream of paste which solidifies after insertion. In an example, embolic material can comprise a shredded musical score, wherein a person can have a catchy tune stuck in their head. In an example, embolic members and/or material can be selected from the group consisting of: biocompatible yarn or fabric; blobs of gel; embolic coils; embolic gel which solidifies after insertion; embolic glue; embolic liquid which solidifies after insertion; fiber strips; flexible wires; hydrogels; mesh ribbon; micro-beads; microscale mesh spheres; microspheres; microsponges; stream of paste which solidifies after insertion; and string-of-pearls embolic structure (e.g. a plurality of embolic members connected by a string, filament, wire, or micro-chain). In an example, embolic members and/or material inserted into an aneurysm can be a string-of-pearls embolic structure (e.g. a plurality of embolic members inserted into an aneurysm connected by a string, filament, wire, or micro-chain).

In an example, embolic members can adhere to each other. In an example, embolic members can adhere to each other after they are inserted into a flexible net, mesh, bag, liner, or stent so that they are less likely to escape out of holes in the flexible net, mesh, bag, liner, or stent. In an example, embolic members can adhere to each other after they are inserted into an aneurysm so that they are less likely to protrude out of the aneurysm into the parent vessel. In an example, embolic members and/or material can have a first level of adhesion (or stickiness) before they are inserted into an aneurysm and have a second level of adhesion (or stickiness) after they are inserted into the aneurysm, wherein the second level is greater than the first level. In an example, embolic members and/or material can be changed from a first level of adhesion (or stickiness) to a second level of adhesion (or stickiness) by a means selected from the group consisting of: exposure to blood; exposure to body thermal energy; selective application of a chemical substance by a provider and/or device operator; selective application of electromagnetic energy by a provider and/or device operator; selective application of light energy in a selected wavelength by a provider and/or device operator; and selective application of thermal energy by a provider and/or device operator.

In an example, embolic members and/or material can be fused, congealed, stuck, or adhered together after insertion by selective intrasacular application of a chemical substance by a provider and/or device operator. In an example, embolic members and/or material can be fused, congealed, stuck, or adhered together after insertion by selective intrasacular application of electromagnetic energy by a provider and/or device operator. In an example, embolic members and/or material can be fused, congealed, stuck, or adhered together after insertion by selective intrasacular application of light energy in a selected wavelength by a provider and/or device operator. In an example, embolic members and/or material can be fused, congealed, stuck, or adhered together after insertion by selective intrasacular application of thermal energy by a provider and/or device operator.

In an example, a string-of-pearls embolic structure which is inserted into an aneurysm can comprise a plurality of embolic members (e.g. microsponges, microspheres, beads, or hydrogels) which are connected by one or more longitudinal flexible members (e.g. filaments, strings, threads, fibers, sutures, yarns, coils, or wires), wherein the surfaces of the embolic members have microscale (or nanoscale) hook-and-eye structures which cause the embolic members to stick to each other upon contact. This can help to prevent the embolic members from protruding out of the aneurysm. In an example, the embolic members can be separated from each other during delivery through a lumen so that they do not bunch together and clog the lumen, but can come into engaging contact with each other once they exit the lumen into the aneurysm.

In an example, an embolic delivery component for a liquid or gelatinous embolic material can measure and control the flow of this embolic material into an aneurysm. In an example, an embolic delivery component for a liquid or gelatinous embolic material can comprise a pump. In an example, an embolic delivery component for a liquid or gelatinous embolic material can be selected from the group consisting of: axial pump, biochemical pump, biological pump, centrifugal pump, convective pump, diffusion pump, dispensing pump, effervescent pump, elastomeric pump, electrodiffusion pump, electrolytic pump, electromechanical pump, electroosmotic pump, fixed-occlusion peristaltic pump, gravity feed pump, helical pump, hose-type peristaltic pump, hydrolytic pump, In various examples, infusion pump, mechanical screw-type pump, Micro Electrical Mechanical System (MEMS) pump, micro pump, multiple-roller peristaltic pump, osmotic pump, peristaltic pump, piezoelectric pump, pulsatile pump, rotary pump, spring-loaded roller pump, tube-type peristaltic pump, and vapor pressure pump.

In an example, a liquid or gelatinous embolic material can be selected from the group consisting of: 2-octyl cyanoacrylate; ethyl-2-cyanoacrylate; methyl 2-cyanoacrylate; and n-butyl cyanoacrylate. In an example, a liquid or gelatinous embolic material can be selected from the group consisting of: acrylamide-based hydrogel; acrylic-acid-based hydrogel; agar; alginate-based hydrogel; carboxymethyl cellulose; cellulose; chitin; chitosan; collagen; copolymeric hydrogel; gellan; gum arabic; heparin; homopolymeric hydrogel; hyaluronan; hydrocolloid hydrogel; methyl cellulose; multipolymer interpenetrating polymeric hydrogel; pectin; pluronic-acid-based hydrogel; polyacrylic-acid-based hydrogel; polypeptide-based; polyurethane-based; poly-vinyl-alcohol-based hydrogel; starch; superabsorbent hydrogel; superporous hydrogel; and xanthan. Other example variations discussed elsewhere in this disclosure or in priority-linked disclosures can also be applied to an example where relevant.

In an example, this device can further comprise a closure mechanism which closes an opening through an implant. In an example, this closure mechanism can be closed by the operator of the device after embolic members and/or material has been inserted into an implant. In an example, this closure mechanism can require action by a user during the procedure to close off the opening. In various examples, this closure mechanism can comprise a drawstring, loop, seal, fusible member, adhesive, snap, clip, valve, or cap. In an example, this closure mechanism can close automatically after embolic members and/or material has been inserted into an implant. In an example, a closure mechanism can be a valve. In an example, a closure mechanism can be a leaflet valve. In an example, a closure mechanism can be a one-way valve. In an example, a valve can allow embolic members and/or material to enter an implant through an opening in the implant, but not allow the embolic members and/or material to exit the implant.

In an example, a closure mechanism which closes an opening through an implant can be an electric detachment mechanism. In an example, this closure mechanism can be an elastic ring or band. In an example, this closure mechanism can be a threaded mechanism. In an example, this closure mechanism can be a sliding cover. In an example, this closure mechanism can be a sliding plug. In an example, this closure mechanism can be a filament loop. In an example, this closure mechanism can be an electromagnetic solenoid.

In an example, a closure mechanism which closes an opening through an implant can comprise a leaflet valve. In an example, this leaflet valve can be positioned in an opening (or lumen) through a mesh (or net) which bridges an aneurysm neck. When this leaflet valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this leaflet valve is in its closed configuration, it reduces blood flood through the opening in the mesh into the aneurysm. In other words, this leaflet valve can serve as a "closure mechanism" for an intrasacular aneurysm occlusion device.

In an example, a closure mechanism which closes an opening through an implant can comprise a bi-leaflet valve or a tri-leaflet valve, analogous to a heart valve. In an example, a valve can passively open when an embolic member is pushed through it and can passively close after the member passes through or when a portion of the member is detached. In an example, such a valve can allow an embolic member to be inserted into the flexible net, but the valve closes to reduce blood flow after the embolic member has passed through the valve. In an example, an active valve can be remotely opened and/or closed by the operator of the device. In an example, an active valve can be remotely opened and/or closed by an operator by the application of electromagnetic energy. In an example, an active valve can be remotely opened and/or closed by an operator by pulling a filament. In an example, an active valve can be remotely opened and/or closed by an operator by pushing, pulling, or rotating a wire.

In an example, a leaflet valve can have a single leaflet or flap. In an example, a leaflet valve can have four or more leaflets or flaps. In an example, a leaflet valve can passively open when an embolic member (such as an embolic coil, hydrogel, microsponge, bead, or a string-of-pearls embolic strand) pushes through it. In an example, a leaflet valve can passively close when after the embolic member has passed through. In an example, a leaflet valve can be made from an elastomeric material. In an example, a leaflet valve can be made from a silicone-based polymer. In an example, a leaflet valve can be made from rigid material such as metal. In an example, a leaflet valve can be made from titanium and carbon. In an example, a leaflet valve can be remotely opened and/or closed by the operator of the device. In an example, a leaflet valve can be remotely opened and/or closed by an operator by the application of electromagnetic energy.

In an example, a closure mechanism which closes an opening through an implant can comprise an elastic annular valve. In an example, this elastic annular valve can be positioned in an opening (or lumen) through a mesh (or net) which bridges an aneurysm neck. When this elastic annular valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this elastic annular valve is in its closed configuration, it reduces blood flood through the opening in the mesh into the aneurysm. In other words, this elastic annular valve can serve as a "closure mechanism" for an intrasacular aneurysm occlusion device. We all have times when we need closure. In an example, an elastic annular valve can passively open when an embolic member (such as an embolic coil, hydrogel, microsponge, bead, or a string-of-pearls embolic strand) pushes through it. In an example, an elastic annular valve can passively close when after the embolic member has passed through. In an example, an elastic annular valve can be made from an elastomeric material. In an example, an elastic annular valve can be made from a silicone-based polymer.

In an example, a closure mechanism which closes an opening through an implant can comprise a rotational valve. A rotational valve can comprise an (outer) first layer with a first opening (or hole) and an (inner) second layer with a second opening (or hole). When the first and second openings (holes) are not aligned, then the valve is in its closed configuration. When the first and second openings (holes) are aligned, then the valve is in its open configuration. In this example, the valve is changed from its closed configuration to its open configuration, or vice versa, by rotating (or revolving, pivoting, turning, or twisting) the first layer relative to the second layer, or vice versa. In an example, a rotational valve can comprise two or more overlapping (e.g. parallel) layers with openings (holes). When the openings (holes) of different layers are not aligned, then the valve is closed. When the opening (holes) of different layers are aligned, then the valve is open. In an example, the valve can be opened or closed by rotating one layer relative to the other layer. In an example, one or both layers can be rotated remotely by the operator of the device, enabling the operator to open or close the valve remotely.

In an example, a closure mechanism which closes an opening through an implant can comprise a rotational valve which is positioned in an opening (or lumen) through a mesh (or net) which bridges an aneurysm neck. When this rotational valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this rotational valve is in its closed configuration, it reduces blood flood through the opening in the mesh into the aneurysm. In other words, this rotational valve can serve as a "closure mechanism" for an intrasacular aneurysm occlusion device.

In an example, a closure mechanism which closes an opening through an implant can comprise a sliding valve. In an example, a sliding valve can comprise a layer with an opening (or hole) and a sliding flap (or lid). When the sliding flap (lid) covers the opening (hole), then the valve is in its closed configuration. When the sliding flap (lid) does not cover the opening (hole), then the valve is in its open configuration. In this example, the valve is changed from its closed configuration to its open configuration, or vice versa, by moving the sliding flap. In an example, the sliding flap can be moved remotely by the operator of the device, enabling the operator to open or close the valve remotely.

In an example, a closure mechanism which closes an opening through an implant can comprise a sliding valve which is positioned in an opening (or lumen) through a mesh (or net) which bridges an aneurysm neck. When this sliding valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this sliding valve is in its closed configuration, it reduces blood flood through the opening in the mesh into the aneurysm. In other words, this sliding valve can serve as a "closure mechanism" for an intrasacular aneurysm occlusion device.

In an example, a closure mechanism which closes an opening through an implant can comprise a pivoting valve. A pivoting value can comprise a lumen (opening) with a pivoting flap (or plug). When the pivoting flap (plug) blocks the lumen (opening), then the valve is in its closed configuration. When the pivoting flap (lid) does not block the lumen (opening), then the valve is in its open configuration. In this example, the valve is changed from its closed configuration to its open configuration, or vice versa, by pivoting (rotating) the flap around a central axis. In the example of a square opening, a valve could changed from its closed configuration to its open configuration, or vice versa, by pivoting (rotating) a flap around one side. In an example, the pivoting flap can be moved remotely by the operator of the device, enabling the operator to open or close the valve remotely. This type of pivoting valve is analogous to the valves which are used in circular air ducts for HVAC (heating, ventilation, and air conditioning) systems in buildings.

In an example, a closure mechanism which closes an opening through an implant can comprise a pivoting valve which is positioned in an opening (or lumen) through a mesh (or net) which bridges an aneurysm neck. When this pivoting valve is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. This type of pivoting valve is more appropriate for liquid embolic material than for coils, beads, or string-of-pearls strands which might get snagged on it. When this pivoting valve is in its closed configuration, it reduces blood flood through the opening in the mesh into the aneurysm. In other words, this pivoting valve can serve as a "closure mechanism" for an intrasacular aneurysm occlusion device. We all have times when we need closure.

In an example, a closure mechanism which closes an opening through an implant can comprise a plug mechanism. In an example, an active valve can be remotely opened and/or closed by an operator by cutting, pulling, or pushing a flap or plug. In an example, a plug mechanism can comprise a lumen (opening) and a plug which is inserted into the lumen. When a plug blocks the lumen (opening), then the plug mechanism is in its closed configuration. When a plug does not block the lumen (opening), then the plug mechanism is in its open configuration. In this example, the plug mechanism is changed from its open configuration to its closed configuration by inserting a plug into the lumen (opening) In an example, a plug can be inserted remotely by the operator of the device, enabling the operator to close the plug mechanism remotely. In an example, a plug can be inserted into a lumen by using a guidewire or hydraulic pressure. In an example, a plug can be made from hydrogel.

In an example, a closure mechanism which closes an opening through an implant can comprise a plug mechanism which is positioned in an opening (or lumen) through a mesh (or net) which bridges an aneurysm neck. When this plug mechanism is in its open configuration, embolic members (such as embolic coils, hydrogels, microsponges, beads, or string-of-pearls embolic strands) or liquid embolic material (which solidifies in the aneurysm) can be inserted through the opening in the mesh into an aneurysm. When this plug mechanism is in its closed configuration, it reduces blood flood through the opening in the mesh into the aneurysm.

I claim:

1. A method for occluding a cerebral aneurysm can comprise:
　delivering a flexible implant through a longitudinal lumen to a cerebral aneurysm, wherein the flexible implant has a compressed first configuration as it is delivered through the lumen;
　inserting the flexible implant into the aneurysm sac from the lumen, wherein the flexible implant self-expands into an expanded second configuration in the aneurysm sac;
　delivering embolic members through an opening in the flexible implant into an interior of the flexible implant, wherein accumulation of embolic members inside the flexible implant causes the flexible implant to further expand into a third configuration in the aneurysm sac, wherein the third configuration is larger than the second configuration, and wherein the third configuration conforms to the walls of the aneurysm sac more closely than the second configuration; wherein a first subset of the embolic members is delivered into the implant at a first time during expansion of the implant from the second configuration to the third configuration; wherein embolic members in the first subset are made from a first material with a first durometer level; wherein shapes of embolic members in the first subset are selected from the group consisting of: spherical, ellipsoidal, globular, oblate spheroid, ovaloid, prolate-spheroid-shaped, cubic, hexahedron, octahedron, polyhedron-shaped, pyramidal, and tetrahedronal; wherein a second subset of the embolic members is delivered into the implant at a second time during expansion of the implant from the second configuration to the third configuration; wherein embolic members in the second subset are made from a second material with a second durometer level; wherein the second durometer level is less than the first durometer level; wherein shapes of embolic members in the second subset are selected from the group consisting of: spherical, ellipsoidal, globular, oblate spheroid, ovaloid, prolate-spheroid-shaped, cubic, hexahedron, octahedron, polyhedron-shaped, pyramidal, and tetrahedronal;
　closing the opening through the flexible implant; and
　detaching and withdrawing the lumen from the flexible implant.

2. A method for occluding a cerebral aneurysm can comprise:
　delivering a flexible implant through a longitudinal lumen to a cerebral aneurysm, wherein the flexible implant has a radially-constrained first configuration as it is delivered through the lumen;
　inserting the flexible implant into the aneurysm sac from the lumen, wherein the flexible implant self-expands in the aneurysm sac into a second configuration which is symmetric with respect to the implant's longitudinal axis;
　delivering embolic members through an opening in the flexible implant into an interior of the flexible implant, wherein accumulation of embolic members causes the flexible implant to further expand into a third configuration in the aneurysm sac which is asymmetric with respect to the implant's longitudinal axis; wherein a first subset of the embolic members is delivered into the implant at a first time during expansion of the implant from the second configuration to the third configuration; wherein embolic members in the first subset are made from a first material with a first durometer level; wherein shapes of embolic members in the first subset are selected from the group consisting of: spherical, ellipsoidal, globular, oblate spheroid, ovaloid, prolate-spheroid-shaped, cubic, hexahedron, octahedron, polyhedron-shaped, pyramidal, and tetrahedronal; wherein a second subset of the embolic members is delivered into the implant at a second time during expansion of the implant from the second configuration to the third configuration; wherein embolic members in the second subset are made from a second material with a second durometer level; wherein the second durometer level is less than the first durometer level; wherein shapes of embolic members in the second subset are selected from the group consisting of: spherical, ellipsoidal, globular, oblate spheroid, ovaloid, prolate-spheroidshaped, cubic, hexahedron, octahedron, polyhedron-shaped, pyramidal, and tetrahedronal; and detaching and withdrawing the lumen from the flexible implant.

3. A method for occluding a cerebral aneurysm can comprise:

delivering a flexible implant through a longitudinal lumen to a cerebral aneurysm, wherein the flexible implant has a radially-constrained first configuration as it is delivered through the lumen;

inserting the flexible implant into the aneurysm sac from the lumen, wherein the flexible implant self-expands into a radially-expanded second configuration in the aneurysm sac;

delivering embolic members through an opening in the flexible implant into an interior of the flexible implant, wherein accumulation of embolic members inside the flexible implant causes the flexible implant to further expand into a third configuration in the aneurysm sac, wherein expansion of a distal portion of the flexible implant from the second configuration to the third configuration is greater than expansion of the proximal portion of the flexible implant from the second configuration to the third configuration; wherein a first subset of the embolic members is delivered into the implant at a first time during expansion of the implant from the second configuration to the third configuration; wherein embolic members in the first subset are made from a first material with a first durometer level; wherein shapes of embolic members in the first subset are selected from the group consisting of: spherical, ellipsoidal, globular, oblate spheroid, ovaloid, prolate-spheroid-shaped, cubic, hexahedron, octahedron, polyhedron-shaped, pyramidal, and tetrahedronal; wherein a second subset of the embolic members is delivered into the implant at a second time during expansion of the implant from the second configuration to the third configuration; wherein embolic members in the second subset are made from a second material with a second durometer level; wherein the second durometer level is less than the first durometer level; wherein shapes of embolic members in the second subset are selected from the group consisting of: spherical, ellipsoidal, globular, oblate spheroid, ovaloid, prolate-spheroid-shaped, cubic, hexahedron, octahedron, polyhedron-shaped, pyramidal, and tetrahedronal;

closing the opening through the flexible implant; and detaching and withdrawing the lumen from the flexible implant.

\* \* \* \* \*